(12) United States Patent
Robertson et al.

(10) Patent No.: US 8,785,502 B2
(45) Date of Patent: Jul. 22, 2014

(54) COMPOSITIONS AND METHODS RELATING TO PROLIFERATIVE DISEASES

(75) Inventors: Gavin P. Robertson, Hummelstown, PA (US); Chandagalu D. Raghavendragowda, Hershey, PA (US); SubbaRao V. Madhunapantula, Peddapuram (IN); Omer F. Kuzu, Harrisburg, PA (US); Gajanan S. Inamdar, Belgaum (IN)

(73) Assignee: The Penn State Research Foundation, University Park, PA (US)

( * ) Notice: Subject to any disclaimer, the term of this patent is extended or adjusted under 35 U.S.C. 154(b) by 57 days.

(21) Appl. No.: 13/312,682

(22) Filed: Dec. 6, 2011

(65) Prior Publication Data
US 2012/0141578 A1    Jun. 7, 2012

Related U.S. Application Data

(60) Provisional application No. 61/420,094, filed on Dec. 6, 2010, provisional application No. 61/466,572, filed on Mar. 23, 2011.

(51) Int. Cl.
*A61K 31/135* (2006.01)
*A61K 9/127* (2006.01)

(52) U.S. Cl.
USPC .......................................... 514/655; 424/450

(58) Field of Classification Search
None
See application file for complete search history.

(56) References Cited

U.S. PATENT DOCUMENTS

| | | | |
|---|---|---|---|
| 4,282,253 A | 8/1981 | Steck | |
| 4,755,523 A | 7/1988 | Yoshikuni et al. | |
| 5,248,696 A | 9/1993 | Bang et al. | |
| 7,015,248 B2 | 3/2006 | Lin et al. | |
| 7,342,125 B2 | 3/2008 | Palladino et al. | |
| 2003/0092674 A1 | 5/2003 | Saxena et al. | |
| 2003/0125380 A1 | 7/2003 | Saxena et al. | |

FOREIGN PATENT DOCUMENTS

| | | |
|---|---|---|
| CN | 101580477 | 11/2009 |
| DE | 1138777 | * 10/1962 |

OTHER PUBLICATIONS

Registry No. 1446-61-3 (Entered STN Nov. 16, 1984; accessed Jun. 6, 2013).*
Allen, T.M. Current Opinion in Colloid & Interface Science, 1996, vol. 1, pp. 645-651.*
English Translation of DE 1138777, machine translated from EPO website on Jan. 9, 2014.*
Chen et al. Linchan Huaxue Yu Gongye, 2009, vol. 29 (Suppl.), pp. 121-124) (English Abstract attached).*
Gonzalez, A. et al., Synthesis and biological evaluation of dehydroabietic acid derivatives, *European Journal of Medicinal Chemistry*, 45: 811-16, 2010.
Gonzalez, M. et al., Synthesis and biological evaluation of abietic acid derivatives, *European Journal of Medicinal Chemistry*, 44: 2468-72, 2009.
Rao, X. et al., Synthesis and Antitumor Activity of Novel Alpha-Aminophosphonates from Diterpenic Dehydroabietylamine, *Heteroatom Chemistry*, 19(5): 512-16, 2008.
Li, F. et al., Cytotoxic effect and pro-apoptotic mechanism of TBIDOM, a novel dehydroabietylamine derivative, on human hepatocellular carcinoma SMMC-7721 cells, *Journal of Pharmacy and Pharmacology*, 60(2): 202-11, Feb. 2008.

* cited by examiner

*Primary Examiner* — James D Anderson
(74) *Attorney, Agent, or Firm* — Gifford, Krass, Sprinkle, Anderson & Citkowski, P.C.

(57) ABSTRACT

Anti-cancer compositions and methods are described herein. In particular, compositions including one or more of leelamine, a leelamine derivative, abietylamine, an abietylamine derivative, and an abietic acid derivative are described. Methods for treatment of pathological conditions particularly cancer, in a subject using one or more of leelamine, a leelamine derivative, abietylamine, an abietylamine derivative, and an abietic acid derivative are described herein.

5 Claims, 35 Drawing Sheets

Leelamine hydrochloride
1-Phenanthrenemethanamine,1,2,3,4,4a,9,10,10a-Octahydro-
1,4a-dimethyl-7-(1-methylethyl)-(1R,4aS,10aR) hydrochloride
Molecular weight : 330.94

TABLE 1

IC$_{50}$ (μmol/L) of leelamine against melanoma and other malignancies

Melanoma cell lines

| Treatment time (h) | Normal cells | | | RGP | | VGP | | MM | | |
|---|---|---|---|---|---|---|---|---|---|---|
| | FOM103 | FF2441 | HFK | WM35 | SbCl-2 | WM115 | WM278.1 | SKMEL-24 | 1205 Lu | UACC 903 |
| 24 | 8.33 ± 0.86 | 9.57 ± 0.36 | 10.01 ± 0.36 | 7.02 ± 1.18 | 7.41 ± 0.69 | 4.79 ± 0.44 | 4.44 ± 0.65 | 1.97 ± 0.12 | 2.49 ± 0.30 | 1.78 ± 0.11 |
| 48 | 6.47 ± 0.42 | 5.98 ± 0.98 | 8.95 ± 0.57 | 4.83 ± 1.28 | 4.68 ± 0.92 | 3.17 ± 0.09 | 4.04 ± 0.04 | 1.66 ± 0.21 | 1.63 ± 0.26 | 1.19 ± 0.32 |
| 72 | 5.33 ± 0.22 | 5.17 ± 0.18 | 8.40 ± 0.70 | 2.99 ± 0.61 | 3.72 ± 0.55 | 2.41 ± 0.14 | 2.27 ± 0.07 | 1.47 ± 0.25 | 1.35 ± 0.11 | 1.07 ± 0.04 |

Other cancer types

| Cancer type | Breast | | Lung | Prostate | Fibro sarcoma | Pancreas | Colon | | |
|---|---|---|---|---|---|---|---|---|---|
| Cell lines | MDA-MB-231 | MCF-7 | A-549 | LnCap | PC-3 | HT-1080 | MiaPaca-2 | HCT-116 | HT-29 | SW-480 |
| 24 h | 5.82 ± 0.87 | 7.12 ± 1.3 | 8.81 ± 0.82 | 10.90 ± 0.23 | 5.41 ± 2.60 | 4.01 ± 0.27 | 4.69 ± 0.37 | 4.80 ± 0.50 | 5.95 ± 1.23 | 1.55 ± 0.33 |

Figure 20

|  | Empty liposme | Nanolipolee-007 |  |
|---|---|---|---|
| SGOT(AST)<br>(110 - 247 u/L) | 97.5 | 107.0 | Liver function |
| SGPT(ALT)<br>(33.4 - 132 u/L) | 37.0 | 44.0 | |
| ALKP<br>(62.0 - 209 u/L) | 82.0 | 109.5 | |
| ALB<br>(2.5 - 4.8 mg/dL) | 2.30 | 2.35 | |
| TBIL<br>(0.1 - 0.9 mg/dL) | 0.25 | 0.30 | |
| CREA<br>(0.2 - 0.31 mg/dL) | 0.20 | 0.20 | Kidney funtion |
| BUN<br>(18 - 33.7 mg/dL) | 21.5 | 18.5 | |
| CHOL<br>(36 - 96 mg/dL) | 135.0 | 148.0 | Lipid profile |
| TRIG<br>(55 - 144 mg/dL) | 239.5 | 302.0 | |
| GLU<br>(198 - 232 mg/dL) | 187.0 | 266.5 | Glucose level |

Figure 31

Abietic Acid Esters $R_6$ = Alkyl, Trityl, $Br_3CCO$, $CH_3CO$, $F_3CCO$
-Aryl, Hetroaryl,
-Benzyl, Substituted Benzyl, Hetroaryl-methyl, Aroyl, Hetero-aroyl Alkyl = Methyl, Ethyl, etc.
$Br_3CCO$ = Tribromoacetyl; $CH_3CO$ = Acetyl; $F_3CCO$ = Trifloroacetyl Includes all the above derivatives, but not limited to the above sustituents

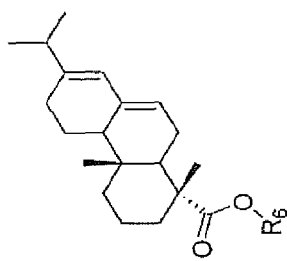

$R_6$ = Me = (1R,4aR)-methyl 7-isopropyl-1,4a-dimethyl-1,2,3,4,4a,4b,5,6,10,10a-decahydrophenanthrene-1-carboxylate $R_6$ = Et = (1R,4aR)-ethyl 7-isopropyl-1,4a-dimethyl-1,2,3,4,4a,4b,5,6,10,10a-decahydrophenanthrene-1-carboxylate $R_6$ = Bz = (1R,4aR)-benzyl 7-isopropyl-1,4a-dimethyl-1,2,3,4,4a,4b,5,6,10,10a-decahydrophenanthrene-1-carboxylate $R_6$ = Tr = (1R,4aR)-trityl 7-isopropyl-1,4a-dimethyl-1,2,3,4,4a,4b,5,6,10,10a-decahydrophenanthrene-1-carboxylate $R_6$ = H = (1R,4aR)-7-isopropyl-1,4a-dimethyl-1,2,3,4,4a,4b,5,6,10,10a-decahydrophenanthrene-1-carboxylic acid $R_6$ = $F_3C(CO)$ = 2,2,2-trifluoroacetic (1R,4aR)-7-isopropyl-1,4a-dimethyl-1,2,3,4,4a,4b,5,6,10,10a-decahydrophenanthrene-1-carboxylic anhydride $R_6$ = $Br_3C(CO)$ = 2,2,2-tribromoacetic (1R,4aR)-7-isopropyl-1,4a-dimethyl-1,2,3,4,4a,4b,5,6,10,10a-decahydrophenanthrene-1-carboxylic anhydride $R_6$ = $H_3C(CO)$ = acetic (1R,4aR)-7-isopropyl-1,4a-dimethyl-1,2,3,4,4a,4b,5,6,10,10a-decahydrophenanthrene-1-carboxylic anhydride

FIGURE 45

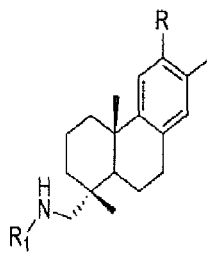

Leelamine Derivatives

R = Br, Cl, F
-COOH, -COOR', -CONH$_2$
-NH$_2$, -NHR$_2$, -NCS, -NCSe, -NCO
-NHC(O)NHR$_2$, -NHC(S)NHR$_2$, -NHC(Se)NHR$_2$, -NHC(NH)NHR$_2$
-Aryl, Hetroaryl, Heteromethyl, R$_1$= Alkyl, Trityl, Br$_3$CCO, CH$_3$CO, F$_3$CCO
-COOH, -COOR$_3$, -CONH$_2$
-NH$_2$, -NHR$_3$, -NCS, -NCSe, -NCO
-C(O)NHR$_3$, -C(S)NHR$_3$, -C(Se)NHR$_3$, -C(NH)NHR$_3$
-Aryl, Hetroaryl, Het,
-Benzyl, Substituted Benzyl, Hetroaryl-methyl, Aroyl, Hetero-aroyl R$_2$ and R$_3$ = Alkyl, Aryl, Aroyl, Hetroaryl, etc Br =Bromo; C = Chloro; F = Fluoro
-COOH = Carboxylic acid; -COOR$_4$ = Esters; -CONH$_2$ = Amides
-NH$_2$ = Amine; -NCS = Isothiocyante; -NCO = Isocyanate; -NCSe = Isoselenocyante
-C(O)NH$_2$ = Urea; -C(S)NH$_2$ = Thiourea; -C(Se)NH$_2$ = Selenourea; -C(NH)NH$_2$= Guanidine <u>Includes all the above derivatives, but not limited to the above sustituents</u>

R= Br = ((1R,4aS)-6-bromo-7-isopropyl-1,4a-dimethyl-1,2,3,4,4a,9,10,10a-octahydrophenanthren-1-yl)methanamine
R= Cl= ((1R,4aS)-6-chloro-7-isopropyl-1,4a-dimethyl-1,2,3,4,4a,9,10,10a-octahydrophenanthren-1-yl)methanamine
R= F =((1R,4aS)-6-fluoro-7-isopropyl-1,4a-dimethyl-1,2,3,4,4a,9,10,10a-octahydrophenanthren-1-yl)methanamine
R= -COOH = (4bS,8R)-8-(aminomethyl)-2-isopropyl-4b,8-dimethyl-4b,5,6,7,8,8a,9,10-octahydrophenanthrene-3-carboxylic acid
R= -NH2 = (4bS,8R)-8-(aminomethyl)-2-isopropyl-4b,8-dimethyl-4b,5,6,7,8,8a,9,10-octahydrophenanthren-3-amine R$_1$= Me = 1-((1R,4aS)-7-isopropyl-1,4a-dimethyl-1,2,3,4,4a,9,10,10a-octahydrophenanthren-1-yl)-N-methylmethanamine
R$_1$= Ph = N-(((1R,4aS)-7-isopropyl-1,4a-dimethyl-1,2,3,4,4a,9,10,10a-octahydrophenanthren-1-yl)methyl)aniline
R$_1$= NCS = (1R,4aS)-7-isopropyl-1-(isothiocyanatomethyl)-1,4a-dimethyl-1,2,3,4,4a,9,10,10a-octahydrophenanthrene
R$_1$= NCSe = (1R,4aS)-7-isopropyl-1-(isoselenocyanatomethyl)-1,4a-dimethyl-1,2,3,4,4a,9,10,10a-octahydrophenanthrene
R$_1$=NCO = (1R,4aS)-1-(isocyanatomethyl)-7-isopropyl-1,4a-dimethyl-1,2,3,4,4a,9,10,10a-octahydrophenanthrene
R$_1$=C(O)NH2 = 1-(((1R,4aS)-7-isopropyl-1,4a-dimethyl-1,2,3,4,4a,9,10,10a-octahydrophenanthren-1-yl)methyl)urea
R$_1$=C(S)NH2 =1-(((1R,4aS)-7-isopropyl-1,4a-dimethyl-1,2,3,4,4a,9,10,10a-octahydrophenanthren-1-yl)methyl)thiourea
R$_1$=C(Se)NH2 = 1-(((1R,4aS)-7-isopropyl-1,4a-dimethyl-1,2,3,4,4a,9,10,10a-octahydrophenanthren-1-yl)methyl)selenourea
R$_1$= C(NH)NH2 =1-(((1R,4aS)-7-isopropyl-1,4a-dimethyl-1,2,3,4,4a,9,10,10a-octahydrophenanthren-1-yl)methyl)guanidine

FIGURE 46

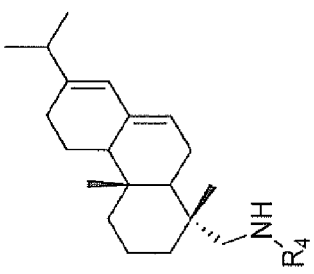

Abietylamine Derivatives

$R_4$ = Alkyl, Trityl, $Br_3CCO$, $CH_3CO$, $F_3CCO$
- $NH_2$, $-NHR_1$, -NCS, -NCSe, -NCO
- $-C(O)NHR_1$, $-C(S)NHR_1$, $-C(Se)NHR_1$, $-C(NH)NHR_1$
- Aryl, Hetroaryl,
- Benzyl, Substituted Benzyl, Hetroaryl-methyl, Aroyl, Hetero-aroyl Alkyl = Methyl, Ethyl, etc
$Br_3CCO$ = Tribromoacetyl
$F_3CCO$ = Trifluroacetyl $R_1$ = Alkyl, Aryl, Aroyl, Hetroaryl, etc $-CONH_2$ = Amides
-NCS = Isothiocyante; -NCO = Isocyanate; -NCSe = Isoselenocyante
$-C(O)NH_2$ = Urea; $-C(S)NH_2$ = Thiourea; $-C(Se)NH_2$ = Selenourea; $-C(NH)NH_2$ = Guanidine <u>Includes all the above derivatives, but not limited to the above sustituents</u>

$R_4$ = Me = 1-((1R,4aS)-7-isopropyl-1,4a-dimethyl-1,2,3,4,4a,9,10,10a-octahydrophenanthren-1-yl)-N-methylmethanamine
$R_4$ = Ph = N-(((1R,4aS)-7-isopropyl-1,4a-dimethyl-1,2,3,4,4a,9,10,10a-octahydrophenanthren-1-yl)methyl)aniline
$R_4$ = NCS = (1R,4aS)-7-isopropyl-1-(isothiocyanatomethyl)-1,4a-dimethyl-1,2,3,4,4a,9,10,10a-octahydrophenanthrene
$R_4$ = NCSe = (1R,4aS)-7-isopropyl-1-(isoselenocyanatomethyl)-1,4a-dimethyl-1,2,3,4,4a,9,10,10a-octahydrophenanthrene
$R_4$ = NCO = (1R,4aS)-1-(isocyanatomethyl)-7-isopropyl-1,4a-dimethyl-1,2,3,4,4a,9,10,10a-octahydrophenanthrene
$R_4$ = C(O)NH2 = 1-(((1R,4aS)-7-isopropyl-1,4a-dimethyl-1,2,3,4,4a,9,10,10a-octahydrophenanthren-1-yl)methyl)urea
$R_4$ = C(S)NH2 =1-(((1R,4aS)-7-isopropyl-1,4a-dimethyl-1,2,3,4,4a,9,10,10a-octahydrophenanthren-1-yl)methyl)thiourea
$R_4$ = C(Se)NH2 = 1-(((1R,4aS)-7-isopropyl-1,4a-dimethyl-1,2,3,4,4a,9,10,10a-octahydrophenanthren-1-yl)methyl)selenourea
$R_4$ = C(NH)NH2 =1-(((1R,4aS)-7-isopropyl-1,4a-dimethyl-1,2,3,4,4a,9,10,10a-octahydrophenanthren-1-yl)methyl)guanidine

FIGURE 47

Scheme 1

Scheme 2

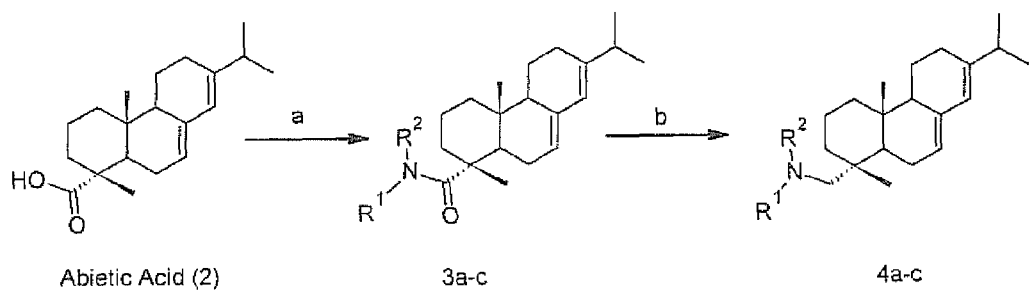

Abietic Acid (2)    3a-c    4a-c

3a=R$^1$R$^2$=H$_2$ a) NH$_3$(g), MDC, icebath then rt o.n.
3b=R$^1$=CH$_3$ R$^2$=H a) CH$_3$NH$_2$ in THF, MDC, icebath then rt o.n.
3c=R$^1$R$^2$=C$_2$H$_5$ a) (C$_2$H$_5$)$_2$NH$_2$, MDC, icebath then rt o.n.

b=LiAlH$_4$ in THF icebath then rt o.n.
4a=R$^1$R$^2$=H
4b=R$^1$=CH$_3$ R$^2$=H
4c=R$^1$R$^2$=C$_2$H$_5$

Figure 50

Scheme 3

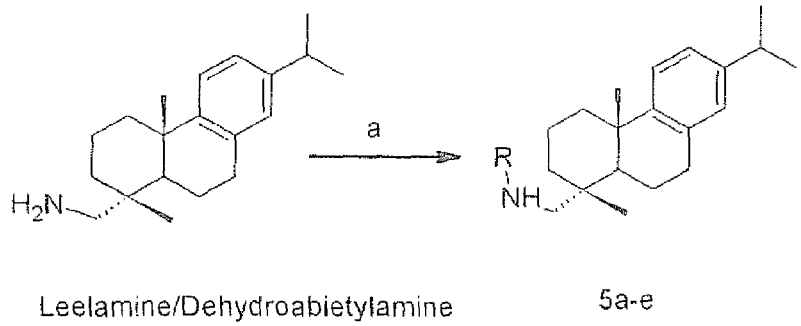

Leelamine/Dehydroabietylamine    5a-e

5a=R=F$_3$CCO, a)F$_3$CCO$_2$Et, TEA, MDC, icebath then rt o.n.
5b=R=CH$_3$CO a)H$_3$CCOCl, TEA MDC, icebath then rt o.n.
5c=R=C$_6$H$_5$CO a)C$_6$H$_5$COCl, TEA, MDC, icebath then rt o.n.
5d=R=C$_6$H$_5$CH$_2$ a)C$_6$H$_5$CH$_2$Br, TEA THF, Reflux
5e=R=(C$_6$H$_5$)$_3$CH a)(C$_6$H$_5$)$_3$CHCl, TEA, MDC, icebath then rt o.n.

Figure 51

COMPOSITIONS AND METHODS RELATING TO PROLIFERATIVE DISEASES

REFERENCE TO RELATED APPLICATIONS

This application claims priority from U.S. Provisional Patent Application Ser. No. 61/420,094, filed Dec. 6, 2010 and 61/466,572, filed Mar. 23, 2011. The entire content of both applications is incorporated herein by reference.

GOVERNMENT SUPPORT

This invention was made with government support under Grant Nos. CA127892, CA138634 and CA136667 awarded by the National Institutes of Health. The Government has certain rights in the invention.

FIELD OF THE INVENTION

The present invention relates generally to anti-cancer compositions and methods. In specific aspects, the present invention relates to compositions including one or more of: leelamine, a leelamine derivative, abietylamine, an abietylamine derivative, and an abietic acid derivative; methods for treatment of pathological conditions in a subject using one or more of: leelamine, a leelamine derivative, abietylamine, an abietylamine derivative, and an abietic acid derivative.

BACKGROUND OF THE INVENTION

In spite of recent medical progress, cancer continues to be one of the most common and deadly diseases. Elucidation of biochemical pathways involved in development and progression of various cancers is important to identify potential anti-cancer treatments as well as to develop agents effective to regulate such pathways in other aspects of health and disease.

A particular cancer, melanoma, is the most deadly form of skin cancer due to its high metastatic potential. The well-known phosphoinositide 3 kinase (PI3K), mitogen-activated kinase (MAPK) and STAT pathways are activated in 50-70% of melanomas, functioning to reduce cellular apoptosis, increase proliferation and aid the invasive processes through the lymphatic system to promote melanoma metastasis development.

There is a continuing need for compositions and methods to treat cancer.

Compositions and methods are required to inhibit the PI3K, MAPK and STAT pathways and inhibit abnormal cell survival and proliferation.

SUMMARY OF THE INVENTION

Leelamine derivatives, abietylamine derivatives, and abietic acid derivatives are provided according to aspects of the present invention.

As will be appreciated compounds are referred to herein by common nomenclature, "shorthand" nomenclature created for convenience, and systematic chemical nomenclature. In some case, two or more names are used to refer to the same compound. For example, "abietyl alcohol/GPR-8/[(1R,4aR)-1,4a-dimethyl-7-(propan-2-yl)-1,2,3,4,4a,4b,5,6,10,10a-decahydrophenanthren-1-yl]methanol" includes three names referring to the same compound, a common name/shorthand name/systematic chemical name. In other cases, a compound shown or described herein is referred to simply by a "shorthand" name associated with a chemical structure and/or common name or systematic chemical name, such as "GPR-8" or "5a," in text or figures.

Leelamine derivatives having the structure:

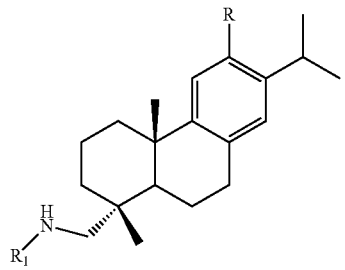

(1)

where R is selected from the group consisting of: H; Br; Cl; F; —COOH; —COOR1; —CONH$_2$; —NH$_2$; —NHR2; —NCS; —NCSe; —NCO; —NHC(O)NHR2; —NHC(S)NHR2; —NHC(Se)NHR2; —NHC(NH)NHR2; $C_1$-$C_5$ straight chain or branched alkyl; $C_6H_5$ unsubstituted aryl; $C_6H_5$ aryl substituted with a substituent selected from: $C_1$-$C_5$ straight chain or branched alkyl, F, Cl, Br, I, and O—$C_1$-$C_5$ where $C_1$-$C_5$ is straight chain or branched alkyl; heteroaryl; and heteromethyl having a heteroatom selected from nitrogen, sulfur and oxygen; where R1 is selected from the group consisting of: $C_1$-$C_5$ straight chain or branched alkyl; trityl; Br$_3$CCO (tribromoacetyl); CH$_3$CO (acetyl); F$_3$CCO (trifluoroacetyl); —COOH; —COOR3; —CONH$_2$; —NH$_2$; —NHR3; —NCS; —NCSe; —NCO; —C(O)NHR3; —C(S)NHR3; —C(Se)NHR3; —C(NH)NHR3; unsubstituted aryl; $C_6H_5$ aryl substituted with a substituent selected from $C_1$-$C_5$ straight chain or branched alkyl, F, Cl, Br, I, and O—$C_1$-$C_5$ where $C_1$-$C_5$ is straight chain or branched alkyl; heteroaryl; heteromethyl; unsubstituted benzyl; benzyl substituted with substituted with a substituent selected from $C_1$-$C_5$ straight chain or branched alkyl, F, Cl, Br, I, —NH$_2$, —CN, —CONH$_2$, —COOH, and O—$C_1$-$C_5$ where $C_1$-$C_5$ is straight chain or branched alkyl; a three to six member saturated heterocycle having at least one nitrogen; heteroaryl-methyl; aroyl; and hetero-aroyl; and where each R2 and R3 is independently selected from the group consisting of: $C_1$-$C_5$ straight chain or branched alkyl; unsubstituted aryl; $C_6H_5$ aryl substituted with a substituent selected from: $C_1$-$C_5$ straight chain or branched alkyl, F, Cl, Br, I, and O—$C_1$-$C_5$ where $C_1$-$C_5$ is straight chain or branched alkyl; a three to six member saturated heterocycle having at least one nitrogen; aroyl; heteroaryl; aralkyl; and heteroaralkyl, are provided according to aspects of the present invention.

Abietylamine derivatives having the structure:

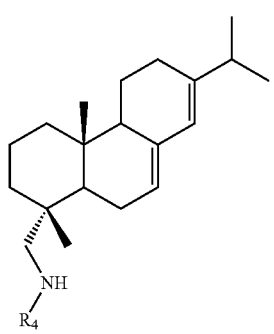

(2)

where R4 is selected from the group consisting of: $C_1$-$C_5$ straight chain or branched alkyl; F, Cl, Br, I, O—$C_1$-$C_5$ where $C_1$-$C_5$ is straight chain or branched alkyl; trityl; $Br_3CCO$ (tribromoacetyl); $CH_3CO$ (acetyl); $F_3CCO$ (trifluoroacetyl); —$NH_2$; —NHR1; —NCS; —NCSe; —NCO; —C(O)NHR1; —C(S)NHR1; —C(Se)NHR1; —C(NH)NHR1; $C_6H_5$ unsubstituted aryl; $C_6H_5$ aryl substituted with a substituent selected from: $C_1$-$C_5$ straight chain or branched alkyl, F, Cl, Br, and I, O—$C_1$-$C_5$ where $C_1$-$C_5$ is straight chain or branched alkyl; heteroaryl, unsubstituted benzyl; benzyl substituted with a substituent selected from $C_1$-$C_5$ straight chain or branched alkyl, F, Cl, Br, I, —$NH_2$, —CN, —$CONH_2$, —COOH, and O—$C_1$-$C_5$ where $C_1$-$C_5$ is straight chain or branched alkyl; heteroaryl-methyl; aroyl; and hetero-aroyl, and where each R1 is independently selected from the group consisting of: $C_1$-$C_5$ straight chain or branched alkyl; $C_6H_5$ unsubstituted aryl; $C_6H_5$ aryl substituted with a substituent selected from: $C_1$-$C_5$ straight chain or branched alkyl, F, Cl, Br, I, and O—$C_1$-$C_5$ where $C_1$-$C_5$ is straight chain or branched alkyl; aroyl, heteroaryl; aralkyl; and heteroaralkyl are provided according to aspects of the present invention.

Abietylamine derivatives having the structure:

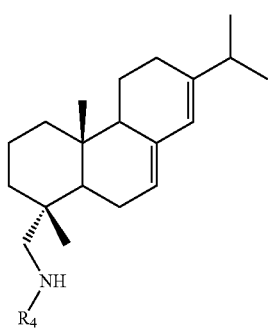

(2)

where R4 is methyl or ethyl are provided according to aspects of the present invention.

Abietic acid derivatives having the structure:

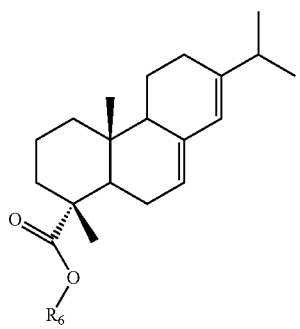

(3)

where R6 is selected from the group consisting of: $C_1$-$C_5$ straight chain or branched alkyl; F, Cl, Br, I, O—$C_1$-$C_5$ where $C_1$-$C_5$ is straight chain or branched alkyl, trityl, $Br_3CCO$ (tribromoacetyl), $CH_3CO$ (acetyl), $F_3CCO$ (trifluoroacetyl), $C_6H_5$ unsubstituted aryl; $C_6H_5$ aryl substituted with a substituent selected from $C_1$-$C_5$ straight chain or branched alkyl, F, Cl, Br, I, and O—$C_1$-$C_5$ where $C_1$-$C_5$ is straight chain or branched alkyl, heteroaryl, unsubstituted benzyl; benzyl substituted with a substituent selected from: $C_1$-$C_5$ straight chain or branched alkyl, F, Cl, Br, I, —$NH_2$, —CN, —CONH2, —COOH and O—$C_1$-$C_5$ where $C_1$-$C_5$ is straight chain or branched alkyl; heteroaryl-methyl; aroyl; and heteroaroyl are provided according to aspects of the present invention.

Abietic acid derivatives having the structure:

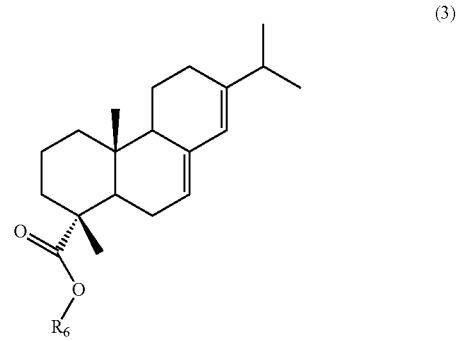

(3)

where R6 is methyl or ethyl are provided according to aspects of the present invention.

Abietylamine derivatives having structure:

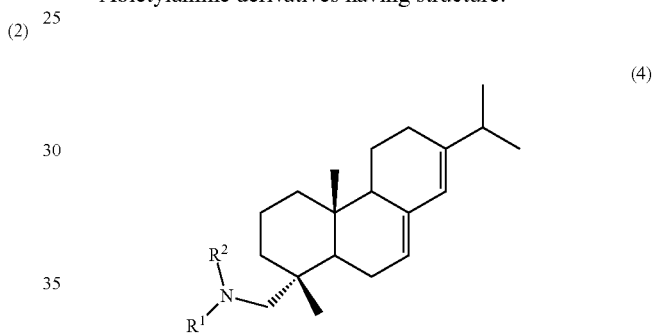

(4)

where R1 and R2 are each independently H, methyl or ethyl, with the proviso that R1 and R2 are not both H, are provided according to aspects of the present invention.

Abietyl alcohol/GPR-8/[(1R,4aR)-1,4a-dimethyl-7-(propan-2-yl)-1,2,3,4,4a,4b,5,6,10,10a-decahydrophenanthren-1-yl]methanol; abietylamine/GPR-3{[(1R,4aR)-1,4a-dimethyl-7-(propan-2-yl)-1,2,3,4,4a,4b,5,6,10,10a-decahydrophenanthren-1-yl]methyl}amine; abieticamide/GPR-2/(1R,4aR)-1,4a-dimethyl-7-(propan-2-yl)-1,2,3,4,4a,4b,5,6,10,10a-decahydrophenanthrene-1-carboxamide; N-methylabieticamide/GPR-6/(1R,4aR)—N,1,4a-trimethyl-7-(propan-2-yl)-1,2,3,4,4a,4b,5,6,10,10a-decahydrophenanthrene-1-carboxamide; N-methylabietylamine/GPR-7/{[(1R,4aR)-1,4a-dimethyl-7-(propan-2-yl)-1,2,3,4,4a,4b,5,6,10,10a-decahydrophenanthren-1-yl]methyl}(methyl)amine; N,N-diethylabieticamide/GPR-11/(1R,4aR)—N,N-diethyl-1,4a-dimethyl-7-(propan-2-yl)-1,2,3,4,4a,4b,5,6,10,10a-decahydrophenanthrene-1-carboxamide; N,N-diethylabietylamine/GPR-12{[(1R,4aR)-1,4a-dimethyl-7-(propan-2-yl)-1,2,3,4,4a,4b,5,6,10,10a-decahydrophenanthren-1-yl]methyl}diethylamine; leelamine/[(1R,4aS)-1,4a-dimethyl-7-(propan-2-yl)-1,2,3,4,4a,9,10,10a-octahydrophenanthren-1-yl]methanamine; N-acetylleelamine/GPR-4L/N-{[(1R,4aS)-1,4a-dimethyl-7-(propan-2-yl)-1,2,3,4,4a,9,10,10a-octahydrophenanthren-1-yl]methyl}acetamide; N-trifluoroacetylleelamine/GPR-1L/N-{[(1R,4aS)-1,4a-dimethyl-7-(propan-2-yl)-1,2,3,4,4a,9,10,10a-octahydrophenanthren-1-yl]methyl}-2,2,2-trifluoroacetamide; N-tribromoacetylleelamine/GPR-5L/N-

{[(1R,4aS)-1,4a-dimethyl-7-(propan-2-yl)-1,2,3,4,4a,9,10,10a-octahydrophenanthren-1-yl]methyl}-2,2,2-tribromoacetamide; N-benzoylleelamine/GPR-7L/N-(((1R,4aS)-7-isopropyl-1,4a-dimethyl-1,2,3,4,4a,9,10,10a-octahydrophenanthren-1-yl)methyl)benzamide; and N-benzylleelamine/GPR-8L/N-benzyl-1-((1R,4aS)-7-isopropyl-1,4a-dimethyl-1,2,3,4,4a,9,10,10a-octahydrophenanthren-1-yl)methanamine are provided according to aspects of the present invention.

Anti-cancer pharmaceutical compositions including leelamine, a leelamine derivative, abietylamine, an abietylamine derivative, and/or an abietic acid derivative; and a pharmaceutically acceptable carrier, are provided according to aspects of the present invention.

Anti-cancer pharmaceutical compositions including a pharmaceutically acceptable carrier and one or more leelamine derivatives having the structure:

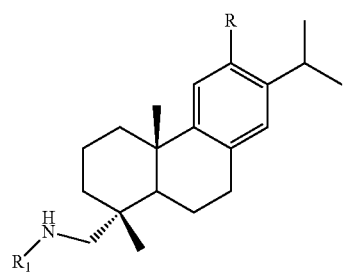

(1)

where R is selected from the group consisting of: H; Br; Cl; F; —COOH; —COOR1; —CONH$_2$; —NH$_2$; —NHR2; —NCS; —NCSe; —NCO; —NHC(O)NHR2; —NHC(S)NHR2; —NHC(Se)NHR2; —NHC(NH)NHR2; $C_1$-$C_5$ straight chain or branched alkyl; $C_6H_5$ unsubstituted aryl; $C_6H_5$ aryl substituted with a substituent selected from: $C_1$-$C_5$ straight chain or branched alkyl, F, Cl, Br, I, and O—$C_1$-$C_5$ where $C_1$-$C_5$ is straight chain or branched alkyl; heteroaryl; and heteromethyl having a heteroatom selected from nitrogen, sulfur and oxygen; where R1 is selected from the group consisting of: $C_1$-$C_5$ straight chain or branched alkyl; trityl; Br$_3$CCO (tribromoacetyl); CH$_3$CO (acetyl); F$_3$CCO (trifluoroacetyl); —COOH; —COOR3; —CONH$_2$; —NH$_2$; —NHR3; —NCS; —NCSe; —NCO; —C(O)NHR3; —C(S)NHR3; —C(Se)NHR3; —C(NH)NHR3; unsubstituted aryl; $C_6H_5$ aryl substituted with a substituent selected from $C_1$-$C_5$ straight chain or branched alkyl, F, Cl, Br, I, and O—$C_1$-$C_5$ where $C_1$-$C_5$ is straight chain or branched alkyl; heteroaryl; heteromethyl; unsubstituted benzyl; benzyl substituted with substituted with a substituent selected from $C_1$-$C_5$ straight chain or branched alkyl, F, Cl, Br, I, —NH2, —CN, —CONH2, —COOH, and O—$C_1$-$C_5$ where $C_1$-$C_5$ is straight chain or branched alkyl; a three to six member saturated heterocycle having at least one nitrogen; heteroaryl-methyl; aroyl; and hetero-aroyl; and where each R2 and R3 is independently selected from the group consisting of: $C_1$-$C_5$ straight chain or branched alkyl; unsubstituted aryl; $C_6H_5$ aryl substituted with a substituent selected from: $C_1$-$C_5$ straight chain or branched alkyl, F, Cl, Br, I, and O—$C_1$-$C_5$ where $C_1$-$C_5$ is straight chain or branched alkyl; a three to six member saturated heterocycle having at least one nitrogen; aroyl; heteroaryl; aralkyl; and heteroaralkyl, are provided according to aspects of the present invention.

Anti-cancer pharmaceutical compositions including a pharmaceutically acceptable carrier and one or more abietylamine derivatives having the structure:

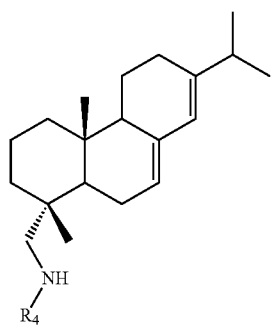

(2)

where R4 is selected from the group consisting of: $C_1$-$C_5$ straight chain or branched alkyl; F, Cl, Br, I, O—$C_1$-$C_5$ where $C_1$-$C_5$ is straight chain or branched alkyl; trityl; Br$_3$CCO (tribromoacetyl); CH$_3$CO (acetyl); F$_3$CCO (trifluoroacetyl); —NH$_2$; —NHR1; —NCS; —NCSe; —NCO; —C(O)NHR1; —C(S)NHR1; —C(Se)NHR1; —C(NH)NHR1; $C_6H_5$ unsubstituted aryl; $C_6H_5$ aryl substituted with a substituent selected from: $C_1$-$C_5$ straight chain or branched alkyl, F, Cl, Br, and I, O—$C_1$-$C_5$ where $C_1$-$C_5$ is straight chain or branched alkyl; heteroaryl, unsubstituted benzyl; benzyl substituted with a substituent selected from $C_1$-$C_5$ straight chain or branched alkyl, F, Cl, Br, I, —NH2, —CN, —CONH2, —COOH, and O—$C_1$-$C_5$ where $C_1$-$C_5$ is straight chain or branched alkyl; heteroaryl-methyl; aroyl; and hetero-aroyl, and where each R1 is independently selected from the group consisting of: $C_1$-$C_5$ straight chain or branched alkyl; $C_6H_5$ unsubstituted aryl; $C_6H_5$ aryl substituted with a substituent selected from: $C_1$-$C_5$ straight chain or branched alkyl, F, Cl, Br, I, and O—$C_1$-$C_5$ where $C_1$-$C_5$ is straight chain or branched alkyl; aroyl, heteroaryl; aralkyl; and heteroaralkyl are provided according to aspects of the present invention.

Anti-cancer pharmaceutical compositions including a pharmaceutically acceptable carrier and one or more abietylamine derivatives having the structure:

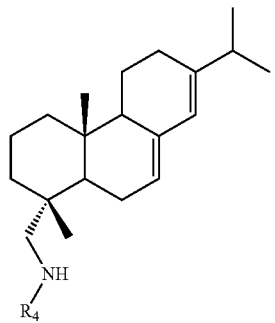

(2)

where R4 is methyl or ethyl.

Anti-cancer pharmaceutical compositions including a pharmaceutically acceptable carrier and one or more abietic acid derivatives having the structure:

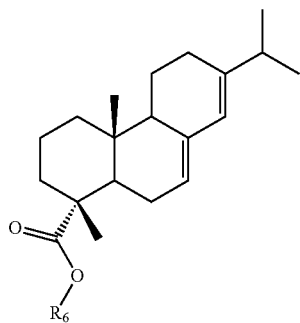

(3)

where R6 is selected from the group consisting of: $C_1$-$C_5$ straight chain or branched alkyl; F, Cl, Br, I, O—$C_1$-$C_5$ where $C_1$-$C_5$ is straight chain or branched alkyl, trityl, $Br_3CCO$ (tribromoacetyl), $CH_3CO$ (acetyl), $F_3CCO$ (trifluoroacetyl), $C_6H_5$ unsubstituted aryl; $C_6H_5$ aryl substituted with a substituent selected from $C_1$-$C_5$ straight chain or branched alkyl, F, Cl, Br, I, and O—$C_1$-$C_5$ where $C_1$-$C_5$ is straight chain or branched alkyl, heteroaryl, unsubstituted benzyl; benzyl substituted with a substituent selected from: $C_1$-$C_5$ straight chain or branched alkyl, F, Cl, Br, I, —$NH_2$, —CN, —$CONH_2$, —COOH and O—$C_1$-$C_5$ where $C_1$-$C_5$ is straight chain or branched alkyl; heteroaryl-methyl; aroyl; and heteroaroyl are provided according to aspects of the present invention.

Anti-cancer pharmaceutical compositions including a pharmaceutically acceptable carrier and one or more abietic acid derivatives having the structure:

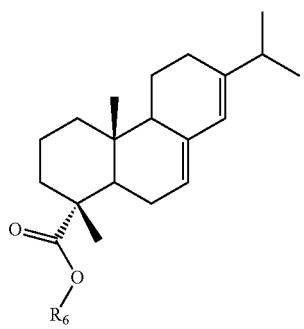

(3)

where R6 is methyl or ethyl are provided according to aspects of the present invention.

Anti-cancer pharmaceutical compositions including a pharmaceutically acceptable carrier and one or more abietylamine derivatives having structure:

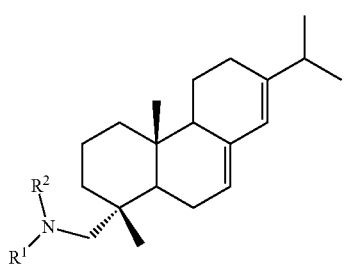

(4)

where R1 and R2 are each independently H, methyl or ethyl, with the proviso that R1 and R2 are not both H, are provided according to aspects of the present invention.

Anti-cancer pharmaceutical compositions are provided according to aspects of the present invention which include a pharmaceutically acceptable carrier and one or more anti-cancer compositions selected from the group consisting of: leelamine, abietylamine, abietyl alcohol/GPR-8/[(1R,4aR)-1,4a-dimethyl-7-(propan-2-yl)-1,2,3,4,4a,4b,5,6,10,10a-decahydrophenanthren-1-yl]methanol; abietylamine/GPR-3{[(1R,4aR)-1,4a-dimethyl-7-(propan-2-yl)-1,2,3,4,4a,4b,5,6,10,10a-decahydrophenanthren-1-yl]methyl}amine; abieticamide/GPR-2/(1R,4aR)-1,4a-dimethyl-7-(propan-2-yl)-1,2,3,4,4a,4b,5,6,10,10a-decahydrophenanthrene-1-carboxamide; N-methylabieticamide/GPR-6/(1R,4aR)—N,1,4a-trimethyl-7-(propan-2-yl)-1,2,3,4,4a,4b,5,6,10,10a-decahydrophenanthrene-1-carboxamide; N-methylabietylamine/GPR-7/{[(1R,4aR)-1,4a-dimethyl-7-(propan-2-yl)-1,2,3,4,4a,4b,5,6,10,10a-decahydrophenanthren-1-yl]methyl}(methyl)amine; N,N-diethylabieticamide/GPR-11/(1R,4aR)—N,N-diethyl-1,4a-dimethyl-7-(propan-2-yl)-1,2,3,4,4a,4b,5,6,10,10a-decahydrophenanthrene-1-carboxamide; N,N-diethylabietylamine/GPR-12/{[(1R,4aR)-1,4a-dimethyl-7-(propan-2-yl)-1,2,3,4,4a,4b,5,6,10,10a-decahydrophenanthren-1-yl]methyl}diethylamine; leelamine/[(1R,4aS)-1,4a-dimethyl-7-(propan-2-yl)-1,2,3,4,4a,9,10,10a-octahydrophenanthren-1-yl]methanamine; N-acetylleelamine/GPR-4L N-{[(1R,4aS)-1,4a-dimethyl-7-(propan-2-yl)-1,2,3,4,4a,9,10,10a-octahydrophenanthren-1-yl]methyl}acetamide; N-trifluoroacetylleelamine/GPR-1L/N-{[(1R,4aS)-1,4a-dimethyl-7-(propan-2-yl)-1,2,3,4,4a,9,10,10a-octahydrophenanthren-1-yl]methyl}-2,2,2-trifluoroacetamide; N-tribromoacetylleelamine/GPR-5L/N-{[(1R,4aS)-1,4a-dimethyl-7-(propan-2-yl)-1,2,3,4,4a,9,10,10a-octahydrophenanthren-1-yl]methyl}-2,2,2-tribromoacetamide; N-benzoylleelamine/GPR-7L/N-(((1R,4aS)-7-isopropyl-1,4a-dimethyl-1,2,3,4,4a,9,10,10a-octahydrophenanthren-1-yl)methyl)benzamide; and N-benzylleelamine/GPR-8L/N-benzyl-1-((1R,4aS)-7-isopropyl-1,4a-dimethyl-1,2,3,4,4a,9,10,10a-octahydrophenanthren-1-yl)methanamine.

Anti-cancer pharmaceutical compositions are provided according to aspects of the present invention which include a pharmaceutically acceptable carrier and one or more anti-cancer compositions selected from the group consisting of: leelamine, abietylamine/GPR-3/{[(1R,4aR)-1,4a-dimethyl-7-(propan-2-yl)-1,2,3,4,4a,4b,5,6,10,10a-decahydrophenanthren-1-yl]methyl}amine; N-methylabietylamine/GPR-7/{[(1R,4aR)-1,4a-dimethyl-7-(propan-2-yl)-1,2,3,4,4a,4b,5,6,10,10a-decahydrophenanthren-1-yl]methyl}(methyl)amine; N-trifluoroacetylleelamine/GPR-1L/N-{[(1R,4aS)-1,4a-dimethyl-7-(propan-2-yl)-1,2,3,4,4a,9,10,10a-octahydrophenanthren-1-yl]methyl}-2,2,2-trifluoroacetamide; and N-tribromoacetylleelamine/GPR-5L/N-{[(1R,4aS)-1,4a-dimethyl-7-(propan-2-yl)-1,2,3,4,4a,9,10,10a-octahydrophenanthren-1-yl]methyl}-2,2,2-tribromoacetamide.

Anti-cancer pharmaceutical compositions including leelamine, a leelamine derivative, abietylamine, an abietylamine derivative, and/or an abietic acid derivative; and a pharmaceutically acceptable liposome carrier, are provided according to aspects of the present invention.

Anti-cancer pharmaceutical liposome compositions including one or more leelamine derivatives having the structure:

(1)

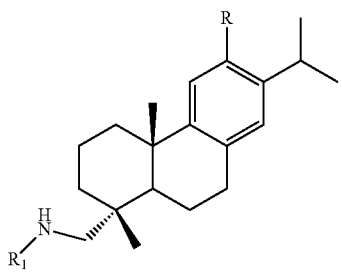

where R is selected from the group consisting of: H; Br; Cl; F; —COOH; —COOR1; —CONH₂; —NH₂; —NHR2; —NCS; —NCSe; —NCO; —NHC(O)NHR2; —NHC(S)NHR2; —NHC(Se)NHR2; —NHC(NH)NHR2; $C_1$-$C_5$ straight chain or branched alkyl; $C_6H_5$ unsubstituted aryl; $C_6H_5$ aryl substituted with a substituent selected from: $C_1$-$C_5$ straight chain or branched alkyl, F, Cl, Br, I, and O—$C_1$-$C_5$ where $C_1$-$C_5$ is straight chain or branched alkyl; heteroaryl; and heteromethyl having a heteroatom selected from nitrogen, sulfur and oxygen; where R1 is selected from the group consisting of: $C_1$-$C_5$ straight chain or branched alkyl; trityl; $Br_3CCO$ (tribromoacetyl); $CH_3CO$ (acetyl); $F_3CCO$ (trifluoroacetyl); —COOH; —COOR3; —CONH₂; —NH₂; —NHR3; —NCS; —NCSe; —NCO; —C(O)NHR3; —C(S)NHR3; —C(Se)NHR3; —C(NH)NHR3; unsubstituted aryl; $C_6H_5$ aryl substituted with a substituent selected from $C_1$-$C_5$ straight chain or branched alkyl, F, Cl, Br, I, and O—$C_1$-$C_5$ where $C_1$-$C_5$ is straight chain or branched alkyl; heteroaryl; heteromethyl; unsubstituted benzyl; benzyl substituted with substituted with a substituent selected from $C_1$-$C_5$ straight chain or branched alkyl, F, Cl, Br, I, —NH2, —CN, —CONH2, —COOH, and O—$C_1$-$C_5$ where $C_1$-$C_5$ is straight chain or branched alkyl; a three to six member saturated heterocycle having at least one nitrogen; heteroaryl-methyl; aroyl; and hetero-aroyl; and where each R2 and R3 is independently selected from the group consisting of: $C_1$-$C_5$ straight chain or branched alkyl; unsubstituted aryl; $C_6H_5$ aryl substituted with a substituent selected from: $C_1$-$C_5$ straight chain or branched alkyl, F, Cl, Br, I, and O—$C_1$-$C_5$ where $C_1$-$C_5$ is straight chain or branched alkyl; a three to six member saturated heterocycle having at least one nitrogen; aroyl; heteroaryl; aralkyl; and heteroaralkyl, are provided according to aspects of the present invention.

Anti-cancer pharmaceutical liposome compositions including one or more abietylamine derivatives having the structure:

(2)

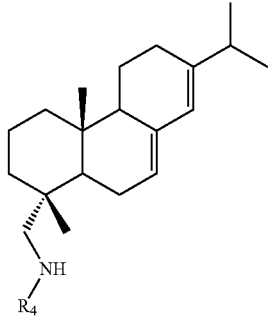

where R4 is selected from the group consisting of: $C_1$-$C_5$ straight chain or branched alkyl; F, Cl, Br, I, O—$C_1$-$C_5$ where $C_1$-$C_5$ is straight chain or branched alkyl; trityl; $Br_3CCO$ (tribromoacetyl); $CH_3CO$ (acetyl); $F_3CCO$ (trifluoroacetyl); —NH₂; —NHR1; —NCS; —NCSe; —NCO; —C(O)NHR1; —C(S)NHR1; —C(Se)NHR1; —C(NH)NHR1; $C_6H_5$ unsubstituted aryl; $C_6H_5$ aryl substituted with a substituent selected from: $C_1$-$C_5$ straight chain or branched alkyl, F, Cl, Br, and I, O—$C_1$-$C_5$ where $C_1$-$C_5$ is straight chain or branched alkyl; heteroaryl, unsubstituted benzyl; benzyl substituted with a substituent selected from $C_1$-$C_5$ straight chain or branched alkyl, F, Cl, Br, I, —NH2, —CN, —CONH2, —COOH, and O—$C_1$-$C_5$ where $C_1$-$C_5$ is straight chain or branched alkyl; heteroaryl-methyl; aroyl; and hetero-aroyl, and where each R1 is independently selected from the group consisting of: $C_1$-$C_5$ straight chain or branched alkyl; $C_6H_5$ unsubstituted aryl; $C_6H_5$ aryl substituted with a substituent selected from: $C_1$-$C_5$ straight chain or branched alkyl, F, Cl, Br, I, and O—$C_1$-$C_5$ where $C_1$-$C_8$ is straight chain or branched alkyl; aroyl, heteroaryl; aralkyl; and heteroaralkyl are provided according to aspects of the present invention.

Anti-cancer pharmaceutical liposome compositions including one or more abietylamine derivatives having the structure:

(2)

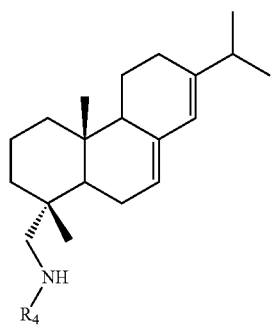

where R4 is methyl or ethyl.

Anti-cancer pharmaceutical liposome compositions including one or more abietic acid derivatives having the structure:

(3)

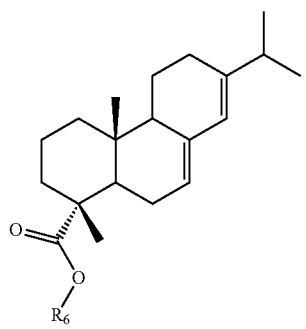

where R6 is selected from the group consisting of: $C_1$-$C_5$ straight chain or branched alkyl; F, Cl, Br, I, O—$C_1$-$C_5$ where $C_1$-$C_5$ is straight chain or branched alkyl, trityl, $Br_3CCO$ (tribromoacetyl), $CH_3CO$ (acetyl), $F_3CCO$ (trifluoroacetyl), $C_6H_5$ unsubstituted aryl; $C_6H_5$ aryl substituted with a substituent selected from $C_1$-$C_5$ straight chain or branched alkyl, F, Cl, Br, I, and O—$C_1$-$C_5$ where $C_1$-$C_5$ is straight chain or branched alkyl, heteroaryl, unsubstituted benzyl; benzyl substituted with a substituent selected from: $C_1$-$C_5$ straight chain or branched alkyl, F, Cl, Br, I, —$NH_2$, —CN, —$CONH_2$, —COOH and O—$C_1$-$C_5$ where $C_1$-$C_5$ is straight chain or branched alkyl; heteroaryl-methyl; aroyl; and heteroaroyl are provided according to aspects of the present invention. Anti-cancer pharmaceutical compositions including a pharmaceutically acceptable carrier and one or more abietic acid derivatives having the structure:

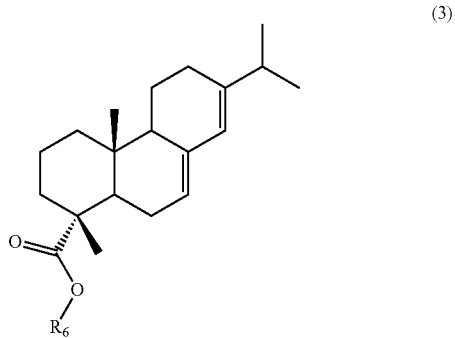

(3)

where R6 is methyl or ethyl are provided according to aspects of the present invention.

Anti-cancer pharmaceutical liposome compositions including one or more abietylamine derivatives having structure:

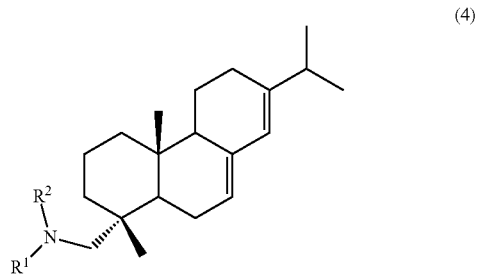

(4)

where R1 and R2 are each independently H, methyl or ethyl, with the proviso that R1 and R2 are not both H, are provided according to aspects of the present invention.

Anti-cancer pharmaceutical liposome compositions including one or more anti-cancer compositions selected from the group consisting of: leelamine, abietylamine, abietyl alcohol/GPR-8/[(1R,4aR)-1,4a-dimethyl-7-(propan-2-yl)-1,2,3,4,4a,4b,5,6,10,10a-decahydrophenanthren-1-yl]methanol; abietylamine/GPR-3/{[(1R,4aR)-1,4a-dimethyl-7-(propan-2-yl)-1,2,3,4,4a,4b,5,6,10,10a-decahydrophenanthren-1-yl]methyl}amine; abieticamide/GPR-2/(1R,4aR)-1,4a-dimethyl-7-(propan-2-yl)-1,2,3,4,4a,4b,5,6,10,10a-decahydrophenanthrene-1-carboxamide; N-methylabieticamide/GPR-6/(1R,4aR)—N,1,4a-trimethyl-7-(propan-2-yl)-1,2,3,4,4a,4b,5,6,10,10a-decahydrophenanthrene-1-carboxamide; N-methylabietylamine/GPR-7/{[(1R,4aR)-1,4a-dimethyl-7-(propan-2-yl)-1,2,3,4,4a,4b,5,6,10,10a-decahydrophenanthren-1-yl]methyl}(methyl)amine; N,N-diethylabieticamide/GPR-11/(1R,4aR)—N,N-diethyl-1,4a-dimethyl-7-(propan-2-yl)-1,2,3,4,4a,4b,5,6,10,10a-decahydrophenanthrene-1-carboxamide; N,N-diethylabietylamine/GPR-12/{[(1R,4aR)-1,4a-dimethyl-7-(propan-2-yl)-1,2,3,4,4a,4b,5,6,10,10a-decahydrophenanthren-1-yl]methyl}diethylamine; leelamine/[(1R,4aS)-1,4a-dimethyl-7-(propan-2-yl)-1,2,3,4,4a,9,10,10a-octahydrophenanthren-1-yl]methanamine; N-acetylleelamine/GPR-4L/N-{[(1R,4aS)-1,4a-dimethyl-7-(propan-2-yl)-1,2,3,4,4a,9,10,10a-octahydrophenanthren-1-yl]methyl}acetamide; N-trifluoroacetylleelamine/GPR-1L/N-{[(1R,4aS)-1,4a-dimethyl-7-(propan-2-yl)-1,2,3,4,4a,9,10,10a-octahydrophenanthren-1-yl]methyl}-2,2,2-trifluoroacetamide; N-tribromoacetylleelamine/GPR-5L/N-{[(1R,4aS)-1,4a-dimethyl-7-(propan-2-yl)-1,2,3,4,4a,9,10,10a-octahydrophenanthren-1-yl]methyl}-2,2,2-tribromoacetamide; N-benzoylleelamine/GPR-7L/N-(((1R,4aS)-7-isopropyl-1,4a-dimethyl-1,2,3,4,4a,9,10,10a-octahydrophenanthren-1-yl)methyl)benzamide; and N-benzylleelamine/GPR-8L/N-benzyl-1-((1R,4aS)-7-isopropyl-1,4a-dimethyl-1,2,3,4,4a,9,10,10a-octahydrophenanthren-1-yl)methanamine, are provided according to aspects of the present invention.

Anti-cancer pharmaceutical liposome compositions including one or more anti-cancer compositions selected from the group consisting of: leelamine, abietylamine/GPR-3/{[(1R,4aR)-1,4a-dimethyl-7-(propan-2-yl)-1,2,3,4,4a,4b,5,6,10,10a-decahydrophenanthren-1-yl]methyl}amine; N-methylabietylamine/GPR-7/{[(1R,4aR)-1,4a-dimethyl-7-(propan-2-yl)-1,2,3,4,4a,4b,5,6,10,10a-decahydrophenanthren-1-yl]methyl}(methyl)amine; N-trifluoroacetylleelamine/GPR-1L/N-{[(1R,4aS)-1,4a-dimethyl-7-(propan-2-yl)-1,2,3,4,4a,9,10,10a-octahydrophenanthren-1-yl]methyl}-2,2,2-trifluoroacetamide; and N-tribromoacetylleelamine/GPR-5L/N-{[(1R,4aS)-1,4a-dimethyl-7-(propan-2-yl)-1,2,3,4,4a,9,10,10a-octahydrophenanthren-1-yl]methyl}-2,2,2-tribromoacetamide, are provided according to aspects of the present invention.

Liposomes containing one or more anti-cancer compositions selected from leelamine, a leelamine derivative, abietylamine, an abietylamine derivative and an abietic acid derivative wherein the liposomes containing the one or more anti-cancer compositions are characterized by a neutral surface charge are provided according to aspects of the present invention.

Liposomes containing one or more anti-cancer compositions selected from a leelamine derivative, an abietylamine derivative and an abietic acid derivative of structure (1), (2), (3) or (4), wherein the liposomes containing the one or more anti-cancer compositions are characterized by a neutral surface charge are provided according to aspects of the present invention.

Leelamine-containing liposomes characterized by a neutral surface charge are provided according to aspects of the present invention.

Abietylamine-containing liposomes characterized by a neutral surface charge are provided according to aspects of the present invention.

N-methylabietylamine-containing liposomes characterized by a neutral surface charge are provided according to aspects of the present invention.

N-trifluoroacetylleelamine-containing liposomes characterized by a neutral surface charge are provided according to aspects of the present invention.

N-tribromoacetylleelamine-containing liposomes characterized by a neutral surface charge are provided according to aspects of the present invention.

Methods of treating a subject are provided according to aspects of the present invention which include administering a therapeutically effective amount of a pharmaceutical composition comprising leelamine, a leelamine derivative, abietylamine, an abietylamine derivative, and/or an abietic acid derivative to a subject in need thereof.

Methods of treating a subject are provided according to aspects of the present invention which include administering a therapeutically effective amount of a pharmaceutical composition including one or more leelamine derivatives having the structure:

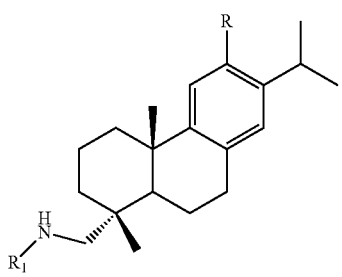

(1)

where R is selected from the group consisting of: H; Br; Cl; F; —COOH; —COOR1; —CONH$_2$; —NH$_2$; —NHR2; —NCS; —NCSe; —NCO; —NHC(O)NHR2; —NHC(S)NHR2; —NHC(Se)NHR2; —NHC(NH)NHR2; $C_1$-$C_5$ straight chain or branched alkyl; $C_6H_5$ unsubstituted aryl; $C_6H_5$ aryl substituted with a substituent selected from: $C_1$-$C_5$ straight chain or branched alkyl, F, Cl, Br, I, and O—$C_1$-$C_5$ where $C_1$-$C_5$ is straight chain or branched alkyl; heteroaryl; and heteromethyl having a heteroatom selected from nitrogen, sulfur and oxygen; where R1 is selected from the group consisting of: $C_1$-$C_5$ straight chain or branched alkyl; trityl; Br$_3$CCO (tribromoacetyl); CH$_3$CO (acetyl); F$_3$CCO (trifluoroacetyl); —COOH; —COOR3; —CONH$_2$; —NH$_2$; —NHR3; —NCS; —NCSe; —NCO; —C(O)NHR3; —C(S)NHR3; —C(Se)NHR3; —C(NH)NHR3; unsubstituted aryl; $C_6H_5$ aryl substituted with a substituent selected from $C_1$-$C_5$ straight chain or branched alkyl, F, Cl, Br, I, and O—$C_1$-$C_5$ where $C_1$-$C_5$ is straight chain or branched alkyl; heteroaryl; heteromethyl; unsubstituted benzyl; benzyl substituted with substituted with a substituent selected from $C_1$-$C_5$ straight chain or branched alkyl, F, Cl, Br, I, —NH2, —CN, —CONH2, —COOH, and O—$C_1$-$C_5$ where $C_1$-$C_5$ is straight chain or branched alkyl; a three to six member saturated heterocycle having at least one nitrogen; heteroaryl-methyl; aroyl; and hetero-aroyl; and where each R2 and R3 is independently selected from the group consisting of: $C_1$-$C_5$ straight chain or branched alkyl; unsubstituted aryl; $C_6H_5$ aryl substituted with a substituent selected from: $C_1$-$C_5$ straight chain or branched alkyl, F, Cl, Br, I, and O—$C_1$-$C_5$ where $C_1$-$C_5$ is straight chain or branched alkyl; a three to six member saturated heterocycle having at least one nitrogen; aroyl; heteroaryl; aralkyl; and heteroaralkyl, to a subject in need thereof.

Methods of treating a subject are provided according to aspects of the present invention which include administering a therapeutically effective amount of a pharmaceutical composition including one or more abietylamine derivatives having the structure:

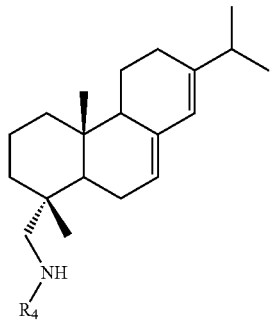

(2)

where R4 is selected from the group consisting of: $C_1$-$C_5$ straight chain or branched alkyl; F, Cl, Br, I, O—$C_1$-$C_5$ where $C_1$-$C_5$ is straight chain or branched alkyl; trityl; Br$_3$CCO (tribromoacetyl); CH$_3$CO (acetyl); F$_3$CCO (trifluoroacetyl); —NH$_2$; —NHR1; —NCS; —NCSe; —NCO; —C(O)NHR1; —C(S)NHR1; —C(Se)NHR1; —C(NH)NHR1; $C_6H_5$ unsubstituted aryl; $C_6H_5$ aryl substituted with a substituent selected from: $C_1$-$C_5$ straight chain or branched alkyl, F, Cl, Br, and I, O—$C_1$-$C_5$ where $C_1$-$C_5$ is straight chain or branched alkyl; heteroaryl, unsubstituted benzyl; benzyl substituted with a substituent selected from $C_1$-$C_5$ straight chain or branched alkyl, F, Cl, Br, I, —NH2, —CN, —CONH2, —COOH, and O—$C_1$-$C_5$ where $C_1$-$C_5$ is straight chain or branched alkyl; heteroaryl-methyl; aroyl; and hetero-aroyl, and where each R1 is independently selected from the group consisting of: $C_1$-$C_5$ straight chain or branched alkyl; $C_6H_5$ unsubstituted aryl; $C_6H_5$ aryl substituted with a substituent selected from: $C_1$-$C_5$ straight chain or branched alkyl, F, Cl, Br, I, and O—$C_1$-$C_5$ where $C_1$-$C_5$ is straight chain or branched alkyl; aroyl, heteroaryl; aralkyl; and heteroaralkyl, to a subject in need thereof.

Methods of treating a subject are provided according to aspects of the present invention which include administering a therapeutically effective amount of a pharmaceutical composition including one or more abietylamine derivatives having the structure:

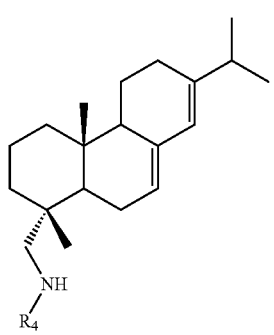

(2)

where R4 is methyl or ethyl, to a subject in need thereof.

Methods of treating a subject are provided according to aspects of the present invention which include administering a therapeutically effective amount of a pharmaceutical composition including one or more abietic acid derivatives having the structure:

(3)

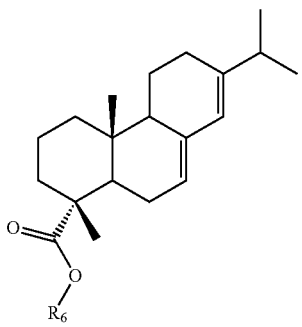

where R6 is selected from the group consisting of: $C_1$-$C_5$ straight chain or branched alkyl; F, Cl, Br, I, O—$C_1$-$C_5$ where $C_1$-$C_5$ is straight chain or branched alkyl, trityl, $Br_3CCO$ (tribromoacetyl), $CH_3CO$ (acetyl), $F_3CCO$ (trifluoroacetyl), $C_6H_5$ unsubstituted aryl; $C_6H_5$ aryl substituted with a substituent selected from $C_1$-$C_5$ straight chain or branched alkyl, F, Cl, Br, I, and O—$C_1$-$C_5$ where $C_1$-$C_5$ is straight chain or branched alkyl, heteroaryl, unsubstituted benzyl; benzyl substituted with a substituent selected from: $C_1$-$C_5$ straight chain or branched alkyl, F, Cl, Br, I, —NH2, —CN, —CONH2, —COOH and O—$C_1$-$C_5$ where $C_1$-$C_5$ is straight chain or branched alkyl; heteroaryl-methyl; aroyl; and heteroaroyl, to a subject in need thereof.

Methods of treating a subject are provided according to aspects of the present invention which include administering a therapeutically effective amount of a pharmaceutical composition including one or more abietic acid derivatives having the structure:

(3)

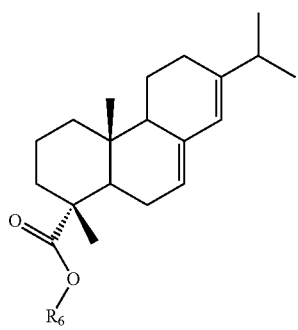

where R6 is methyl or ethyl, to a subject in need thereof.

Methods of treating a subject are provided according to aspects of the present invention which include administering a therapeutically effective amount of a pharmaceutical composition including one or more abietylamine derivatives having structure:

(4)

where R1 and R2 are each independently H, methyl or ethyl, with the proviso that R1 and R2 are not both H, to a subject in need thereof.

Methods of treating a subject are provided according to aspects of the present invention which include administering a therapeutically effective amount of a pharmaceutical composition including one or more anti-cancer compositions selected from the group consisting of: leelamine, abietylamine, abietyl alcohol/GPR-8/[(1R,4aR)-1,4a-dimethyl-7-(propan-2-yl)-1,2,3,4,4a,4b,5,6,10,10a-decahydrophenanthren-1-yl]methanol; abietylamine/GPR-3/{[(1R,4aR)-1,4a-dimethyl-7-(propan-2-yl)-1,2,3,4,4a,4b,5,6,10,10a-decahydrophenanthren-1-yl]methyl}amine; abieticamide/GPR-2/(1R,4aR)-1,4a-dimethyl-7-(propan-2-yl)-1,2,3,4,4a,4b,5,6,10,10a-decahydrophenanthrene-1-carboxamide; N-methylabieticamide/GPR-6/(1R,4aR)—N,1,4a-trimethyl-7-(propan-2-yl)-1,2,3,4,4a,4b,5,6,10,10a-decahydrophenanthrene-1-carboxamide; N-methylabietylamine/GPR-7/{[(1R,4aR)-1,4a-dimethyl-7-(propan-2-yl)-1,2,3,4,4a,4b,5,6,10,10a-decahydrophenanthren-1-yl]methyl}(methyl)amine; N,N-diethylabieticamide/GPR-11/(1R,4aR)—N,N-diethyl-1,4a-dimethyl-7-(propan-2-yl)-1,2,3,4,4a,4b,5,6,10,10a-decahydrophenanthrene-1-carboxamide; N,N-diethylabietylamine/GPR-12/{[(1R,4aR)-1,4a-dimethyl-7-(propan-2-yl)-1,2,3,4,4a,4b,5,6,10,10a-decahydrophenanthren-1-yl]methyl}diethylamine; leelamine/[(1R,4aS)-1,4a-dimethyl-7-(propan-2-yl)-1,2,3,4,4a,9,10,10a-octahydrophenanthren-1-yl]methanamine; N-acetylleelamine/GPR-4L/N-{[(1R,4aS)-1,4a-dimethyl-7-(propan-2-yl)-1,2,3,4,4a,9,10,10a-octahydrophenanthren-1-yl]methyl}acetamide; N-trifluoroacetylleelamine/GPR-1L/N-{[(1R,4aS)-1,4a-dimethyl-7-(propan-2-yl)-1,2,3,4,4a,9,10,10a-octahydrophenanthren-1-yl]methyl}-2,2,2-trifluoroacetamide; N-tribromoacetylleelamine/GPR-5L/N-{[(1R,4aS)-1,4a-dimethyl-7-(propan-2-yl)-1,2,3,4,4a,9,10,10a-octahydrophenanthren-1-yl]methyl}-2,2,2-tribromoacetamide; N-benzoylleelamine/GPR-7L/N-(((1R,4aS)-7-isopropyl-1,4a-dimethyl-1,2,3,4,4a,9,10,10a-octahydrophenanthren-1-yl)methyl)benzamide; and N-benzylleelamine/GPR-8L/N-benzyl-1-((1R,4aS)-7-isopropyl-1,4a-dimethyl-1,2,3,4,4a,9,10,10a-octahydrophenanthren-1-yl)methanamine, to a subject in need thereof.

Methods of treating a subject are provided according to aspects of the present invention which include administering a therapeutically effective amount of an anti-cancer pharmaceutical liposome composition including leelamine, a leelamine derivative, abietylamine, an abietylamine derivative, and/or an abietic acid derivative; and a pharmaceutically acceptable liposome carrier, to a subject in need thereof.

Methods of treating a subject are provided according to aspects of the present invention which include administering a therapeutically effective amount of an anti-cancer pharmaceutical liposome composition including one or more leelamine derivatives having the structure:

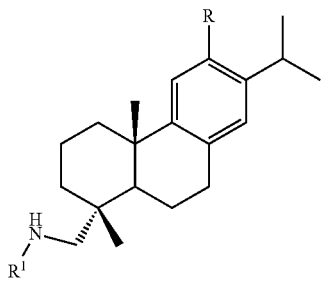

(1)

where R is selected from the group consisting of: H; Br; Cl; F; —COOH; —COOR1; —CONH$_2$; —NH$_2$; —NHR2; —NCS; —NCSe; —NCO; —NHC(O)NHR2; —NHC(S)NHR2; —NHC(Se)NHR2; —NHC(NH)NHR2; C$_1$-C$_5$ straight chain or branched alkyl; C$_6$H$_5$ unsubstituted aryl; C$_6$H$_5$ aryl substituted with a substituent selected from: C$_1$-C$_5$ straight chain or branched alkyl, F, Cl, Br, I, and O—C$_1$-C$_5$ where C$_1$-C$_5$ is straight chain or branched alkyl; heteroaryl; and heteromethyl having a heteroatom selected from nitrogen, sulfur and oxygen; where R1 is selected from the group consisting of: C$_1$-C$_5$ straight chain or branched alkyl; trityl; Br$_3$CCO (tribromoacetyl); CH$_3$CO (acetyl); F$_3$CCO (trifluoroacetyl); —COOH; —COOR3; —CONH$_2$; —NH$_2$; —NHR3; —NCS; —NCSe; —NCO; —C(O)NHR3; —C(S)NHR3; —C(Se)NHR3; —C(NH)NHR3; unsubstituted aryl; C$_6$H$_5$ aryl substituted with a substituent selected from C$_1$-C$_5$ straight chain or branched alkyl, F, Cl, Br, I, and O—C$_1$-C$_5$ where C$_1$-C$_5$ is straight chain or branched alkyl; heteroaryl; heteromethyl; unsubstituted benzyl; benzyl substituted with substituted with a substituent selected from C$_1$-C$_5$ straight chain or branched alkyl, F, Cl, Br, I, —NH2, —CN, —CONH2, —COOH, and O—C$_1$-C$_5$ where C$_1$-C$_5$ is straight chain or branched alkyl; a three to six member saturated heterocycle having at least one nitrogen; heteroaryl-methyl; aroyl; and hetero-aroyl; and where each R2 and R3 is independently selected from the group consisting of: C$_1$-C$_5$ straight chain or branched alkyl; unsubstituted aryl; C$_6$H$_5$ aryl substituted with a substituent selected from: C$_1$-C$_5$ straight chain or branched alkyl, F, Cl, Br, I, and O—C$_1$-C$_5$ where C$_1$-C$_5$ is straight chain or branched alkyl; a three to six member saturated heterocycle having at least one nitrogen; aroyl; heteroaryl; aralkyl; and heteroaralkyl, to a subject in need thereof.

Methods of treating a subject are provided according to aspects of the present invention which include administering a therapeutically effective amount of an anti-cancer pharmaceutical liposome composition including one or more abietylamine derivatives having the structure:

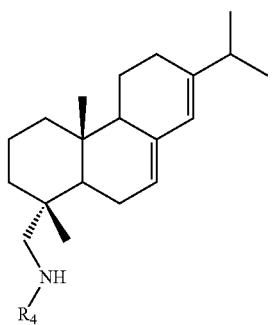

(2)

where R4 is selected from the group consisting of: C$_1$-C$_5$ straight chain or branched alkyl; F, Cl, Br, I, O—C$_1$-C$_5$ where C$_1$-C$_5$ is straight chain or branched alkyl; trityl; Br$_3$CCO (tribromoacetyl); CH$_3$CO (acetyl); F$_3$CCO (trifluoroacetyl); —NH$_2$; —NHR1; —NCS; —NCSe; —NCO; —C(O)NHR1; —C(S)NHR1; —C(Se)NHR1; —C(NH)NHR1; C$_6$H$_5$ unsubstituted aryl; C$_6$H$_5$ aryl substituted with a substituent selected from: C$_1$-C$_5$ straight chain or branched alkyl, F, Cl, Br, and I, O—C$_1$-C$_5$ where C$_1$-C$_5$ is straight chain or branched alkyl; heteroaryl, unsubstituted benzyl; benzyl substituted with a substituent selected from C$_1$-C$_5$ straight chain or branched alkyl, F, Cl, Br, I, —NH2, —CN, —CONH2, —COOH, and O—C$_1$-C$_5$ where C$_1$-C$_5$ is straight chain or branched alkyl; heteroaryl-methyl; aroyl; and hetero-aroyl, and where each R1 is independently selected from the group consisting of: C$_1$-C$_5$ straight chain or branched alkyl; C$_6$H$_5$ unsubstituted aryl; C$_6$H$_5$ aryl substituted with a substituent selected from: C$_1$-C$_5$ straight chain or branched alkyl, F, Cl, Br, I, and O—C$_1$-C$_5$ where C$_1$-C$_5$ is straight chain or branched alkyl; aroyl, heteroaryl; aralkyl; and heteroaralkyl, to a subject in need thereof.

Methods of treating a subject are provided according to aspects of the present invention which include administering a therapeutically effective amount of an anti-cancer pharmaceutical liposome composition including one or more abietylamine derivatives having the structure:

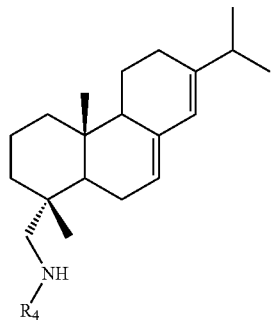

(2)

where R4 is methyl or ethyl, to a subject in need thereof.

Methods of treating a subject are provided according to aspects of the present invention which include administering a therapeutically effective amount of an anti-cancer pharmaceutical liposome composition including one or more abietic acid derivatives having the structure:

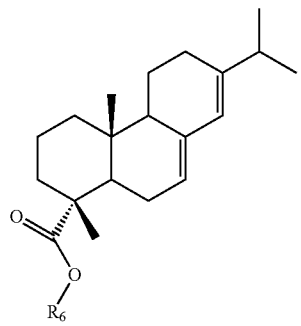

(3)

where R6 is selected from the group consisting of: C$_1$-C$_5$ straight chain or branched alkyl; F, Cl, Br, I, O—C$_1$-C$_5$ where $C_1$-$C_5$ is straight chain or branched alkyl, trityl, $Br_3CCO$ (tribromoacetyl), $CH_3CO$ (acetyl), $F_3CCO$ (trifluoroacetyl), $C_6H_5$ unsubstituted aryl; $C_6H_5$ aryl substituted with a substituent selected from $C_1$-$C_5$ straight chain or branched alkyl, F, Cl, Br, I, and O—$C_1$-$C_5$ where $C_1$-$C_5$ is straight chain or branched alkyl, heteroaryl, unsubstituted benzyl; benzyl substituted with a substituent selected from: $C_1$-$C_5$ straight chain or branched alkyl, F, Cl, Br, I, —NH2, —CN, —CONH2, —COOH and O—$C_1$-$C_5$ where $C_1$-$C_5$ is straight chain or branched alkyl; heteroaryl-methyl; aroyl; and heteroaroyl, to a subject in need thereof.

Methods of treating a subject are provided according to aspects of the present invention which include administering a therapeutically effective amount of an anti-cancer pharmaceutical composition including a pharmaceutically acceptable carrier and one or more abietic acid derivatives having the structure:

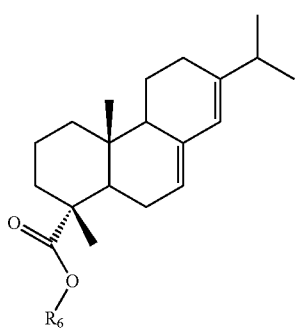

(3)

where R6 is methyl or ethyl, to a subject in need thereof.

Methods of treating a subject are provided according to aspects of the present invention which include administering a therapeutically effective amount of an anti-cancer pharmaceutical liposome composition including one or more abietylamine derivatives having structure:

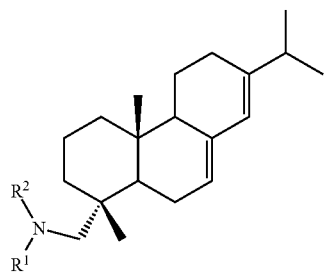

(4)

where R1 and R2 are each independently H, methyl or ethyl, with the proviso that R1 and R2 are not both H, to a subject in need thereof.

Methods of treating a subject are provided according to aspects of the present invention which include administering a therapeutically effective amount of an anti-cancer pharmaceutical liposome composition including one or more anti-cancer compositions selected from the group consisting of: leelamine, abietylamine, abietyl alcohol/GPR-8/[(1R,4aR)-1,4a-dimethyl-7-(propan-2-yl)-1,2,3,4,4a,4b,5,6,10,10a-decahydrophenanthren-1-yl]methanol; abietylamine/GPR-3/{[(1R,4aR)-1,4a-dimethyl-7-(propan-2-yl)-1,2,3,4,4a,4b,5,6,10,10a-decahydrophenanthren-1-yl]methyl}amine; abieticamide/GPR-2/(1R,4aR)-1,4a-dimethyl-7-(propan-2-yl)-1,2,3,4,4a,4b,5,6,10,10a-decahydrophenanthrene-1-carboxamide; N-methylabieticamide/GPR-6/(1R,4aR)—N,1,4a-trimethyl-7-(propan-2-yl)-1,2,3,4,4a,4b,5,6,10,10a-decahydrophenanthrene-1-carboxamide; N-methylabietylamine/GPR-7/{[(1R,4aR)-1,4a-dimethyl-7-(propan-2-yl)-1,2,3,4,4a,4b,5,6,10,10a-decahydrophenanthren-1-yl]methyl}(methyl)amine; N,N-diethylabieticamide/GPR-11/(1R,4aR)—N,N-diethyl-1,4a-dimethyl-7-(propan-2-yl)-1,2,3,4,4a,4b,5,6,10,10a-decahydrophenanthrene-1-carboxamide; N,N-diethylabietylamine/GPR-12/{[(1R,4aR)-1,4a-dimethyl-7-(propan-2-yl)-1,2,3,4,4a,4b,5,6,10,10a-decahydrophenanthren-1-yl]methyl}diethylamine; leelamine/[(1R,4aS)-1,4a-dimethyl-7-(propan-2-yl)-1,2,3,4,4a,9,10,10a-octahydrophenanthren-1-yl]methanamine; N-acetylleelamine/GPR-4L/N-{[(1R,4aS)-1,4a-dimethyl-7-(propan-2-yl)-1,2,3,4,4a,9,10,10a-octahydrophenanthren-1-yl]methyl}acetamide; N-trifluoroacetylleelamine/GPR-1L/N-{[(1R,4aS)-1,4a-dimethyl-7-(propan-2-yl)-1,2,3,4,4a,9,10,10a-octahydrophenanthren-1-yl]methyl}-2,2,2-trifluoroacetamide; N-tribromoacetylleelamine/GPR-5L/N-{[(1R,4aS)-1,4a-dimethyl-7-(propan-2-yl)-1,2,3,4,4a,9,10,10a-octahydrophenanthren-1-yl]methyl}-2,2,2-tribromoacetamide; N-benzoylleelamine/GPR-7L/N-(((1R,4aS)-7-isopropyl-1,4a-dimethyl-1,2,3,4,4a,9,10,10a-octahydrophenanthren-1-yl)methyl)benzamide; and N-benzylleelamine/GPR-8L/N-benzyl-1-((1R,4aS)-7-isopropyl-1,4a-dimethyl-1,2,3,4,4a,9,10,10a-octahydrophenanthren-1-yl)methanamine, to a subject in need thereof.

Methods of treating a subject are provided according to aspects of the present invention which include administering a therapeutically effective amount of an anti-cancer pharmaceutical liposome composition including one or more anti-cancer compositions selected from the group consisting of: leelamine, abietylamine/GPR-3/{[(1R,4aR)-1,4a-dimethyl-7-(propan-2-yl)-1,2,3,4,4a,4b,5,6,10,10a-decahydrophenanthren-1-yl]methyl}amine; N-methylabietylamine/GPR-7/{[(1R,4aR)-1,4a-dimethyl-7-(propan-2-yl)-1,2,3,4,4a,4b,5,6,10,10a-decahydrophenanthren-1-yl]methyl}(methyl)amine; N-trifluoroacetylleelamine/GPR-1L/N-{[(1R,4aS)-1,4a-dimethyl-7-(propan-2-yl)-1,2,3,4,4a,9,10,10a-octahydrophenanthren-1-yl]methyl}-2,2,2-trifluoroacetamide; and N-tribromoacetylleelamine/GPR-5L/N-{[(1R,4aS)-1,4a-dimethyl-7-(propan-2-yl)-1,2,3,4,4a,9,10,10a-octahydrophenanthren-1-yl]methyl}-2,2,2-tribromoacetamide, to a subject in need thereof.

Methods of treating a subject are provided according to aspects of the present invention which include administering a therapeutically effective amount of liposomes containing one or more anti-cancer compositions selected from leelamine, a leelamine derivative, abietylamine, an abietylamine derivative and an abietic acid derivative wherein the liposomes containing the one or more anti-cancer compositions are characterized by a neutral surface charge, to a subject in need thereof.

Methods of treating a subject are provided according to aspects of the present invention which include administering a therapeutically effective amount of liposomes containing one or more anti-cancer compositions selected from a leelamine derivative, an abietylamine derivative and an abietic acid derivative of structure (1), (2), (3) or (4), wherein the liposomes containing the one or more anti-cancer compositions are characterized by a neutral surface charge, to a subject in need thereof.

Methods of treating a subject are provided according to aspects of the present invention which include administering a therapeutically effective amount of leelamine-containing liposomes characterized by a neutral surface charge, to a subject in need thereof.

Methods of treating a subject are provided according to aspects of the present invention which include administering a therapeutically effective amount of abietylamine-containing liposomes characterized by a neutral surface charge, to a subject in need thereof.

Methods of treating a subject are provided according to aspects of the present invention which include administering a therapeutically effective amount of N-methylabietylamine-containing liposomes characterized by a neutral surface charge, to a subject in need thereof.

Methods of treating a subject are provided according to aspects of the present invention which include administering a therapeutically effective amount of N-trifluoro-acetylleelamine-containing liposomes characterized by a neutral surface charge, to a subject in need thereof.

Methods of treating a subject are provided according to aspects of the present invention which include administering a therapeutically effective amount of N-tribromoacetylleelamine-containing liposomes characterized by a neutral surface charge, to a subject in need thereof.

Methods of treating a subject are provided according to aspects of the present invention wherein the subject is human.

Methods of treating a subject are provided according to aspects of the present invention wherein the subject in need thereof has or is at risk of having cancer.

BRIEF DESCRIPTION OF THE DRAWINGS

FIG. 20 shows Table 1 indicating $IC_{50}$ of leelamine against melanoma cells WM35, SBCl-2, WM115, WM278.1, SK<EL-24, 1205 Lu, UACC 903; breast cancer cells MDA-MB-231 and MCF-7; Lung cancer cells A-549; Prostate cancer cells LnCap and PC-3; fibrosarcoma cells HT-1080; pancreatic cancer cells MiaPaca-2; and colon cancer cells HCT-116, HT-29 and SW-480;

FIG. 31 is a table showing results of measurement of blood indicators of toxicity in blood obtained from mice treated with Nanolipolee-007, vehicle (empty liposomes) alone or abietic acid-containing liposomes;

FIG. 45 is a chemical structure illustration and listing of abietic acid derivatives;

FIG. 46 is a chemical structure illustration and listing of leelamine derivatives;

FIG. 47 is a chemical structure illustration and listing of abietylamine derivatives;

FIG. 50 is a scheme for synthesis of compounds described herein;

FIG. 51 is a scheme for synthesis of compounds described herein;

DETAILED DESCRIPTION OF THE INVENTION

Figure 1:
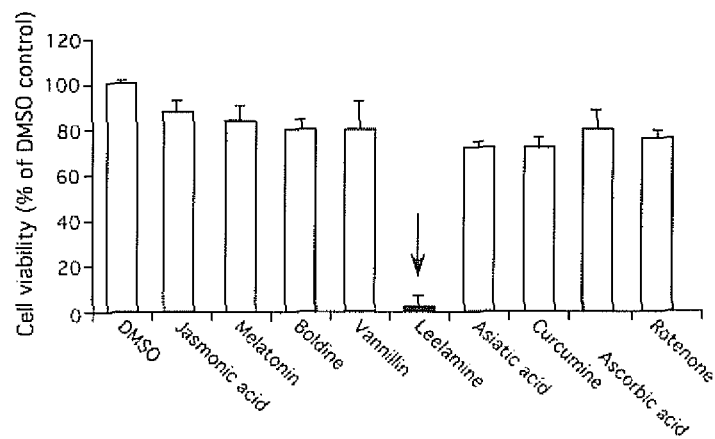
FIG. 1 is a graph illustrating identification of leelamine as an anti-cancer agent.

The singular terms "a," "an," and "the" include plural referents unless the context clearly indicates otherwise.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Chu, E. and Devita, V. T., Eds., Physicians' Cancer Chemotherapy Drug Manual, Jones & Bartlett Publishers, 2005; J. M. Kirkwood et al., Eds., Current Cancer Therapeutics, 4th Ed., Current Medicine Group, 2001; Remington: The Science and Practice of Pharmacy, Lippincott Williams & Wilkins, 21st Ed., 2006; L. V. Allen, Jr. et al., Ansel's Pharmaceutical Dosage Forms and Drug Delivery Systems, 8th Ed., Philadelphia, Pa.: Lippincott, Williams & Wilkins, 2004; and L. Brunton et al., Goodman & Gilman's The Pharmacological Basis of Therapeutics, McGraw-Hill Professional, 11th Ed., 2005.

Compositions and methods for treating cancer are provided according to the present invention.

Compositions and methods for treating cancer are provided according to the present invention which inhibit the PI3K, MAPK and STAT pathways abnormally activated in melanoma and other cancers and inhibit abnormal cell survival and proliferation.

In certain aspects, the present invention relates to compositions including leelamine, a leelamine derivative, abietylamine, an abietylamine derivative, and/or an abietic acid derivative. Methods for treatment and/or prevention of pathological conditions in a subject are provided using leelamine, a leelamine derivative, abietylamine, an abietylamine derivative, and/or an abietic acid derivative. Methods for synthesis of compositions including leelamine, a leelamine derivative, abietylamine, an abietylamine derivative, and/or an abietic acid derivative are provided according to aspects of the present invention.

According to aspects of the present invention, compositions and methods are provided that include a leelamine derivative compound having chemical structure (1):

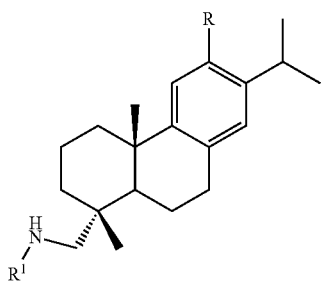

(1)

where R is selected from the group consisting of: H; Br; Cl; F; —COOH; —COOR1; —CONH$_2$; —NH$_2$; —NHR2; —NCS; —NCSe; —NCO; —NHC(O)NHR2; —NHC(S)NHR2; —NHC(Se)NHR2; —NHC(NH)NHR2; C$_1$-C$_5$ straight chain or branched alkyl; C$_6$H$_5$ unsubstituted aryl; C$_6$H$_5$ aryl substituted with a substituent selected from: C$_1$-C$_5$ straight chain or branched alkyl, F, Cl, Br, I, and O—C$_1$-C$_5$ where C$_1$-C$_5$ is straight chain or branched alkyl; heteroaryl; and heteromethyl having a heteroatom selected from nitrogen, sulfur and oxygen; where R1 is selected from the group consisting of: C$_1$-C$_5$ straight chain or branched alkyl; trityl; Br$_3$CCO (tribromoacetyl); CH$_3$CO (acetyl); F$_3$CCO (trifluoroacetyl); —COOH; —COOR3; —CONH$_2$; —NH$_2$; —NHR3; —NCS; —NCSe; —NCO; —C(O)NHR3; —C(S)NHR3; —C(Se)NHR3; —C(NH)NHR3; unsubstituted aryl; C$_6$H$_5$ aryl substituted with a substituent selected from C$_1$-C$_5$ straight chain or branched alkyl, F, Cl, Br, I, and O—C$_1$-C$_5$ where C$_1$-C$_5$ is straight chain or branched alkyl; heteroaryl; heteromethyl; unsubstituted benzyl; benzyl substituted with substituted with a substituent selected from C$_1$-C$_5$ straight chain or branched alkyl, F, Cl, Br, I, —NH2, —CN, —CONH2, —COOH, and O—C$_1$-C$_5$ where C$_1$-C$_5$ is straight chain or branched alkyl; a three to six member saturated heterocycle having at least one nitrogen; heteroaryl-methyl; aroyl; and hetero-aroyl; and where each R2 and R3 is independently selected from the group consisting of: C$_1$-C$_5$ straight chain or branched alkyl; unsubstituted aryl; C$_6$H$_5$ aryl substituted with a substituent selected from: C$_1$-C$_5$ straight chain or branched alkyl, F, Cl, Br, I, and O—C$_1$-C$_5$ where C$_1$-C$_5$ is straight chain or branched alkyl; a three to six member saturated heterocycle having at least one nitrogen; aroyl; heteroaryl; aralkyl; and heteroaralkyl.

According to aspects of the present invention, compositions and methods are provided that include an abietylamine derivative compound having chemical structure (2):

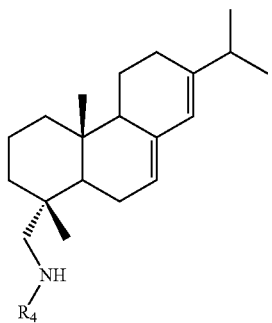

(2)

where R4 is selected from the group consisting of: C$_1$-C$_5$ straight chain or branched alkyl; F, Cl, Br, I, O—C$_1$-C$_5$ where C$_1$-C$_5$ is straight chain or branched alkyl; trityl; Br$_3$CCO (tribromoacetyl); CH$_3$CO (acetyl); F$_3$CCO (trifluoroacetyl); —NH$_2$; —NHR1; —NCS; —NCSe; —NCO; —C(O)NHR1; —C(S)NHR1; —C(Se)NHR1; —C(NH)NHR1; C$_6$H$_5$ unsubstituted aryl; C$_6$H$_5$ aryl substituted with a substituent selected from: C$_1$-C$_5$ straight chain or branched alkyl, F, Cl, Br, and I, O—C$_1$-C$_5$ where C$_1$-C$_5$ is straight chain or branched alkyl; heteroaryl, unsubstituted benzyl; benzyl substituted with a substituent selected from C$_1$-C$_5$ straight chain or branched alkyl, F, Cl, Br, I, —NH2, —CN, —CONH2, —COOH, and O—C$_1$-C$_5$ where C$_1$-C$_5$ is straight chain or branched alkyl; heteroaryl-methyl; aroyl; and hetero-aroyl, and where each R1 is independently selected from the group consisting of: C$_1$-C$_5$ straight chain or branched alkyl; C$_6$H$_5$ unsubstituted aryl; C$_6$H$_5$ aryl substituted with a substituent selected from: C$_1$-C$_5$ straight chain or branched alkyl, F, Cl, Br, I, and O—C$_1$-C$_5$ where C$_1$-C$_5$ is straight chain or branched alkyl; aroyl, heteroaryl; aralkyl; and heteroaralkyl. According to aspects, R4 is methyl or ethyl.

According to aspects of the present invention, compositions and methods are provided that include an abietic acid ester having chemical structure (3):

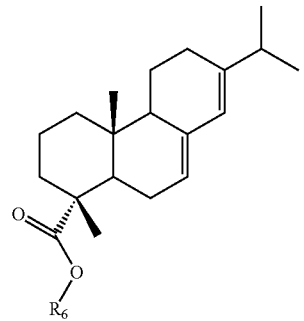

(3)

where R6 is selected from the group consisting of: C$_1$-C$_5$ straight chain or branched alkyl; F, Cl, Br, I, O—C$_1$-C$_5$ where C$_1$-C$_5$ is straight chain or branched alkyl, trityl, Br$_3$CCO (tribromoacetyl), CH$_3$CO (acetyl), F$_3$CCO (trifluoroacetyl), C$_6$H$_5$ unsubstituted aryl; C$_6$H$_5$ aryl substituted with a substituent selected from C$_1$-C$_5$ straight chain or branched alkyl, F, Cl, Br, I, and O—C$_1$-C$_5$ where C$_1$-C$_5$ is straight chain or branched alkyl, heteroaryl, unsubstituted benzyl; benzyl substituted with a substituent selected from: C$_1$-C$_5$ straight chain or branched alkyl, F, Cl, Br, I, —NH2, —CN, —CONH2, —COOH and O—C$_1$-C$_5$ where C$_1$-C$_5$ is straight chain or branched alkyl; heteroaryl-methyl; aroyl; and heteroaroyl.

According to aspects, R6 is methyl or ethyl.

According to aspects of the present invention, compositions and methods are provided that include abietylamine or an abietylamine derivative compound having chemical structure (4):

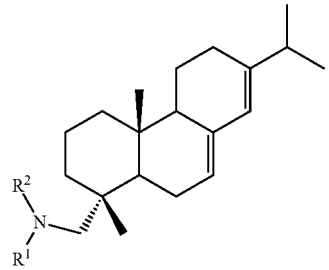

(4)

where R1 and R2 are each H, methyl or ethyl.

According to aspects of the present invention, compositions and methods are provided that include abietylamine/GPR-3{[(1R,4aR)-1,4a-dimethyl-7-(propan-2-yl)-1,2,3,4,4a,4b,5,6,10,10a-decahydrophenanthren-1-yl]methyl}amine; N-methylabietylamine/GPR-7{[(1R,4aR)-1,4a-dimethyl-7-(propan-2-yl)-1,2,3,4,4a,4b,5,6,10,10a-decahydrophenanthren-1-yl]methyl}(methyl)amine; N-trifluoroacetylleelamine/GPR-1L N-{[(1R,4aS)-1,4a-dimethyl-7-(propan-2-yl)-1,2,3,4,4a,9,10,10a-octahydrophenanthren-1-yl]methyl}-2,2,2-trifluoroacetamide; and N-tribromoacetylleelamine/GPR-5L N-{[(1R,4aS)-1,4a-dimethyl-7-(propan-2-yl)-1,2,3,4,4a,9,10,10a-octahydrophenanthren-1-yl]methyl}-2,2,2-tribromoacetamide.

The term "heteroaryl" as used herein refers to a three to six member cyclic system including at least one nitrogen, sulfur or oxygen atom and which may be unsubstituted or substituted with —$NH_2$, —CN, —$CONH_2$, —COOH, $C_1$-$C_5$ straight chain or branched alkyl, F, Cl, Br, I, and/or O—$C_1$-$C_5$ alkyl.

The term "C1-C5 alkyl" as used herein refers to methyl, ethyl, propyl, isopropyl, cyclopropyl, butyl, isobutyl, tert-butyl, cyclobutyl, n-pentane, isopentane, cyclopentane and neopentane.

The term "aralkyl" refers to a $C_1$-$C_3$ straight chain or branched alkyl substituted with $C_6H_5$ aryl where the aryl may be unsubstituted or substituted with $C_1$-$C_5$ straight chain or branched alkyl, F, Cl, Br, I, and/or O—$C_1$-$C_5$ alkyl.

The term "heteroaralkyl" refers to a $C_1$-$C_3$ straight chain or branched alkyl substituted with a three to six member cyclic system including at least one nitrogen, sulfur or oxygen atom where the heterocycle may be unsubstituted or substituted with $C_1$-$C_5$ straight chain or branched alkyl, F, Cl, Br, I, and/or O—$C_1$-$C_5$ alkyl.

The term "heteroaroyl" refers to a three to six member cyclic system including at least one nitrogen, sulfur or oxygen atom where the heterocycle may be unsubstituted or substituted with $C_1$-$C_5$ straight chain or branched alkyl, F, Cl, Br, I, —NH2, —CN, —CONH2, —COOH and/or O—$C_1$-$C_5$ alkyl, where the cyclic system includes at least one nitrogen, sulfur or oxygen atom and where the cyclic system is attached to a molecule by a —C(O)—, such as heteroaryl-C—(O)—.

According to aspects of the present invention, anti-cancer compositions and methods are provided which include a leelamine derivative, an abietylamine derivative, and/or an abietic acid derivative of structures (1), (2), (3) or (4) characterized by pKa in the range of 6-11, inclusive.

Compositions of leelamine, a leelamine derivative, abietylamine, an abietylamine derivative, and/or an abietic acid derivative may be provided as a salt, stereoisomer, hydrate, amide or ester of compounds shown or described herein according to aspects of the present invention.

As used herein, the term "anti-cancer composition" refers to leelamine, a leelamine derivative, abietylamine, an abietylamine derivative, and/or an abietic acid derivative that kills cancer cells or inhibits the growth or proliferation of cancer cells in vitro or in vivo while having less effect on non-cancer cells. Anti-cancer compositions of the present invention exhibit little, if any, toxicity to host cells or non-cancer cells. Anti-cancer compositions inhibit the PI3K, MAPK and STAT pathways abnormally activated in melanoma and other cancers and inhibit abnormal cell survival and proliferation.

The term "derivative" as used herein refers to a compound that is modified compared to a first compound and which has similar or improved bioactivity compared to the first compound.

Compositions including mixtures of two or more of compounds selected from leelamine, a leelamine derivative, abietylamine, an abietylamine derivative, and/or an abietic acid derivative are also specifically contemplated and are considered to be within the scope of the present invention.

Compositions according to the present invention encompass stereoisomers of chemical structures shown and/or described herein. Compositions according to the present invention encompass the individual enantiomers of the compounds having chemical structures shown and/or described herein, as well as wholly or partially racemic mixtures of any of these.

Compositions according to aspects of the present invention prevent and inhibit cancer cell multiplication and tumor development and are considered useful as chemotherapeutic and chemopreventive agents.

It is appreciated that compositions and methods according to aspects described herein are useful to inhibit cancer cells in vitro and in vivo.

Methods and compositions including leelamine, a leelamine derivative, abietylamine, an abietylamine derivative, and/or an abietic acid derivative are provided according to the present invention for treating cancer.

Methods and compositions including abietylamine/GPR-3{[(1R,4aR)-1,4a-dimethyl-7-(propan-2-yl)-1,2,3,4,4a,4b,5,6,10,10a-decahydrophenanthren-1-yl]methyl}amine; N-methylabietylamine/GPR-7{[(1R,4aR)-1,4a-dimethyl-7-(propan-2-yl)-1,2,3,4,4a,4b,5,6,10,10a-decahydrophenanthren-1-yl]methyl}(methyl)amine; N-trifluoroacetylleelamine/GPR-1L N-{[(1R,4aS)-1,4a-dimethyl-7-(propan-2-yl)-1,2,3,4,4a,9,10,10a-octahydrophenanthren-1-yl]methyl}-2,2,2-trifluoroacetamide; and/or N-tribromoacetylleelamine/GPR-5L N-{[(1R,4aS)-1,4a-dimethyl-7-(propan-2-yl)-1,2,3,4,4a,9,10,10a-octahydrophenanthren-1-yl]methyl}-2,2,2-tribromoacetamide are provided according to the present invention for treating cancer.

Particular cancers treated using methods and compositions described herein are characterized by abnormal cell proliferation including, but not limited to, pre-neoplastic hyperproliferation, cancer in-situ, neoplasms and metastasis. Methods and compositions of the present invention can be used for prophylaxis as well as amelioration of signs and/or symptoms of cancer. The terms "treating" and "treatment" used to refer to treatment of a cancer in a subject include: preventing, inhibiting or ameliorating the cancer in the subject, such as slowing progression of the cancer and/or reducing or ameliorating a sign or symptom of the cancer.

A therapeutically effective amount of a composition including an anti-cancer composition of the present invention is an amount which has a beneficial effect in a subject being treated. In subjects having cancer or at risk for having cancer, such as a condition characterized by abnormal cell proliferation including, but not limited to, pre-neoplastic hyperproliferation, cancer in-situ, neoplasms, metastasis, a tumor, a benign growth or other condition responsive to an inventive composition, a therapeutically effective amount of a composition is effective to ameliorate or prevent one or more signs and/or symptoms of the condition. For example, a therapeutically effective amount of a composition is effective to detectably increase apoptosis and/or decrease proliferation of cells of a cancer condition characterized by abnormal cell proliferation including, but not limited to, pre-neoplastic hyperproliferation, cancer in-situ, neoplasms, metastasis, a tumor, a benign growth or other condition responsive to an inventive composition.

Methods of treating a subject are provided according to aspects of the present invention which include administering a therapeutically effective amount of a composition including leelamine, a leelamine derivative, abietylamine, an abietylamine derivative, and/or an abietic acid derivative to a subject in need thereof, wherein the subject has an abnormal proliferative condition, such as cancer, pre-neoplastic hyperproliferation, cancer in-situ, neoplasms, metastasis, tumor or benign growth.

Methods of treating a subject are provided according to aspects of the present invention which include administering a therapeutically effective amount of a composition including abietylamine/GPR-3{[(1R,4aR)-1,4a-dimethyl-7-(propan-2-yl)-1,2,3,4,4a,4b,5,6,10,10a-decahydrophenanthren-1-yl]methyl}amine; N-methylabietylamine/GPR-7{[(1R,4aR)-1,4a-dimethyl-7-(propan-2-yl)-1,2,3,4,4a,4b,5,6,10,10a-decahydrophenanthren-1-yl]methyl}(methyl)amine; N-trifluoroacetylleelamine/GPR-1L N-{[(1R,4aS)-1,4a-dimethyl-7-(propan-2-yl)-1,2,3,4,4a,9,10,10a-octahydrophenanthren-1-yl]methyl}-2,2,2-trifluoroacetamide; and/or N-tribromoacetylleelamine/GPR-5L N-{[(1R,4aS)-1,4a-dimethyl-7-(propan-2-yl)-1,2,3,4,4a,9,10,10a-octahydrophenanthren-1-yl]methyl}-2,2,2-tribromoacetamide to a subject in need thereof, wherein the subject has an abnormal proliferative condition, such as cancer, pre-neoplastic hyperproliferation, cancer in-situ, neoplasms, metastasis, tumor or benign growth.

Subjects are identified as having, or at risk of having, cancer using well-known medical and diagnostic techniques.

In particular aspects, cancers treated in a subject using methods and compositions described herein are characterized by abnormal activation of PI3K, STAT and MAPK.

Increased levels or activity of one or more of PI3K, STAT and MAPK is determined, for instance, by measurement of gene copy number, protein or RNA levels in cells known or suspected to be dysplasic, pre-cancerous, cancerous, metastatic or otherwise characterized by abnormal cell proliferation compared to normal cells. Assays for abnormal activation of PI3K, STAT and MAPK include, but are not limited to phosphorylation assays, immunoassays and nucleic acid assays.

Methods including administration of one or more of leelamine, a leelamine derivative, abietylamine, an abietylamine derivative, and/or an abietic acid derivative to a subject in need thereof are provided according to particular aspects of the present invention which have utility, for example, in inhibiting cancer cells.

Compositions including leelamine, a leelamine derivative, abietylamine, an abietylamine derivative, and/or an abietic acid derivative according to aspects of the present invention have utility in treatment of a subject having cancer or at risk of having cancer, such as in melanoma and other cancers including, but not limited to, cancers of the liver, prostate, breast, brain, stomach, pancreas, blood cells, uterus, cervix, ovary, lung, colon, connective tissues (sarcomas) and other soft tissues.

Methods of treatment of a subject having, or at risk of having, cancer, are provided according to aspects of the present invention including administration of a pharmaceutically effective amount of neutral liposomes containing one or more anti-cancer compositions such as leelamine, a leelamine derivative, abietylamine, an abietylamine derivative, and/or an abietic acid derivative.

Methods of treatment of a subject having, or at risk of having, cancer, are provided according to aspects of the present invention including administration of a pharmaceutically effective amount of a liposomal formuation of leelamine; abietylamine/GPR-3{[(1R,4aR)-1,4a-dimethyl-7-(propan-2-yl)-1,2,3,4,4a,4b,5,6,10,10a-decahydrophenanthren-1-yl]methyl}amine; N-methylabietylamine/GPR-7{[(1R,4aR)-1,4a-dimethyl-7-(propan-2-yl)-1,2,3,4,4a,4b,5,6,10,10a-decahydrophenanthren-1-yl]methyl}(methyl)amine; N-trifluoroacetylleelamine/GPR-1L N-{[(1R,4aS)-1,4a-dimethyl-7-(propan-2-yl)-1,2,3,4,4a,9,10,10a-octahydrophenanthren-1-yl]methyl}-2,2,2-trifluoroacetamide; and/or N-tribromoacetylleelamine/GPR-5L N-{[(1R,4aS)-1,4a-dimethyl-7-(propan-2-yl)-1,2,3,4,4a,9,10,10a-octahydrophenanthren-1-yl]methyl}-2,2,2-tribromoacetamide to a subject in need thereof, wherein the subject has an abnormal proliferative condition, such as cancer, pre-neoplastic hyperproliferation, cancer in-situ, neoplasms, metastasis, tumor or benign growth.

Pharmaceutical compositions including leelamine, a leelamine derivative, abietylamine, an abietylamine derivative, and/or an abietic acid derivative are provided according to aspects of the present invention.

A pharmaceutical composition includes leelamine, a leelamine derivative, abietylamine, an abietylamine derivative, and/or an abietic acid derivative and a pharmaceutically acceptable carrier in particular aspects of the present invention.

A pharmaceutical composition includes abietylamine/GPR-3{[(1R,4aR)-1,4a-dimethyl-7-(propan-2-yl)-1,2,3,4,4a,4b,5,6,10,10a-decahydrophenanthren-1-yl]methyl}amine; and a pharmaceutically acceptable carrier in particular aspects of the present invention.

A pharmaceutical composition includes N-methylabietylamine/GPR-7{[(1R,4aR)-1,4a-dimethyl-7-(propan-2-yl)-1,2,3,4,4a,4b,5,6,10,10a-decahydrophenanthren-1-yl]methyl}(methyl)amine; and a pharmaceutically acceptable carrier in particular aspects of the present invention.

A pharmaceutical composition includes N-trifluoroacetylleelamine/GPR-1L N-{[(1R,4aS)-1,4a-dimethyl-7-(propan-2-yl)-1,2,3,4,4a,9,10,10a-octahydrophenanthren-1-yl]methyl}-2,2,2-trifluoroacetamide; and a pharmaceutically acceptable carrier in particular aspects of the present invention.

A pharmaceutical composition includes N-tribromoacetylleelamine/GPR-5L N-{[(1R,4aS)-1,4a-dimethyl-7-(propan-2-yl)-1,2,3,4,4a,9,0,10a-octahydrophenanthren-1-yl]methyl}-2,2,2-tribromoacetamide and a pharmaceutically acceptable carrier in particular aspects of the present invention.

A pharmaceutical composition includes leelamine and a pharmaceutically acceptable carrier in particular aspects of the present invention.

The term "pharmaceutically acceptable carrier" refers to a carrier which is substantially non-toxic to a subject to which the composition is administered and which is substantially chemically inert with respect to the active component or components.

A pharmaceutical composition according to the invention generally includes about 0.1-99% of leelamine, a leelamine derivative, abietylamine, an abietylamine derivative, and/or an abietic acid derivative. Combinations of leelamine, a leelamine derivative, abietylamine, an abietylamine derivative, and/or an abietic acid derivative in a pharmaceutical composition are also considered within the scope of the present invention.

Anti-cancer compostions optionally include a lipid-based carrier. The term "lipid-based carrier" refers to macromolecular structures having lipid and/or lipid derivatives as the major constituent.

Lipids included in lipid-based carriers can be naturally-occurring lipids, synthetic lipids or combinations thereof.

A lipid-based carrier is formulated as a liposome for use in compositions, kits and methods according to aspects of the invention. The term "liposome" refers to a bilayer particle of amphipathic lipid molecules enclosing an aqueous interior space. Liposomes are typically produced as small unilamellar vesicles (SUVs), large unilammellar vesicles (LUVs) or multilammellar vesicles (MLVs). An anti-cancer composition of the present invention is associated with liposomes by encapsulation in the aqueous interior space of the liposomes, disposed in the lipid bilayer of the liposomes and/or associated with the liposomes by binding, such as ionic binding or association by van der Waals forces. Thus, anti-cancer composition of the present invention is contained in liposomes when it is encapsulated in the aqueous interior space of the liposomes, disposed in the lipid bilayer of the liposomes and/or associated with the liposomes by binding, such as ionic binding or association by van der Waals forces. Liposomes according to aspects of the invention are generally in the range of about 1 nanometer-1 micron in diameter although they are not limited with regard to size.

Liposomal formulations of anti-cancer compositions according to aspects of the present invention include can include one or more types of neutral, cationic lipid and/or anionic lipid, such that the liposomal formulations have a net neutral surface charge at physiological pH. According to aspects, a PEG-modified lipid is included.

The term cationic lipid refers to any lipid which has a net positive charge at physiological pH. Examples of cationic lipids include, but are not limited to, N-(1-(2,3-dioleyloxy)propyl)-N,N,N-trimethylammonium chloride (DOTMA); 1,2-dioleoyloxy-3-(trimethylammonium)propane (DOTAP); 1,2-dioleoyl-3-dimethylammonium-propane (DODAP); dioctadecylamidoglycylspermine (DOGS); 1,2-dipalmitoylphosphatidylethanolamidospermine (DPPES); 2,3-dioleyloxy-N-(2-(sperminecarboxamido)ethyl)-N,N-dimethyl-1-propanaminium trifluoroacetate (DOSPA); dimyristoyltrimethylammonium propane (DMTAP); (3-dimyristyloxypropyl)(dimethyl)(hydroxyethyl)ammonium (DMRIE); dioctadecyldimethylammonium chloride (DODAC), Dimethyldidodecylammonium bromide (DDAB); 3β[N—(N',N'-dimethylaminoethane)-carbamoyl] cholesterol (DC-Chol); 1-[2-(9(Z)-octadecenoyloxy)-ethyl]-2-(8(Z)-heptadecenyl)-3-(2-hydroxyethyl)-imidazolinium (DOTIM); bis-guanidinium-spermidine-cholesterol (BGTC); bis-guanidinium-tren-cholesterol (BGTC); 1,3-Dioleoyloxy-2-(6-carboxy-spermyl)-propylamid (DOSPER) N-[3-[2-(1,3-dioleoyloxy)propoxy-carbonyl]propyl]-N,N,N-trimethylammonium iodide (YKS-220); as well as pharmaceutically acceptable salts and mixtures thereof. Additional examples of cationic lipids are described in Lasic and Papahadjopoulos, Medical Applications of Liposomes, Elsevier, 1998; U.S. Pat. Nos. 4,897,355; 5,208,036; 5,264,618; 5,279,833; 5,283,185; 5,334,761; 5,459,127; 5,736,392; 5,753,613; 5,785,992; 6,376,248; 6,586,410; 6,733,777; and 7,145,039.

The term neutral lipid refers to any lipid which has no net charge, either uncharged or in neutral charge zwitterionic form, at physiological pH. Examples of neutral lipids include, but are not limited to, L-alpha-phosphatidylcholine (ePC), distearoylphosphatidylcholine (DSPC), dioleoylphosphatidylethanolamine (DOPE), distearoylphosphatidylethanolamine (DSPE); 1,2-dioleoyl-sn-glycero-3-Phosphocholine (DOPC), 1,2-dipalmitoyl-sn-glycero-3-phosphoethanolamine (DPPE), cephalin, ceramide, cerebrosides, cholesterol, diacylglycerols, and sphingomyelin.

The term anionic lipid refers to any lipid which has a net negative charge at physiological pH. Examples of anionic lipids include, but are not limited to, dihexadecylphosphate (DhP), phosphatidyl inositols, phosphatidyl serines, such as dimyristoyl phosphatidyl serine, and dipalmitoyl phosphatidyl serine, phosphatidyl glycerols, such as dimyristoylphosphatidyl glycerol, dioleoylphosphatidyl glycerol, dilauryloylphosphatidyl glycerol, dipalmitoylphosphatidyl glycerol, distearyloylphosphatidyl glycerol, phosphatidic acids, such as dimyristoyl phosphatic acid and dipalmitoyl phosphatic acid and diphosphatidyl glycerol.

The term "modified lipid" refers to lipids modified to aid in, for example, inhibiting aggregation and/or precipitation, inhibiting immune response and/or improving half-life in circulation in vivo. Modified lipids include, but are not limited to, pegylated lipids, such as polyethyleneglycol 2000 distearoylphosphatidylethanolamine (PEG(2000) DSPE); 1,2-dipalmitoyl-sn-glycero-3-phosphoethanolamine-N-[methoxy(polyethylene glycol)-2000] (DPPE-PEG-2000), and polyethyleneglycol 750 octadecylsphingosine (PEG (750) C8). Exemplary ratios of components included in liposomal formulations of the present invention are neutral lipid:polyethyleneglycol modified neutral lipid—80:20 mol %.

For example, liposomal formulations include L-alpha-phosphatidylcholine and 1,2-dipalmitoyl-sn-glycero-3-phosphoethanolamine-N-[methoxy(polyethylene glycol)-2000] in an 80:20 mol % ratio according to aspects of the present invention.

Thus, according to aspects, liposomal formulations of anti-cancer compositions include at least one polyethylene glycol modified neutral lipid, wherein the total amount of polyethylene glycol modified neutral lipid is an amount in the range of 10-30 molar percent, inclusive, such as 15-25 molar percent polyethylene glycol modified neutral lipid and further including anionic, cationic or neutral lipids, with the proviso that the resulting liposomes have a net neutral surface charge at physiological pH.

In addition to containing one or more anti-cancer compositions of the present invention, liposomes of the present invention optionally contain any of a variety of useful biologically active molecules and substances including, but not limited to, adjunct therapeutics, proteins, peptides, carbohydrates, oligosaccharides, drugs, and nucleic acids capable of being complexed with the liposomes. The term "biologically active molecules and substances" refers molecules or substances that exert a biological effect in vitro and/or in vivo, such as, but not limited to, nucleic acids, inhibitory RNA, siRNA, shRNA, ribozymes, antisense nucleic acids, antibodies, hormones, small molecules, aptamers, decoy molecules and toxins.

Liposomes are generated using well-known standard methods, including, but not limited to, solvent/hydration methods, ethanol or ether injection methods, freeze/thaw methods, sonication methods, reverse-phase evaporation methods, and surfactant methods. Liposomes and methods relating to their preparation and use are found in Liposomes: A Practical Approach (The Practical Approach Series, 264), V. P. Torchilin and V. Weissig (Eds.), Oxford University Press; 2nd ed., 2003; N. Duzgunes, Liposomes, Part A, Volume 367 (Methods in Enzymology) Academic Press; 1st ed., 2003; L. V. Allen, Jr. et al., Ansel's Pharmaceutical Dosage Forms and Drug Delivery Systems, 8th Ed., Philadelphia, Pa.: Lippincott, Williams & Wilkins, 2005, pp. 663-666; and A. R. Gennaro, Remington: The Science and Practice of Pharmacy, Lippincott Williams & Wilkins, 21st ed., 2005, pp. 766-767.

A pharmaceutical composition includes a liposomal formulation of abietylamine/GPR-3{[(1R,4aR)-1,4a-dimethyl-7-(propan-2-yl)-1,2,3,4,4a,4b,5,6,10,10a-decahydrophenanthren-1-yl]methyl}amine in particular aspects of the present invention.

A pharmaceutical composition includes a liposomal formulation of N-methylabietylamine/GPR-7{[(1R,4aR)-1,4a- dimethyl-7-(propan-2-yl)-1,2,3,4,4a,4b,5,6,10,10a-decahydrophenanthren-1-yl]methyl}(methyl)amine in particular aspects of the present invention.

A pharmaceutical composition includes a liposomal formulation of N-trifluoroacetylleelamine/GPR-1L N-{[(1R, 4aS)-1,4a-dimethyl-7-(propan-2-yl)-1,2,3,4,4a,9,10,10a-octahydrophenanthren-1-yl]methyl}-2,2,2-trifluoroacetamide in particular aspects of the present invention.

A pharmaceutical composition includes a liposomal formulation of N-tribromoacetylleelamine/GPR-5L N-{[(1R, 4aS)-1,4a-dimethyl-7-(propan-2-yl)-1,2,3,4,4a,9,10,10a-octahydrophenanthren-1-yl]methyl}-2,2,2-tribromoacetamide in particular aspects of the present invention.

A pharmaceutical composition includes a liposomal formulation of leelamine in particular aspects of the present invention.

Liposomal formulations of anti-cancer compositions of the present invention are injected intravenously and/or applied topically according to aspects of the present invention.

Combination Treatments

Combinations of therapeutic agents are administered according to aspects of the present invention. In some aspects, two or more anti-cancer compositions of the present invention are administered to a subject to treat cancer in a subject in need thereof. In further aspects, at least one anti-cancer composition of the present invention and at least one additional therapeutic agent are administered to a subject to treat cancer in a subject in need thereof. In still further aspects, at least one anti-cancer composition of the present invention and at least two additional therapeutic agents are administered to a subject to treat cancer in a subject in need thereof.

The term "additional therapeutic agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues which is a biologically, physiologically, or pharmacologically active substance (or substances) that acts locally or systemically in a subject.

Additional therapeutic agents included in aspects of methods and compositions of the present invention include, but are not limited to, antibiotics, antivirals, antineoplastic agents, analgesics, antipyretics, antidepressants, antipsychotics, anti-cancer agents, antihistamines, anti-osteoporosis agents, anti-osteonecrosis agents, antiinflammatory agents, anxiolytics, chemotherapeutic agents, diuretics, growth factors, hormones, non-steroidal anti-inflammatory agents, steroids and vasoactive agents.

Combination therapies utilizing one or more anti-cancer compositions of the present invention and one or more additional therapeutic agents may show synergistic effects, e.g., a greater therapeutic effect than would be observed using either the one or more anti-cancer compositions of the present invention or one or more additional therapeutic agents alone as a monotherapy.

According to aspects, combination therapies include: (1) pharmaceutical compositions that include one or more anti-cancer compositions of the present invention in combination with one or more additional therapeutic agents; and (2) co-administration of one or more anti-cancer compositions of the present invention with one or more additional therapeutic agents wherein the one or more anti-cancer compositions of the present invention and the one or more additional therapeutic agents have not been formulated in the same composition. When using separate formulations, the one or more anti-cancer compositions of the present invention may be administered at the same time, intermittent times, staggered times, prior to, subsequent to, or combinations thereof, with reference to the administration of the one or more additional therapeutic agents.

Combination treatments can allow for reduced effective dosage and increased therapeutic index of the one or more anti-cancer compositions of the present invention and the one or more additional therapeutic agents used in methods of the present invention.

Optionally, a method of treating a subject having cancer or at risk of having cancer further includes an adjunct anti-cancer treatment. An adjunct anti-cancer treatment can be administration of an anti-cancer agent.

Anti-cancer agents are described, for example, in Goodman et al., Goodman and Gilman's The Pharmacological Basis of Therapeutics, 8th Ed., Macmillan Publishing Co., 1990.

Anti-cancer agents illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflornithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, fluorocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochloride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin.

An adjunct anti-cancer treatment can be a radiation treatment of a subject or an affected area of a subject's body.

Pharmaceutical compositions suitable for delivery to a subject may be prepared in various forms illustratively including physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants, such as sodium lauryl sulfate. Additional components illustratively including a buffer, a solvent, or a diluent may be included.

Such formulations are administered by a suitable route including parenteral and oral administration. Administration may include systemic or local injection, and particularly intravenous injection.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and substances similar in nature. Prolonged delivery of an injectable pharmaceutical form can be brought about by the use of agents delaying absorption, for example, aluminum monostearate and gelatin.

Solid dosage forms for oral administration include capsules, tablets, pills, powders, and granules. In such solid dosage forms, one or more anti-cancer compounds described herein is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, plant starches such as potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, glycerol monostearate, and glycols (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also include a buffering agent.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include a pharmaceutically acceptable carrier formulated as an emulsion, solution, suspension, syrup, or elixir. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to leelamine, a leelamine derivative, abietylamine, an abietylamine derivative, and/or an abietic acid derivative, may contain suspending agents, as for example, ethoxylated isostearyl alcohols, polyoxyethylene sorbitol and sorbitol esters, microcrystalline cellulose, aluminum metahydroxide, bentonite, agar-agar or tragacanth, or mixtures of these substances, and the like.

In particular aspects, compositions of the present invention are formulated for topical application. In further particular aspects, compositions of the present invention are formulated for topical application and are characterized by less than 10% absorption of an active ingredient in the composition into the system of an individual treated topically. In still further particular aspects, compositions of the present invention are formulated for topical application and are characterized by less than 9%, 8%, 7%, 6%, 5%, 4%, 3%, 2%, 1% absorption of an active ingredient in the composition into the system of an individual treated topically. Absorption into the system of an individual can be measured by any of various methods, particularly assay for the active ingredient, a metabolite and/or a breakdown product of the active ingredient in a sample obtained from an individual treated with the topical formulation. For example, a blood, plasma or serum sample can be assayed for presence of the active ingredient, a metabolite of the active ingredient and/or a breakdown product of the active ingredient.

A topical formulation can be an ointment, lotion, cream or gel in particular aspects. Topical dosage forms such as ointment, lotion, cream or gel bases are described in Remington: The Science and Practice of Pharmacy, $21^{st}$ Ed., Lippincott Williams & Wilkins, 2006, p. 880-882 and p. 886-888; and in Allen, L. V. et al., Ansel's Pharmaceutical Dosage Forms and Drug Delivery Systems, 8th Ed., Lippincott Williams & Wilkins, 2005, p. 277-297.

Pharmaceutically acceptable carriers and formulation of pharmaceutical compositions are known in the art, illustratively including, but not limited to, as described in Remington: The Science and Practice of Pharmacy, $21^{st}$ Ed., Lippincott, Williams & Wilkins, Philadelphia, Pa., 2006; and Allen, L. V. et al., Ansel's Pharmaceutical Dosage Forms and Drug Delivery Systems, $8^{th}$ Ed., Lippincott, Williams & Wilkins, Philadelphia, Pa., 2005.

The term "subject" refers to an individual in need of treatment for a pathological condition responsive to the beneficial effects of compositions of the present invention, particularly cancer, and generally includes mammals and birds, such as, but not limited to, humans, other primates, cats, dogs, cows, horses, rodents, pigs, sheep, goats and poultry.

A pharmaceutical composition according to the present invention is suitable for administration to a subject by a variety of systemic and/or local routes including, but not limited to, intravenous, intramuscular, subcutaneous, intraperitoneal, oral, otic, rectal, vaginal, topical, parenteral, pulmonary, ocular, nasal, intratumoral and mucosal.

An inventive composition may be administered acutely or chronically. For example, a composition as described herein may be administered as a unitary dose or in multiple doses over a relatively limited period of time, such as seconds-hours. In a further embodiment, administration may include multiple doses administered over a period of days-years, such as for chronic treatment of cancer.

A therapeutically effective amount of a pharmaceutical composition according to the present invention will vary depending on the particular pharmaceutical composition used, the severity of the condition to be treated, the species of the subject, the age and sex of the subject and the general physical characteristics of the subject to be treated. One of skill in the art could determine a therapeutically effective amount in view of these and other considerations typical in medical practice. In general it is contemplated that a therapeutically effective amount would be in the range of about 0.001 mg/kg-100 mg/kg body weight, optionally in the range of about 0.01-10 mg/kg, and further optionally in the range of about 0.1-5 mg/kg. Further, dosage may be adjusted depending on whether treatment is to be acute or continuing.

Advantageously, anti-cancer compounds according to aspects of the present invention are formulated to achieve lipid-solubility and/or aqueous-solubility.

In particular aspects, a pharmaceutically acceptable carrier is a particulate carrier such as lipid particles including liposomes, micelles, unilamellar or mulitlamellar vesicles; polymer particles such as hydrogel particles, polyglycolic acid particles or polylactic acid particles; inorganic particles such as calcium phosphate particles such as described in for example U.S. Pat. No. 5,648,097; and inorganic/organic particulate carriers such as described for example in U.S. Pat. No. 6,630,486.

A particulate pharmaceutically acceptable carrier can be selected from among a lipid particle; a polymer particle; an inorganic particle; and an inorganic/organic particle. A mixture of particle types can also be included as a particulate pharmaceutically acceptable carrier.

A particulate carrier is typically formulated such that particles have an average particle size in the range of about 1 nm-10 microns. In particular aspects, a particulate carrier is formulated such that particles have an average particle size in the range of about 1 nm-100 nm.

Commercial Packages

Commercial packages are provided according to aspects of the present invention for treating cancer in a subject in need thereof, including leelamine, abietylamine, a leelamine derivative, and/or an abietylamine derivative, an abietic acid derivative; such as one or more anti-cancer agents of the present invention having the structural formula designated by the number (1), (2), (3), (4) as shown or described herein; or a salt, stereoisomer, hydrate, amide or ester thereof. One or more auxiliary components are optionally included in commercial packages of the present invention, such as a pharmaceutically acceptable carrier exemplified by a buffer, diluent or a reconstituting agent.

A commercial package including a liposomal formulation of leelamine, abietylamine, a leelamine derivative, an abietylamine derivative, and/or an abietic acid derivative; such as one or more anti-cancer agents of the present invention having the structural formula designated by the number (1), (2), (3), (4) as shown or described herein; or a salt, stereoisomer, hydrate, amide or ester thereof.

Aspects of inventive compositions and methods are illustrated in the examples shown and described herein. These examples are provided for illustrative purposes and are not considered limitations on the scope of inventive compositions and methods.

EXAMPLES

Example 1

Cell Line and Cell Culture Conditions

Human fibroblast FF2441 cells, metastatic melanoma cell lines A375M, SK-MEL-24, 1205 Lu and UACC 903 as well as cancer cell lines representing sarcoma (HT-1080), prostate (PC-3, LNCap), breast (MDA-MB-231, MCF-7), pancreatic neoplasia (MiaPaca-2), lung (A-549) and colon (HCT-116, HT-29, SW-480) are maintained in DMEM (Invitrogen, Carlsbad, Calif.) supplemented with 10% FBS (Hyclone, Logan, Utah) in a 5% CO2 atmosphere, humidified 37° C. incubator. Radial (WM35, Sbcl-2) and vertical (WM115, WM278.1) growth phase melanoma cell lines are maintained in Tu 2% medium as described in Quong, R. Y. et al., Melanoma Res, 1994, 4:313-9. Normal human primary FOM103 melanocytes are cultured in melanoblast media as described in Satyamoorthy, K. et al., Melanoma Res, 1997, 7 Suppl 2, S35-42. Passages 2 to 5 human foreskin keratinocyte (HFK) cells are isolated and cultured in EpiLife E-medium as detailed in Tran, M. A. et al., Cancer Res, 2008, 68:7638-49.

Statistical Analysis.

Statistical analysis is performed using Prism 4.0 GraphPad Software. One-way or Two-way Analysis Of Variance (ANOVA) is used for group wise comparisons, followed by the Tukey's or Bonferroni's post hoc tests. For comparison between two groups, t test is used. Results represent at least two to three independent experiments and are shown as averages±S.E.M. Results with a P value less than 0.05 (95% CI) are considered significant.

In Vitro Screens Identify Leelamine as a Potent Anti-Cancer Agent.

Figure 2:
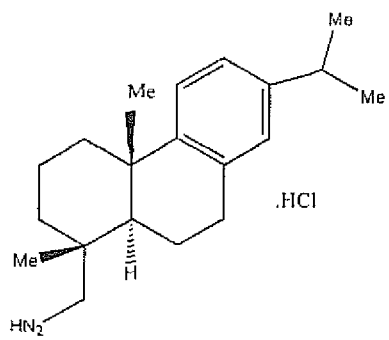
FIG. 2 is a chemical structure illustration of leelamine hydrochloride.

Natural product library NPL-480 (from TimTec Inc., Newark, Del.) consisting of 480 compounds derived from plants, animal, bacteria and fungus is screened using MTS assay to identify agents reducing cell growth of melanoma cells. Compounds of the NPL-480 library that are supplied as powders or oils are dissolved in DMSO to a stock concentration of 10 mM and stored at −20° C. DMSO concentrations in the reaction mixture are controlled to not exceed 0.5% (vol/vol). $5 \times 10^3$ UACC 903 melanoma cells are plated in 96 well plates for 24 hours followed by treatment with each compound at 5 µmol/L for 24 hours. Viability is measured using the MTS assay as described in Sharma, A. et al., Clin Cancer Res, 2009, 15:1674-85; and Madhunapantula, S. V. et al., Mol Cancer Ther, 2008, 7:1297-308. This primary screen identified 12 compounds effective to decrease melanoma cells viability by ~50% or more. Leelamine is found to be the most potent inhibitory compound, decreasing cell viability by ~95% at 5 µmol/L concentration as shown in FIG. 1. FIG. 2 shows the chemical structure of leelamine hydrochloride.

Figure 3:
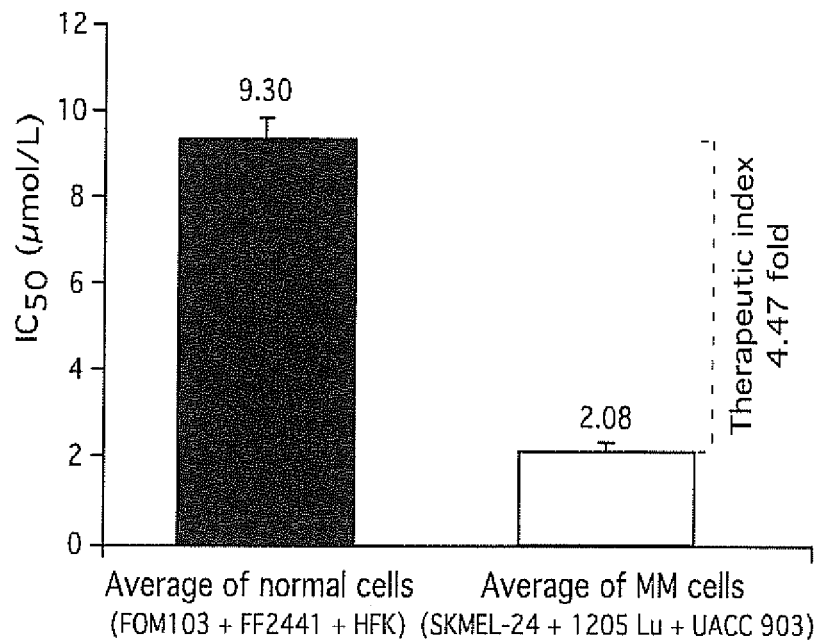
FIG. 3 is a graph showing effects of leelamine on melanoma cells compared to normal cells.

The efficacy of leelamine to kill melanoma cells isolated from various stages of melanoma development is compared to normal cells. Leelamine concentration of 5 to 8 µmol/L is observed to kill 50% of normal cells following 72 hour exposure compared with 1 to 3 µmol/L for cell lines established from melanocytic lesions or melanomas as shown in FIG. 3.

The efficacy of leelamine to kill other cancer types is measured and the $IC_{50}$ for cell lines derived from carcinomas of breast, lung, prostate, connective tissue, pancreas and colon determined. The MTS assay as described in Sharma, A. et al., Clin Cancer Res, 2009, 15:1674-85; and Madhunapantula, S. V. et al., Mol Cancer Ther, 2008, 7:1297-308 is used to establish the $IC_{50}$ at 24, 48 and 72 hours of leelamine treatment for normal human epidermal melanocytes (FOM103), normal skin fibroblast cells (FF2441), normal skin keratinocytes (HFK) and compared to melanocytic lesion cells from the radial-, vertical- and metastatic melanoma stages. $5 \times 10^3$ cells per well in 100 µL of media are plated and grown in a 96-well plate for 48 to 72 hours and treated with either DMSO vehicle control or 0.62 to 40 µmol/L of leelamine for 24, 48 or 72 hours. $IC_{50}$ values for each compound in µmol/L for respective cell lines are measured from three independent experiments using GraphPad Prism version 4.01 (GraphPad Software, La Jolla, Calif.). $IC_{50}$ values of leelamine for non-melanoma cancer cell lines ranged from 1 to 10 µmol/L as shown in Table 1 in FIG. 20. Leelamine is found to be not toxic to normal cells and effective to kill melanoma cells as well as non-melanoma cancer cells as shown in Table 1 in FIG. 20. Leelamine is 3- to 4-fold more specific at killing metastatic melanoma than normal cells, supporting cancer therapeutic utility at concentrations <2 µmol/L.

Cell Viability, Proliferation, Apoptosis and Cell Cycle Analysis.

$5 \times 10^3$ cells per well in 100 µL of media are plated and grown in a 96-well plate for 48 to 72 hours and treated with either DMSO vehicle control or 0.62 to 40 µmol/L of leelamine for 24, 48 or 72 hours. $IC_{50}$ values for each compound in µmol/L for respective cell lines are measured from three independent experiments using GraphPad Prism version 4.01 (GraphPad Software, La Jolla, Calif.).

Leelamine Induces Apoptosis and Decreases Proliferation of Cultured Melanoma Cells.

The mechanistic basis of leelamine's activity to inhibit melanoma cell growth is determined by examining the effect of leelamine on 1) cell viability using the MTS assay; 2) proliferation using a BrdU incorporation assay; 3) apoptosis using an assay for caspase-3/7 activity; and 4) cell cycle analysis. The MTS assay as described in Sharma, A. et al., Clin Cancer Res, 2009, 15: 1674-85; and Madhunapantula, S. V. et al., Mol Cancer Ther, 2008, 7:1297-308 is used to assay cell viability. Rates of proliferation and apoptosis are measured by seeding $5 \times 10^3$ cells in 96-well plates, followed by treatment with 0.62 to 10 µmol/L of leelamine for 24 hours. Proliferating and apoptotic cells are quantified using a colorimetric cell proliferation ELISA BrdU kit (Roche diagnostics, Indianapolis, Ind.) or Apo-ONE Homogenous caspase-3/7 assay kit (Promega, Madison, Wis.), respectively, as described in Sharma, A. et al., Clin Cancer Res, 2009, 15:1674-85; and Madhunapantula, S. V. et al., Mol Cancer Ther, 2008, 7:1297-308.

Figure 4:
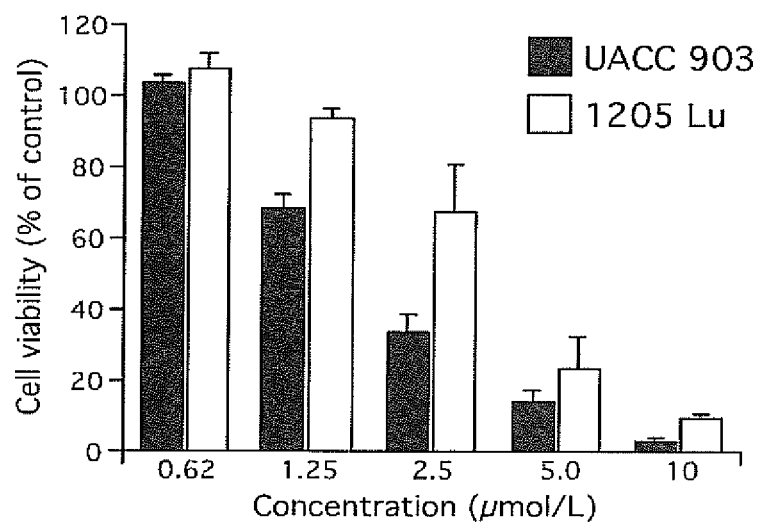
FIG. 4 is a graph showing effects of administration of various concentrations of leelamine on viability of melanoma cells in vitro.
Figure 5:
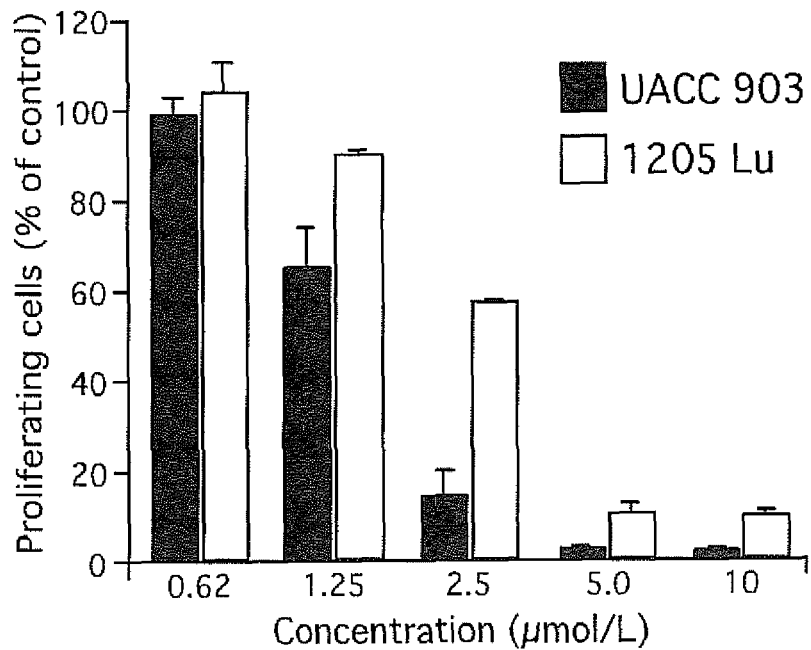
FIG. 5 is a graph showing effects of administration of various concentrations of leelamine on proliferation of melanoma cells in vitro.
Figure 6:
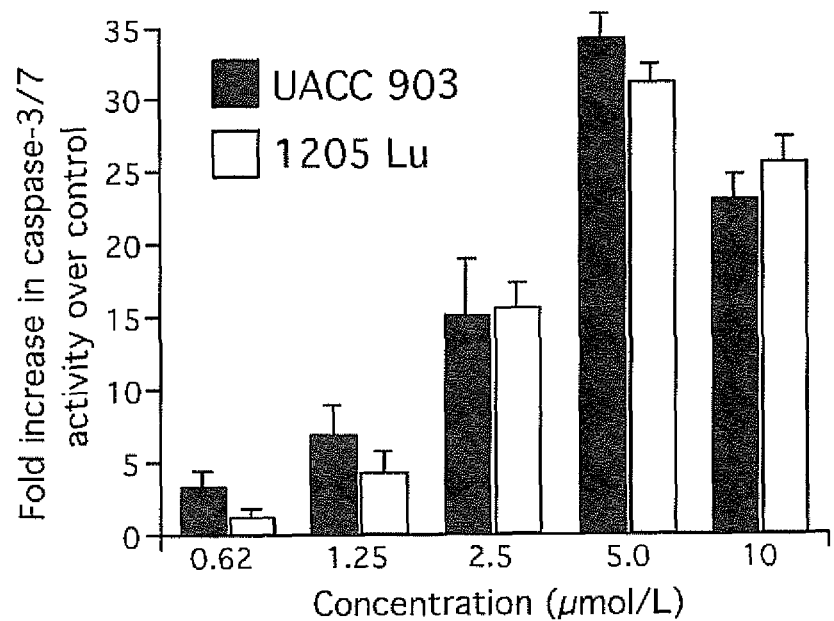
FIG. 6 is a graph showing effects of administration of various concentrations of leelamine on apoptosis of melanoma cells in vitro.

Leelamine effectively inhibits the viability of UACC 903 and 1205 Lu cells in a dose dependent manner. A representative example of the MTS analysis is shown in FIG. 4. Increasing concentrations of leelamine from 0.62 to 10 µmol/L are found to decrease proliferation, shown in FIG. 5, and increase apoptosis of UACC 903 and 1205 Lu cells as shown in FIG. 6. Both cell lines are similarly inhibited following treatment with leelamine.

Analysis of the effects of leelamine on cell cycle is performed by growing UACC 903 and 1205 Lu melanoma cells in 100-mm culture dishes followed by treatment with 2 or 3 µmol/L of leelamine for 24 h. Total floating and adherent cells are collected following trypsinization and stained using 1 mL propidium iodide solution containing 100 µg/mL propidium iodide; (Sigma, St Louis, Mo.), 20 µg/mL Ribonuclease A (Roche diagnostics, Indianapolis, Ind.) and 3 µg/mL Triton X-100 dissolved in 0.1% (W/V) sodium citrate for 30 m at 4° C. Stained cells are analyzed using the FACScan analyzer (Becton Dickinson, Franklin lakes, NJ) and data processed utilizing ModFit LT software (Verity Software House, Topsham, Me.) as described in Sharma, A. et al., Clin Cancer Res, 2009, 15:1674-85; and Madhunapantula, S. V. et al., Mol Cancer Ther, 2008, 7:1297-308.

Figure 7:
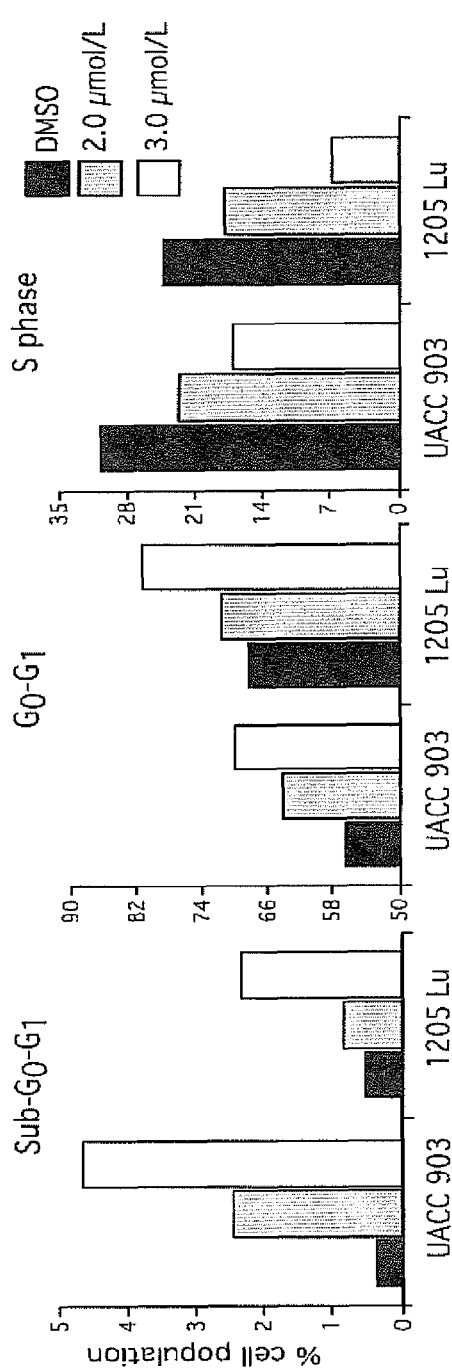
FIG. 7 is a set of graphs showing effects of administration of various concentrations of leelamine on cell cycle of melanoma cells in vitro.

Cell cycle analysis shows increased percentage of sub-G0-G1 and G0/G1 cell populations, with a corresponding decrease in S-phase population (FIG. 7). Thus, leelamine decreases melanoma cell survival by decreasing proliferation and triggering apoptosis mediated through a G0/G1 block resulting in fewer cells in S-phase.

Non-Toxic Leelamine Inhibits Melanoma Tumor Development.

Figure 8:
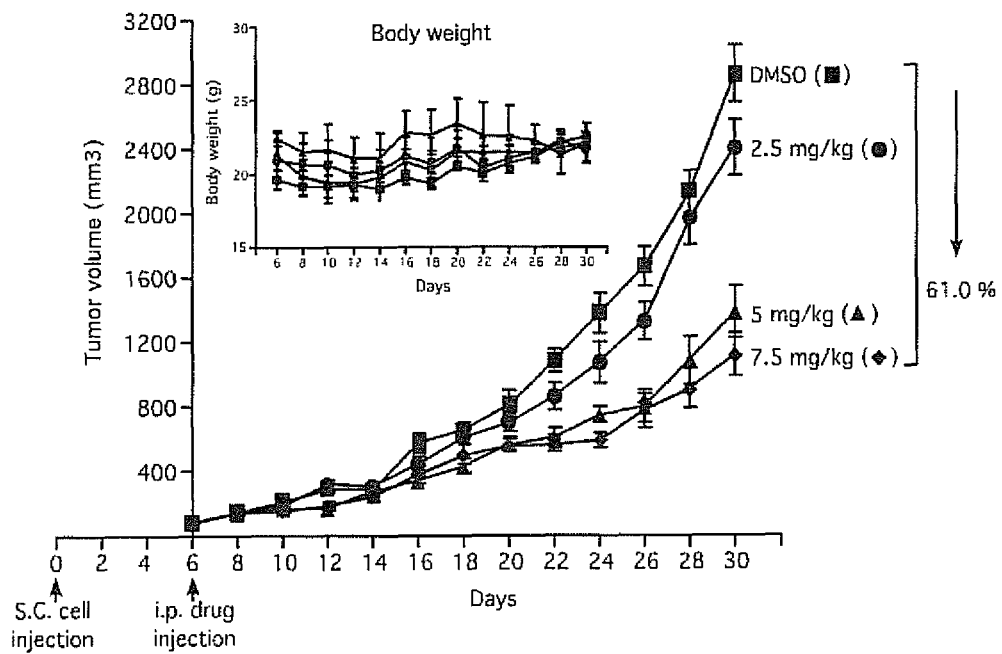
FIG. 8 is a graph showing effects of administration of various concentrations of leelamine on UACC 903 human melanoma cell tumors in mice compared to administration of vehicle (DMSO) alone and an inset graph showing body weight of the same treated mice.
Figure 9:
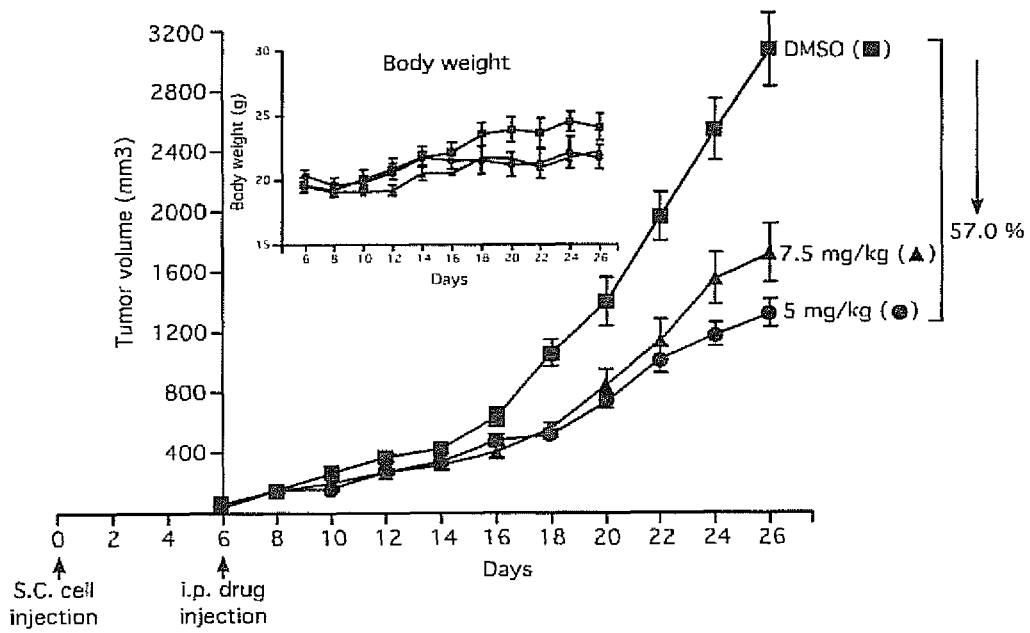
FIG. 9 is a graph showing effects of administration of various concentrations of leelamine on 1205 Lu human melanoma cell tumors in mice compared to administration of vehicle (DMSO) alone and an inset graph showing body weight of the same treated mice.

The efficacy of leelamine for inhibiting melanoma tumor development is evaluated on preexisting tumors formed following subcutaneous injection of cancer cells into nude mice. Tumor kinetics are measured by subcutaneous injection of $1.0 \times 10^6$ UACC 903 or 1205 Lu cells in 0.2 mL of DMEM supplemented with 10% FBS subcutaneously injected above both left and right rib cages of 3- to 4-wk-old female athymic nude-Foxn1$^{nu}$ mice (Harlan Laboratories, Indianapolis, Ind.). Six days later, when a fully vascularized tumor (50-75 mm$^3$) has formed, mice are randomly divided into DMSO vehicle control and experimental groups (5 mice/group; 2 tumors/mouse) and treated intraperitoneally with 2.5-7.5 mg/kg body weight leelamine daily for 3-4 weeks. Body weight (grams) and dimensions of the developing tumors (mm$^3$) are measured at the time of drug treatment as described in Sharma, A. et al., Clin Cancer Res, 2009, 15:1674-85; and Madhunapantula, S. V. et al., Mol Cancer Ther, 2008, 7:1297-308. Leelamine significantly reduces tumor volume, by 61% for UACC 903 as shown in FIG. 8, and by 57% 1205 Lu cells as shown in FIG. 9, compared to DMSO vehicle treated animals. Body weights of mice show no significant differences between leelamine or control groups indicating negligible toxicity, as shown in the inserts in FIGS. 8 and 9.

Toxicity Assessments.

Figure 12:
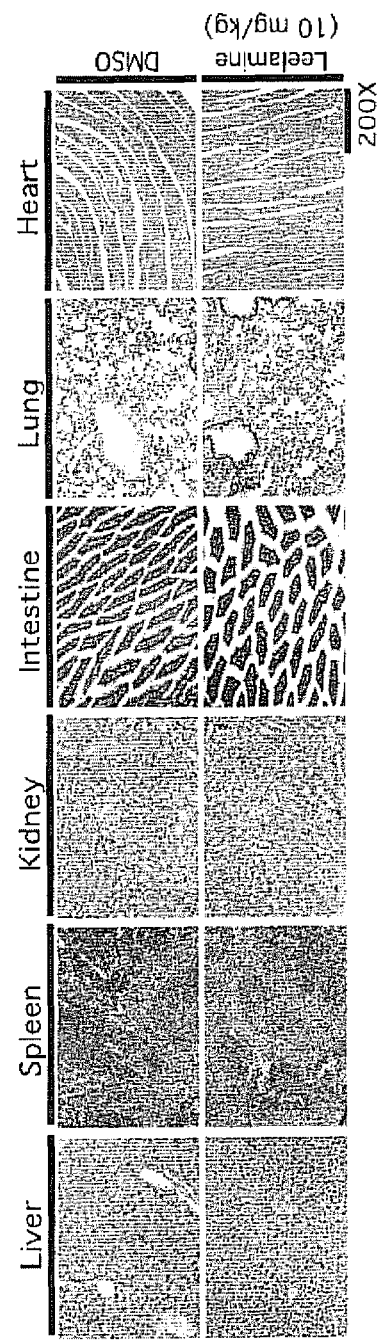
FIG. 12 is a set of images showing hematoxylin/eosin stained tissue sections obtained from mice treated with 10 mg/kg body weight leelamine daily for four weeks compared to mice treated with vehicle (DMSO) alone daily for four weeks.
Figure 10:
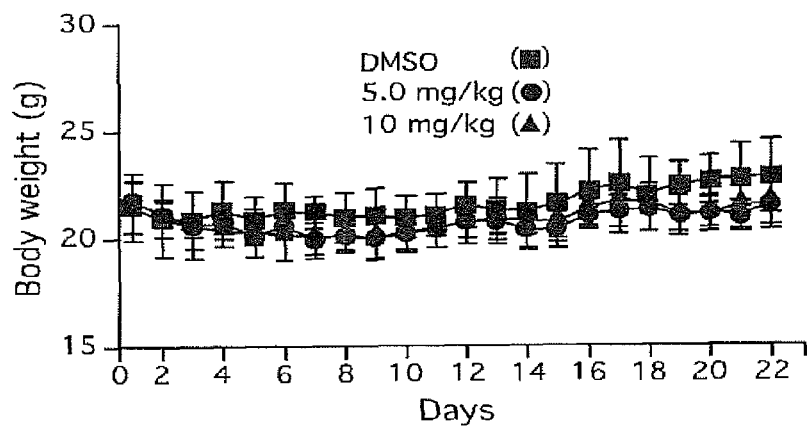
FIG. 10 is a graph showing effects of administration of 5 or 10 mg/kg body weight leelamine daily for four weeks compared to mice treated with vehicle (DMSO) alone daily for four weeks.
Figure 11:
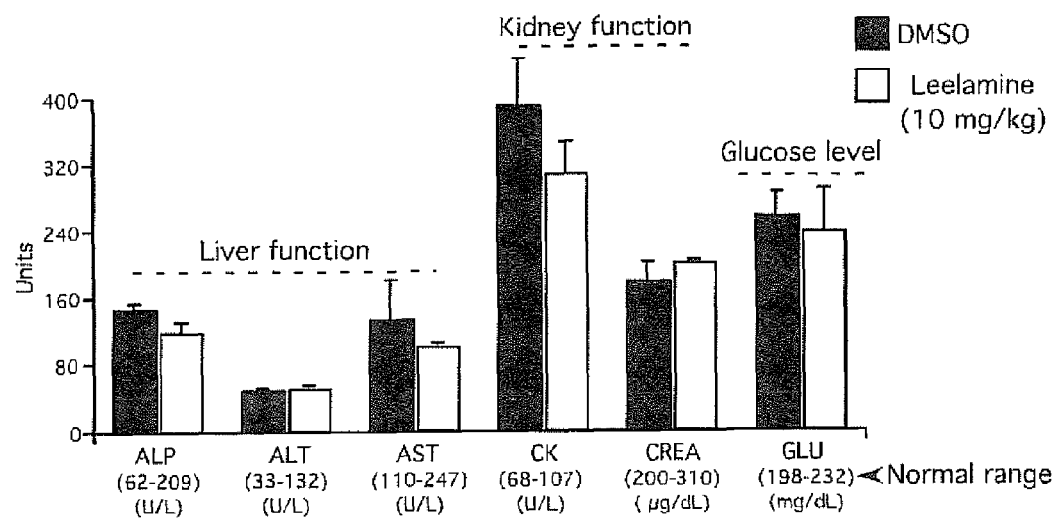
FIG. 11 is a graph showing results of measurement of blood indicators of toxicity in blood obtained from mice treated with 10 mg/kg body weight leelamine daily for four weeks compared to mice treated with vehicle (DMSO) alone daily for four weeks.

To assess toxicity, Swiss Webster (n=5) mice are intraperitoneally injected with 5 or 10 mg/kg body weight leelamine or with vehicle control (DMSO) every day for 4 weeks. Animals are weighed daily to ascertain the toxicity leading to changes in body weight. Body weights of mice show no significant differences between groups indicating negligible toxicity, shown in FIG. 10. Blood is collected by cardiac puncture at the end of treatment and analyzed for the levels of ALP (alkaline phosphatase), ALT (alanine aminotransferase), AST (aspartate aminotransferase), CK (creatine kinase), CREA (creatinine) and GLU (glucose), parameters indicative of organ related toxicity, following systemic administration of 10-mg/Kg-body weight of leelamine, shown in FIG. 11. No significant differences are noticed in any of these parameters between controls or leelamine injected animals. Vital organs including liver, spleen, kidney, intestine, lung and heart from control and experimental animals are collected at the end of the test period, formalin fixed, paraffin-embedded, hematoxylin/eosin stained and analyzed microscopically for changes in cellular morphology or tissue architecture as described in Sharma, A. et al., Clin Cancer Res, 2009, 15:1674-85; and Madhunapantula, S. V. et al., Mol Cancer Ther, 2008, 7:1297-308. Histological examination of hematoxylin/eosin-stained vital organ sections revealed that daily 10-mg/Kg-body weight of leelamine treatment did not significantly alter cell morphology or overall structure of liver, spleen, kidney, intestine, lung or heart, shown in FIG. 12.

Leelamine Inhibits the Activity of Three Pathways Promoting Melanoma Development Pathways targeted by leelamine in melanoma cells to decrease proliferation and trigger apoptosis is identified using a Kinexus Antibody Microarray and Ingenuity Pathway Analysis followed by Western blot confirmation.

A Kinexus Antibody Microarray is used to identify the pathways targeted by leelamine using the protocols provided by the Kinexus company as described in Yamada, R. et al., N. J Med Chem, 54:2902-14; and Cao, X. et al., Curr Cancer Drug Targets, 2009, 9:189-201. In brief, UACC903 cells are treated with 3 µmol/L leelamine for 3-24 hours, lysates collected and processed by Kinexus using 812-antibody microarray analysis. Kinexus 812-antibody microarray results are analyzed using the Ingenuity Pathway Analysis (IPA) software. Significantly up-regulated or down-regulated pan-specific and phosphor proteins with corresponding Swiss-Prot accession numbers and ratio changes are uploaded as an Excel spreadsheet file to the Ingenuity Pathway Analysis server and pathways identified.

Figure 13:
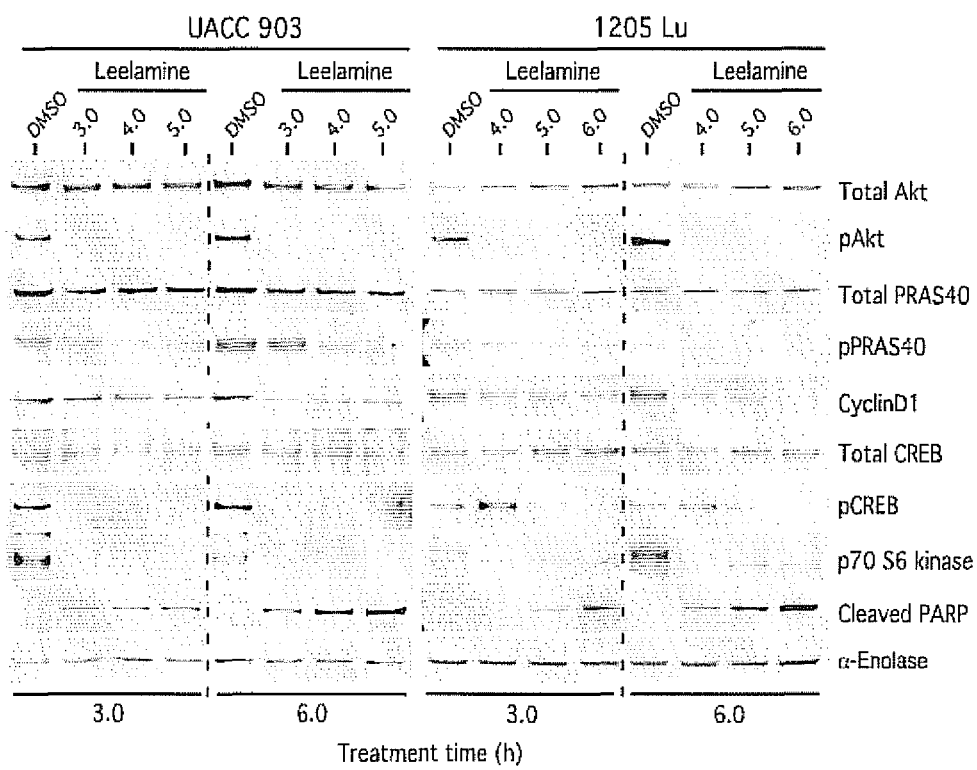
FIG. 13 is an image of a Western blot showing effects of various concentrations of leelamine on PI3K/Akt signaling pathways regulating melanoma development.
Figure 14:
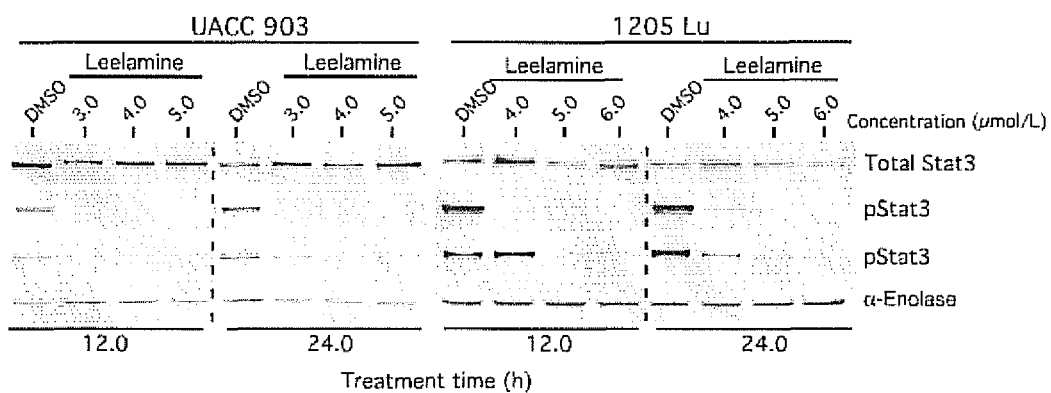
FIG. 14 is an image of a Western blot showing effects of various concentrations of leelamine on STAT signaling pathways regulating melanoma development.
Figure 15:
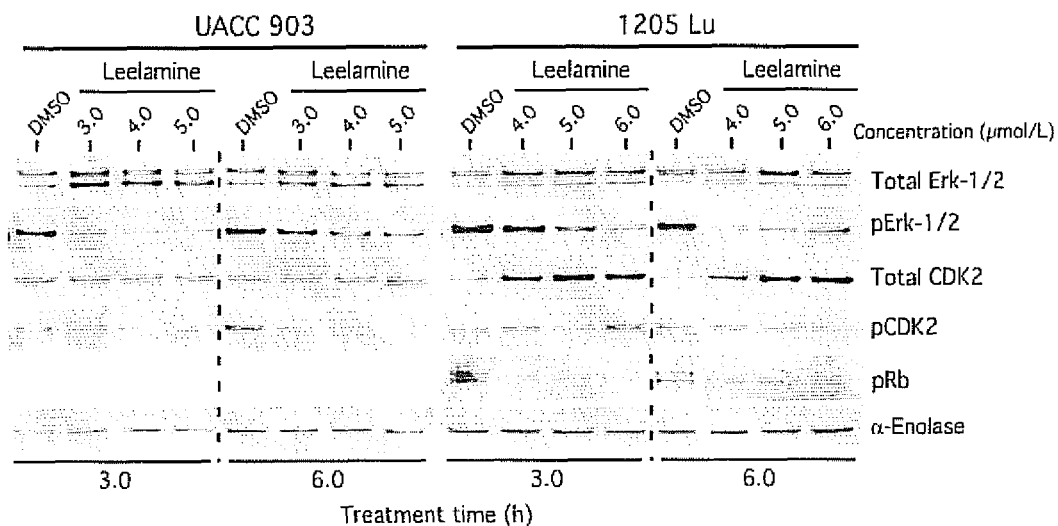
FIG. 15 is an image of a Western blot showing effects of various concentrations of leelamine on MAPK signaling pathways regulating melanoma development.

Leelamine decreases activity of the STAT as well as PI3 and MAP kinases pathways, which are three major signaling pathways promoting melanoma development. Decreased signaling through each pathway following treatment with 3 to 6 µmol/L of leelamine for 3 to 24 hours is shown for PI3 kinase pathway in FIG. 13, STAT pathway in FIG. 14 and MAP kinase pathway in FIG. 15. Similar signaling inhibition is observed for both UACC 903 and 1205 Lu cell lines, with inhibition of PI3 kinase and MAP kinase pathways occurring at 3 to 6 hours while inhibition of the STAT pathway occurs from 12 hours of treatment, FIG. 14.

Leelamine decreased the proliferative potential of melanoma cells leading to increased apoptosis and decreased vascular development.

Rates of cell proliferation (using Ki-67), apoptosis (using terminal deoxynucleotidyl transferase-mediated dUTP nick-end labeling) and tumor angiogenesis (using CD31 staining) are quantified in time and size matched tumors treated with leelamine compared with DMSO treated control animals to identify the underlying mechanism by which leelamine inhibits melanoma tumor development using an established method described in Sharma, A. et al., Clin Cancer Res, 2009, 15:1674-85; Madhunapantula, S. V. et al., Mol Cancer Ther, 2008, 7:1297-308; Sharma, A. et al., Cancer Res, 2006, 66:8200-9; and Stahl, J. M. et al., Cancer Res, 2003, 63:2881-90. Size and time matched tumors at each time are compared to identify the first statistically quantifiable difference(s) affected by leelamine treatment in the rates of processes regulating tumor development i.e. cell proliferation, apoptosis or vascular development. Briefly, the mechanism by which leelamine delays tumor development is established by comparing size and time matched melanoma tumors treated with leelamine compared to DMSO vehicle treated animals. $2.5 \times 10^6$ UACC 903 cells are injected subcutaneously (s.c.) into nude mice, generating tumors of the same size developing at parallel time points. Six days later, mice are treated intraperitoneally (i.p.) with DMSO vehicle or leelamine (7.5 mg/kg body weight) daily up to day 15. Tumors are harvested at 11, 13 and 15 days for comparison of rates of cellular proliferation, apoptosis and vessel density by immunohistochemistry and Western blotting analysis as described in Sharma, A. et al., Cancer Res, 2006, 66:8200-9; and Stahl, J. M. et al., Cancer Res, 2003, 63:2881-90. Cell proliferation is measured using mouse anti-human Ki-67 staining from Pharmigen (San Diego, Calif.). Apoptosis rates are scored using "terminal deoxynucleotidyl transferase-mediated dUTP nick end labeling (TUNEL)" TMR Red Apoptosis kit from Roche (Mannheim, Germany). Vessel density indicative of apoptosis is estimated using a purified rat anti-mouse CD31 (PECAM-1) monoclonal antibody immunostaining (Phanningen). The number of Ki-67 and TUNEL positive cells is quantified as the percentage of total cells in tumors using the IP Lab imaging software program. For CD31, the area occupied by blood vessels is measured. For all tumor analyses, a minimum of 6 different tumors with 4-6 fields per tumor is analyzed and results represented as the average±SEM.

Figure 16:
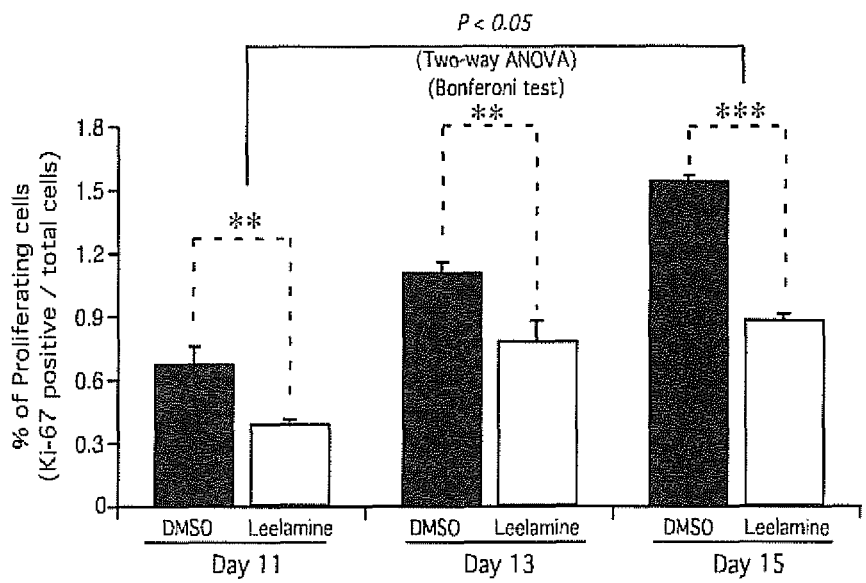
FIG. 16 is a graph showing effects of leelamine or vehicle (DMSO) on proliferating cells using Ki-67 immunostaining in size and time matched tumors.
Figure 17:
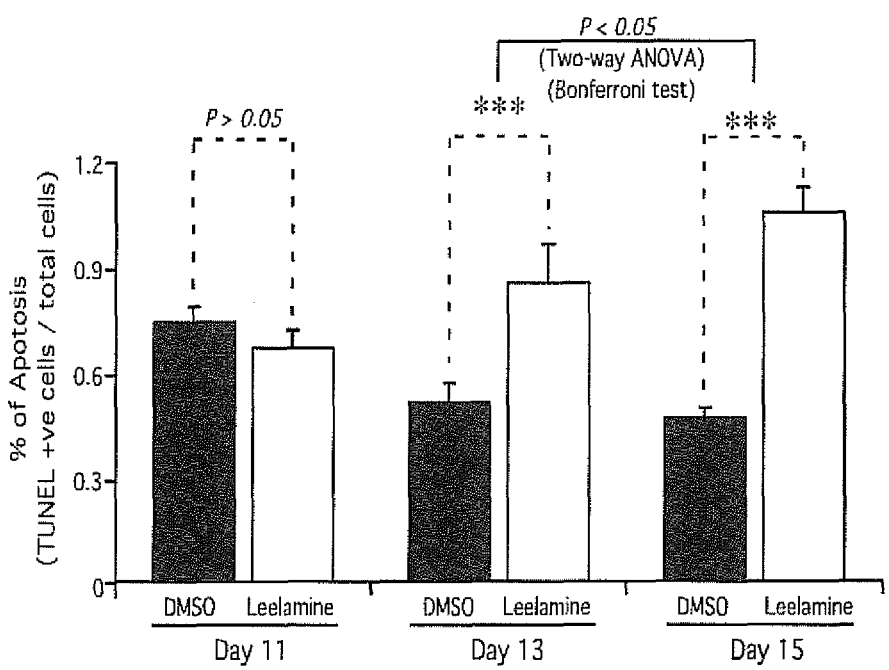
FIG. 17 is a graph showing effects of leelamine or vehicle (DMSO) on apoptosis using TUNEL staining in size and time matched tumors.
Figure 18:
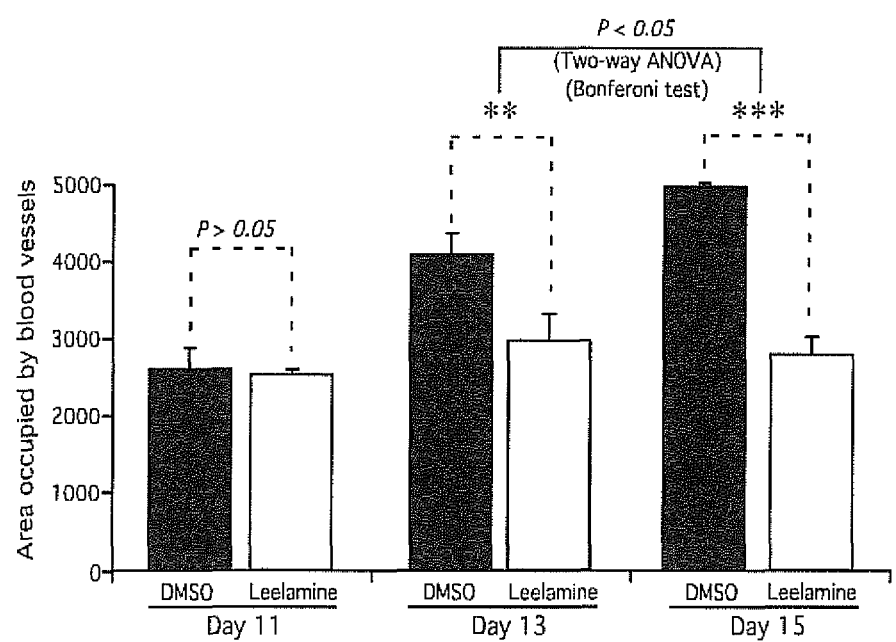
FIG. 18 is a graph showing effects of leelamine or vehicle (DMSO) on vascular development using CD31 immunostaining in size and time matched tumors.

At day 11, a statistically significant 50% reduction in proliferating cells is observed after leelamine treatment but not in cellular apoptosis or vascular development rates compared with DMSO control treated animals as shown in FIG. 16, FIG. 17 and FIG. 18, $sP<0.05$, two-way analysis of variance. Similar significant differences in cellular proliferation, apoptosis and vascular development are detected in all tumors compared with DMSO controls at days 13 and 15, suggesting that lack of proliferation subsequently triggers apoptosis and decreased vascular development as shown in FIG. 16, FIG. 17 and FIG. 18, $P<0.05$, two-way analysis of variance).

Western Blot Analysis.

For Western blot analysis, cell lysates are harvested by addition of RIPA lysis buffers containing 25 mM Tris·HCl pH 7.6, 150 mM NaCl, 1% NP-40, 1% sodium deoxycholate, 0.1% SDS, 10 mM EDTA, 1 mM sodium orthovanadate, 0.1 mM sodium molybdate, 1 mM phenylmethylsulfonyl fluoride, 20 µg/mL aprotinin, and 5 µg/mL leupeptin. The cell lysates are harvested and processed as described in Madhunapantula, S. V. et al., Cancer Res, 2007, 67:3626-36. Treatment conditions: $1-1.5 \times 10^6$ melanoma cells are plated in 100 mm culture dishes, 48 h later, treated with leelamine (3-6 µmol/L) for 3 to 24 hours. Protein lysates are collected for Western blotting. The blots are probed with antibodies according to each supplier's recommendations: antibodies to total Akt, phospho-Akt (Ser473), total PRAS40, phospho-PRAS40 (Thr246), total CREB, phospho-CREB (Ser133), phospho-p70 S6 kinase (Thr389), total Erk1/2, phospho-Erk1/2 (Thr202/Tyr 204), total CDK2, phospho-CDK2 (Thr160), phospho-Rb (Ser807/811), total Stat, phospho-Stat1 (Tyr701), Phospho-Stat-2 (Tyr690), Phospho-Stat3 (Ser727), phospho-Stat3 (Tyr705) and cleaved PARP from Cell Signaling Technology (Danvers, Mass.); total PRAS40 from Invitrogen (Carlsbad, Calif.); cyclin D1, Bcl-2, α-enolase and secondary antibodies conjugated with horseradish peroxidase from Santa Cruz Biotechnology (Santa Cruz, Calif.). Immunoblots are developed using the enhanced chemiluminescence (ECL) detection system (Thermo Fisher Scientific, Rockford, Ill.). Intensity of protein bands is quantified using ImageJ software.

Figure 19:
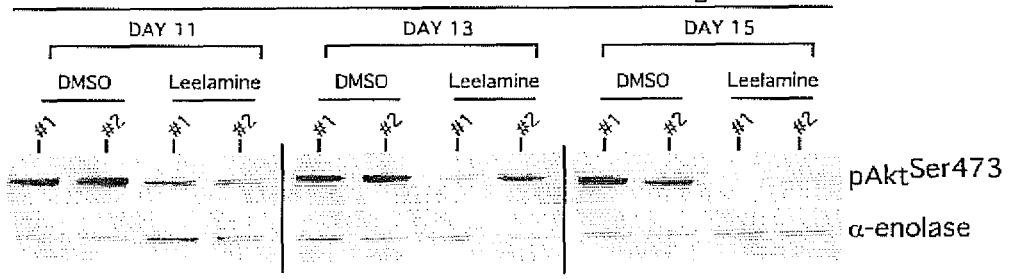
FIG. 19 is an image of a Western blot showing protein expression in UACC 903 xenograft tumors of mice following administration of leelamine or vehicle (DMSO)

Western blot analysis of size and time matched tumors lysates harvested at days 11, 13 and 15 from animals treated from day 6 with leelamine show decreased active pAkt compared with vehicle DMSO control-treated animals indicating the compound is acting on pathways inhibited by leelamine, FIG. 19.

Example 2

Figure 21:
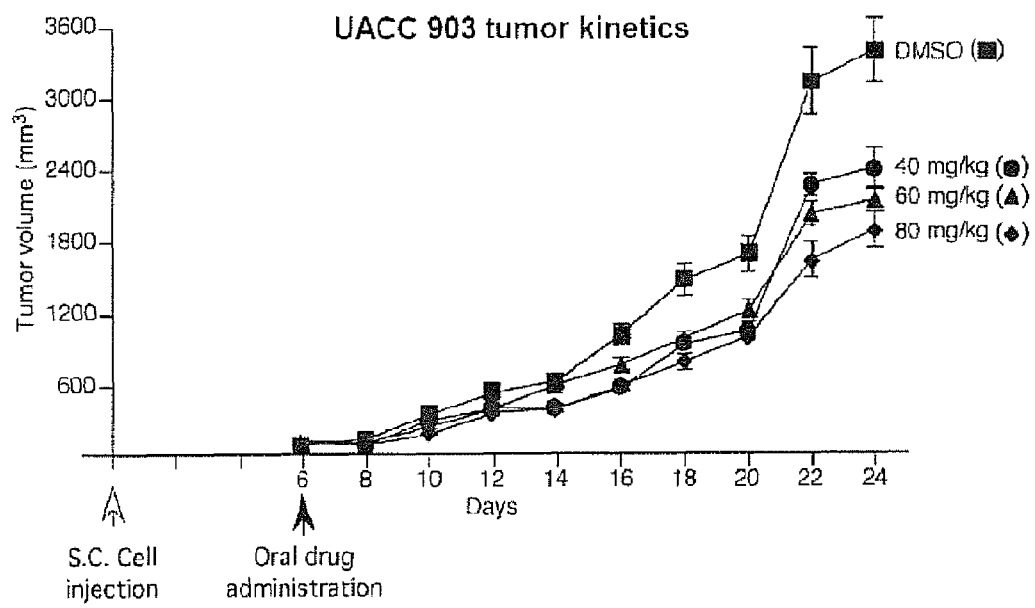
FIG. 21 is a graph showing effects of oral administration of leelamine on UACC 903 tumors in mice.

In this example, leelamine (40, 60, or 80 mg/kg body weight) is administered orally to 4-6 weeks old nude mice bearing UACC903 melanoma cell tumors (50-100 mm³). Sizes of developing tumors are measured. FIG. 21 is a graph showing tumor volume over time and shows that leelamine reduced tumor growth development ~45% compared to DMSO control treated mice. Values±S.E.M. (n=5)

Example 3

Figure 22:
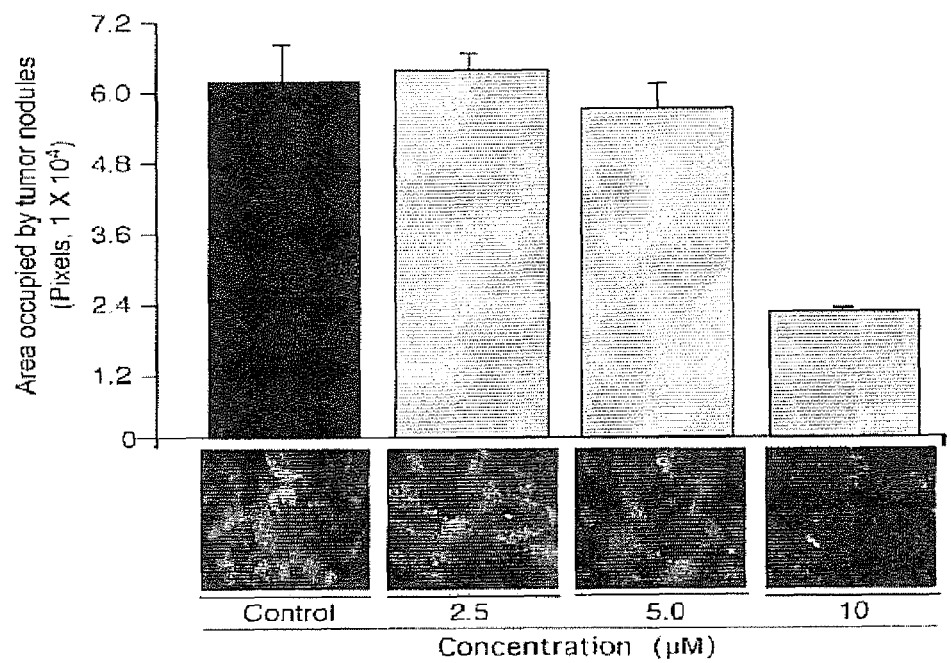
FIG. 22 is a graph showing effect of topical administration of leelamine on melanoma tumors developing in skin reconstructs.

In this example, the effect of leelamine on melanoma tumors developing in skin reconstructs is tested by topical application. Skin reconstructs are generated by mixing GFP expressing UACC 903 melanoma cells with human normal fibroblasts (FF2441) and keratinocytes (HFK) followed by growing in a 37° C. incubator for 7 days. Beginning from day 8, completely developed skins containing melanoma tumors are treated with increasing concentrations of Leelmaine (2.5, 5 and 10 uM in 200 uL PBS) or PBS vehicle alone for an additional 8 more days. The sizes of developing tumors, in terms of area occupied by GFP are measured. FIG. 22 shows a graph of area occupied by tumor nodules; P<0.05, One-way ANOVA) between vehicle PBS control or treated skins. Also shown in FIG. 22 are images of control and treated cells. Results show that topical treatment with leelamine inhibits melanoma tumor growth in artificial skin constructs.

Example 4

Several liposomal formulations are developed to incorporate leelamine or other compounds described herein, representing systemic variations of liposome properties including diameter, charge, membrane fluidity and surface hydration. One of these, called Nanolipolee-007 herein, is a lipid based PEGylated neutral charged leelamine loaded liposomal system, 80:20 mol % for ePC: DPPE: PEG-2000.

Synthesis of Nanolipolee-007

Figure 23:
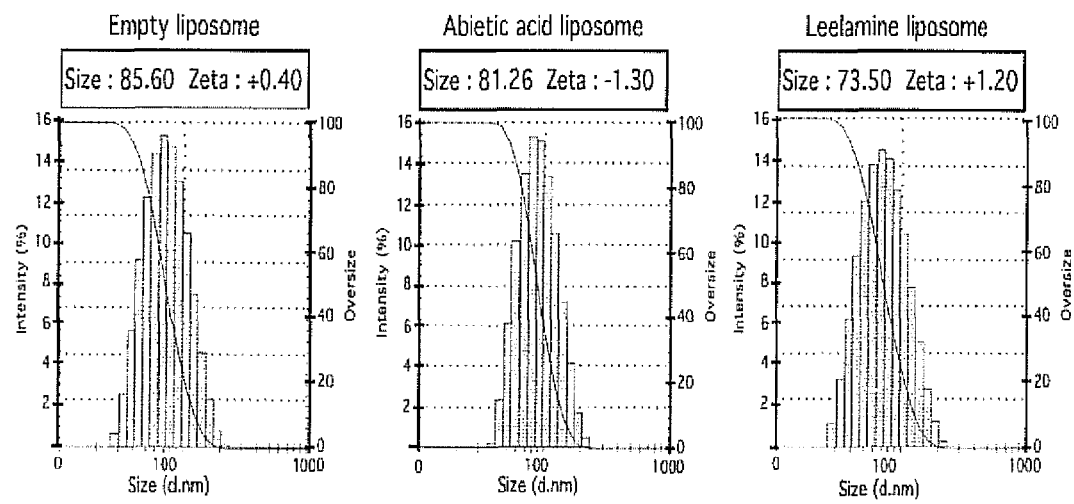
FIG. 23 is a set of graphs showing the size and charge of empty liposomes, abietic acid-containing liposomes and leelamine-containing liposomes (Nanolipolee-007)

Leelamine hydrochloride (Tocris Biosciences, Ellisville, Mo.) is encapsulated into nanoliposomes to generate Nanolipolee-007 by combining L-α-phosphatidylcholine (ePC) and 1,2-dipalmitoyl-sn-Glycero-3-Phosphoethanolamine-N-[methoxy(polyethylene glycol)-2000]ammonium salt (DPPE-PEG-2000) in chloroform at 80:20 mol % and a final lipid concentrations 25 mg/mL in buffer solution (Avanti Polar Lipids Inc-Alabaster, Ala.). 7.5 mg of leelamine hydrochloride is used for 1 milliliter of nanoliposome solution. Mixtures are dried under nitrogen gas and resuspended in 0.9% saline at 60° C. Following rehydration, sonicated at 60° C. for 30 minutes followed by extrusion at 60° C. through a 100-nm polycarbonate membrane using Avanti Mini Extruder (Avanti Polar Lipids Inc-Alabaster, Ala.). The particle size and charge of nanoliposomes is performed by using a Malvern Zetasizer Nano, Malvern Instruments, UK). Nanolipolee-007 is homogenously distributed in nanosize range (70-80 nm) with a neutral surface charge, FIG. 23.

Figure 24:
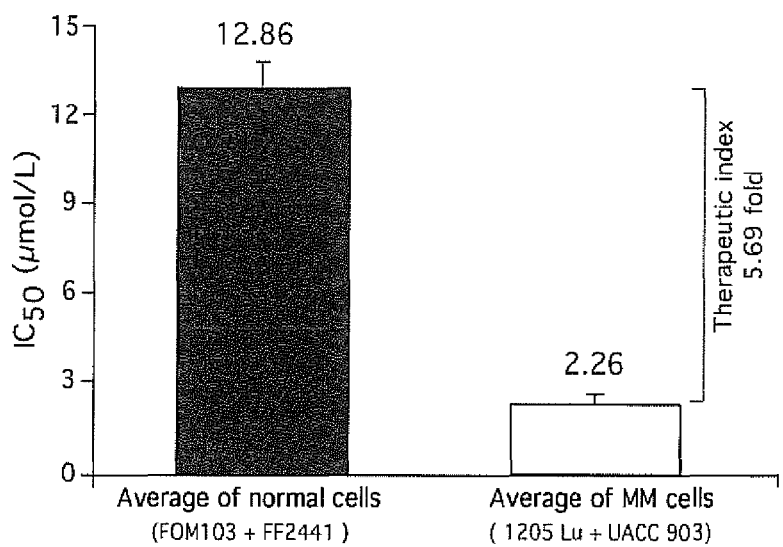
FIG. 24 is a graph showing effects of leelamine-containing liposomes on melanoma cells compared to normal cells.

The $IC_{50}$ and effect of liposomal preparations of leelamine on viability of normal human melanocytes, fibroblasts and melanoma cells UACC 903 and 1205 Lu are measured using the MTS assay (Promega, Madison, Wis.). Empty liposomes or liposomes containing abietic acid are used as controls. $5 \times 10^3$ cells per well in 100 μL of media are plated and grown in a 96-well plate for 48 or 72 hours for melanoma and normal cell lines, respectively. The cells are then treated with 0.62 to 40 μmol/L of liposome alone, a liposomal preparation of abietic acid, or with Nanolipolee-007 for 24 hours. $IC_{50}$ values for each liposome in μmol/L for respective cell lines are measured from three independent experiments using Graph-Pad Prism version 4.01 (GraphPad Software, La Jolla, Calif.). Nanolipolee-007 retains the growth inhibitory activity of leelamine in killing melanoma cells in culture and specifically kills melanoma cells compared to normal cells, FIG. 24.

Characterization of Nanolipolee-007

Physicochemical characterization of Nanolipolee-007.

Various key parameters for the stability of Nanolipolee-007 such as, sterility, size, charge, and efficacy are analyzed in different batches of preparations.

Figure 25:
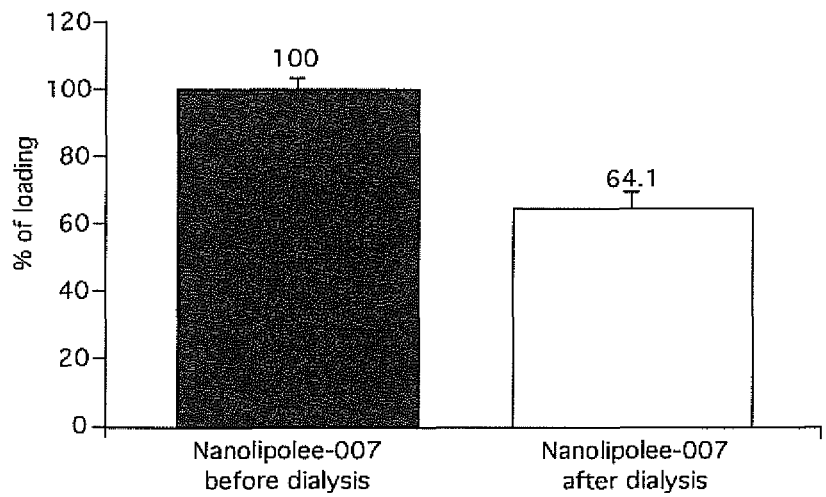
FIG. 25 is a graph showing loading of leelamine into liposomes.

Efficiency of leelamine loading and the purity of Nanolipolee-007 are characterized using tritium labeled leelamine by dialysis and size exclusion chromatography based approaches. One milliliter of Nanolipolee-007 suspension is placed in a 1 cm×5 cm long dialysis membrane bag (Molecular weight cut off: 25 kDa; Spectra/Por, Los Angeles, Calif.). The dialysis bag is suspended in 1 liter of 0.9% saline with constant stirring (300 rpm) for 12 hours, the amount of Tritium leelamine remaining in the Nanolipolee-007 is measured by liquid measured by liquid scintillation counter (LS-6500-Beckman Coulter, Fullerton, Calif.). To further validate the removal of free tritium labeled leelamine from the dialyzed and undialyzed Nanolipolee-007, size exclusion chromatography is performed. In brief, sepharose CL-4B column (0.6 cm×60 cm), equilibrated and eluted with 0.9% saline, pH 7.0 at room temperature. The eluted fractions from the column are collected (flow rate of 10 mL/h) followed the amount of Tritium labeled leelamine remaining in the Nanolipolee-007 is measured by liquid scintillation counter (LS-6500-Beckman Coulter, Fullerton, Calif.). Results show 64.1% loading of leelamine in liposomal formulation, FIG. 25.

Stability of Noanolipolee-007

Figure 26:
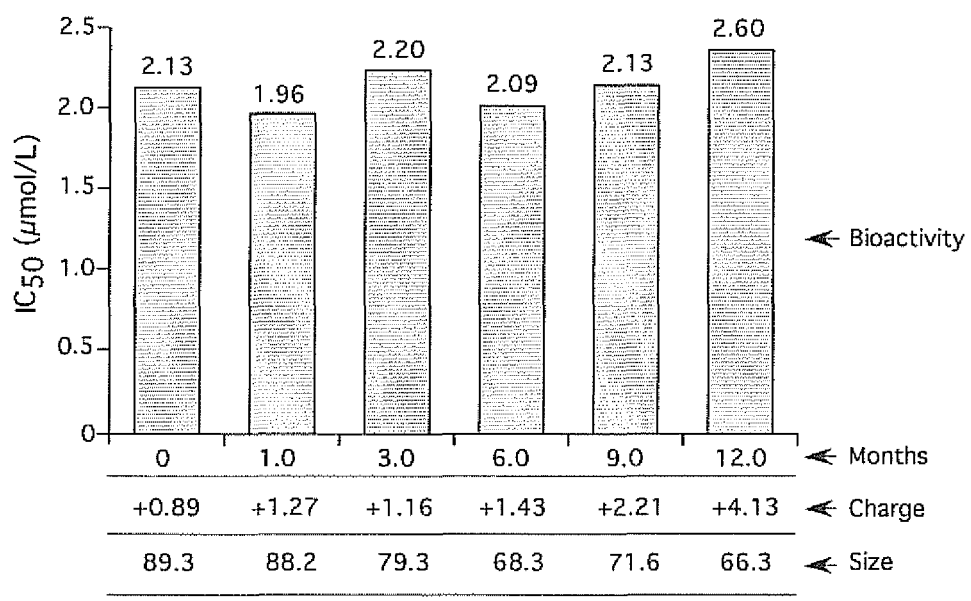
FIG. 26 is a graph showing particle size, charge and anti-cancer efficacy of Nanolipolee-007 is highly stable in saline stored at 4° C. for a year.

The stability of Nanolipolee-007 is evaluated in a time dependent manner by storing at 4° C. for up to 12 months. The particle size, charge (Malvern Zetasizer Nano, Malvern Instruments, UK) and efficacy (MTS assay) are determined as a function of the storage time. Nanolipolee-007 is highly stable in saline stored at 4° C. for a year; maintaining its activity with $IC_{50}$ of 1.96-2.6 μmol/L, FIG. 26. During this period the size and charge distribution of the liposomes is maintained, and no aggregation or precipitation of the liposomes in the solution is apparent.

In Vitro Drug Release Kinetics of Nanolipolee-007

Figure 27:
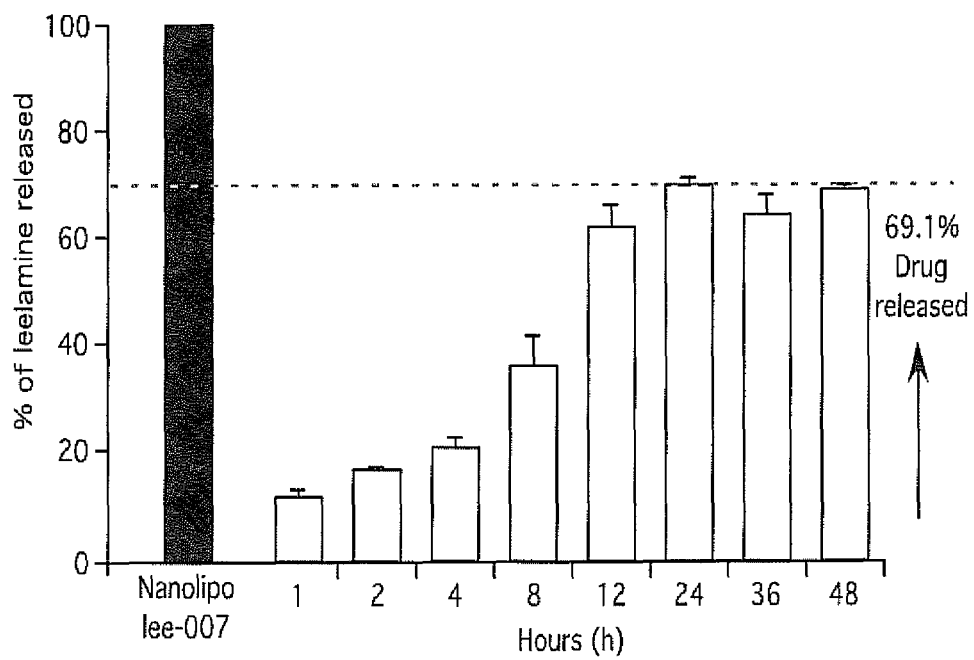
FIG. 27 is a graph showing in vitro leelamine release from Nanolipolee-007 liposomes.

A study of in vitro release of leelamine from nanoliposome is carried out at room temperature using dialysis membrane (Molecular weight cut off: 25 kDa; Spectra/Por, Los Angeles, Calif.). Briefly, 1.0 mL of tritium labeled Nanolipolee-007 suspension is placed in to dialysis membrane. The dialysis membrane is suspended in 1.0 L of 0.9% saline with constant stirring (300 rpm) for 12 hours, free unbound leelamine is separated from dialysis membrane. The amount of tritiated leelamine remaining in the nanoliposome within the membrane is removed and immersed in 500 mL of releasing medium containing 10 mM reduced glutathione (GSH) followed by constant stirring for 48 hours. At the time of different intervals 1, 2, 4, 8, 12, 24, 36 and 48 hours, 1.0 mL of released sample is withdrawn and radioactivity associated with the tritiated leelamine is measured by liquid scintillation counting (LS-6500-Beckman Coulter, Fullerton, Calif.). The in vitro drug release study shows that maximum amount of leelamine (69.1%) is released from Nanolipolee-007 within 24 hours, FIG. 27. Leelamine release is found to be very slow in first four hours and after 24 hours it released maximum amount until 36 hours.

Pharmacokinetics Study of Nanolipolee-007.

A pharmacokinetic study is carried out to determine the levels of leelamine in the circulation. Swiss Webster (n=5) mice are injected with 30 mg/kg body weight of Nanolipolee-007 intravenously and animals are sacrificed and blood drawn by cardiac puncture at different intervals of time. Samples are kept at room temperature for 30 minutes followed by serum separation by centrifugation for 5 minutes at 5000 rpm. Next, 20 μL of the collected serum is added to 80 μL of acetonitrile with 5 μL of propranolol (transition of m/z 259.9 to 116.0) is used internal standard. Following this step the solution is vortexed for 30 seconds and then centrifuged at 10,000 rpm for 10 minutes. The supernatant extraction is transferred to auto sampler vials and subjected to liquid chromatography-mass spectrometry (LC-MS) using a Shimadzu LC-MS 2010

Figure 28:
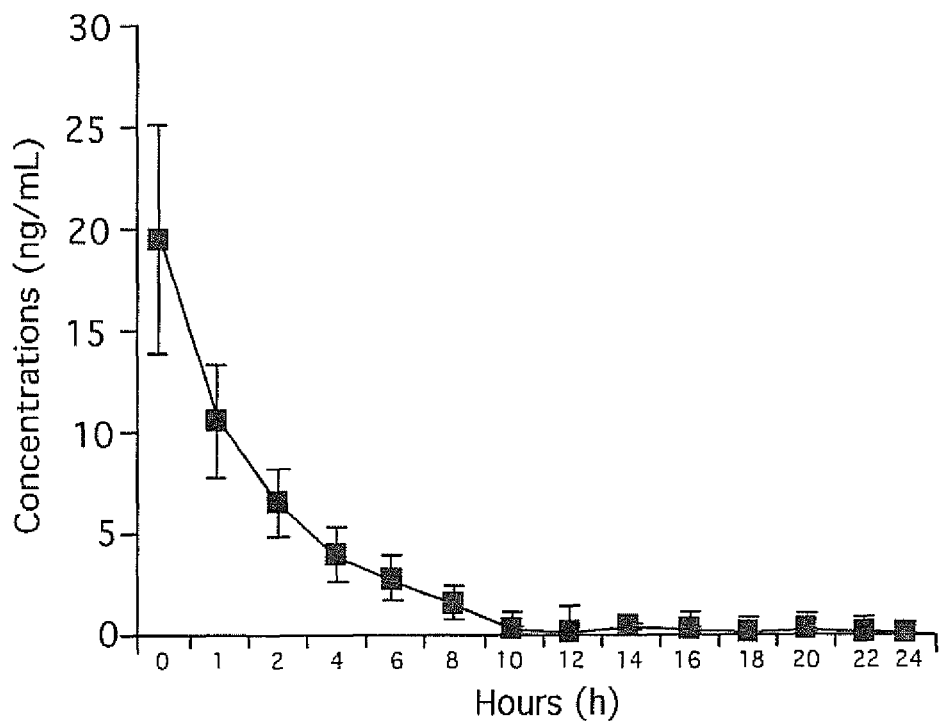
FIG. 28 is a graph showing results of a pharmacokinetic study to determine the levels of leelamine in serum in vivo following intraveneous administration of Nanolipolee-007.

EV system (Shimadzu, Tokyo, Japan). In this example, Nanolipolee-007 remains in the circulation for up to about 8 hours, FIG. 28.

Tumorigenicity Assessments.

Nanolipolee-007 inhibits melanoma tumor development.

Animals with preexisting tumors are treated intravenously with injections at a daily dose of 30 mg/kg body weight Nanolipolee-007. Empty liposome vehicle alone or a liposomal formulation of abietic acid is used a control Tumor kinetics are measured by subcutaneous injection of $1.0 \times 10^6$ UACC 903 or 1205 Lu cells in 0.2 mL of DMEM supplemented with 10% FBS subcutaneously injected above both left and right rib cages of 3- to 4-wk-old female athymic nude-Foxn1$^{nu}$ mice (Harlan Laboratories, Indianapolis, Ind.). Six days later, when a fully vascularized tumor (50-75 mm$^3$) has formed, mice are randomly divided into control and experimental groups (5 mice/group; 2 tumors/mouse) and treated with 30-mg/kg body weight of empty liposome vehicle, abietic acid liposomes or Nanolipolee-007 intravenously each day for 3-4 weeks. Body weight (grams) and dimensions of the developing tumors (mm$^3$) are measured at the time of drug treatment. Nanolipolee-007 significantly decreases tumor volume by 55% for UACC 903 cells, FIG. 29, and by 54% for 1205 Lu cells, FIG. 30, compared to controls.

Toxicity Assessments.

To assess toxicity, four to six week-old athymic-Foxn1$^{nu}$ nude mice, are treated with 30-mg/kg body weight of empty liposome vehicle, abietic acid liposomes or Nanolipolee-007 intravenously each day for 3-4 weeks. At the end of treatment, blood is collected from each sacrificed animal in a plasma separator tube with lithium heparin (BD Microtainer) following cardiac puncture and analyzed for ALP (Alkaline phosphatase), ALT (Alanine aminotransferase), AST (Aspartate aminotransferase), CK (Creatine kinase), CREA (Creatinine) and GLU (Glucose) levels to ascertain possible liver, heart, kidney, and pancreas related toxicity. A portion of vital organs, liver, heart, kidney, pancreas, and spleen—from each animal is formalin-fixed and paraffin embedded to examine for toxicity-associated changes in cell morphology and tissue organization following hematoxylin/eosin staining.

Figure 29:
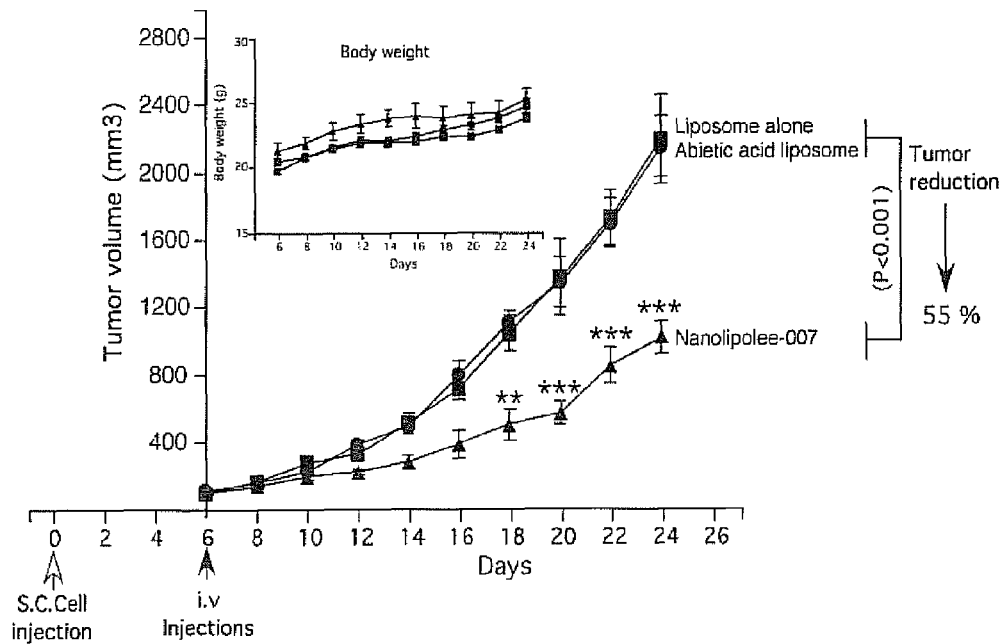
FIG. 29 is a graph showing effects of administration of Nanolipolee-007 on UACC 903 human melanoma cell tumors in mice compared to administration of vehicle (empty liposomes) alone or abietic acid-containing liposomes and an inset graph showing body weight of the same treated mice.
Figure 30:
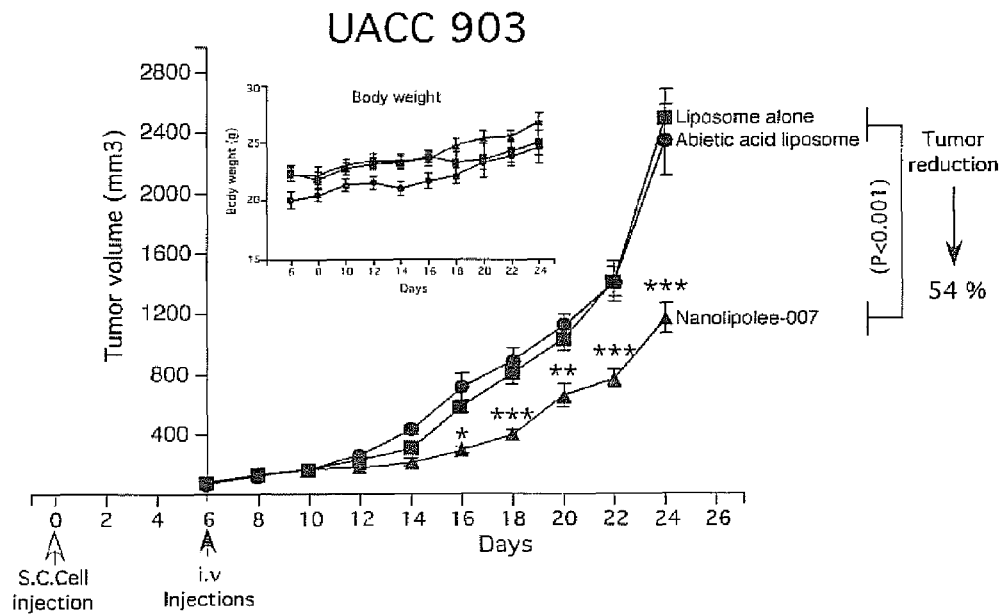
FIG. 30 is a graph showing effects of administration of Nanolipolee-007 on 1205 Lu human melanoma cell tumors in mice compared to administration of vehicle (empty liposomes) alone or abietic acid-containing liposomes and an inset graph showing body weight of the same treated mice.

Nanolipolee-007 treated animals do not show any significant changes in body weight, indicating negligible toxicity (FIGS. 29 and 30; insets). No noticeable changes serum parameters indicative of vital organ toxicity are observed, as shown in FIG. 31. Furthermore, analysis of hematoxylin/eosin stained tissue sections from control or Nanolipolee-007 treated mice shows no changes in the morphology or architecture of the liver, heart, lung, kidney or spleen. These data demonstrate that Nanolipolee-007 effectively inhibits melanoma tumor development leading to tumor regression without significant organ related toxicity.

Size and time match tumors for analysis of biological processes regulating tumor development.

The mechanisms by which Nanolipolee-007 delays tumor development is established by comparing size and time matched melanoma tumors treated with Nanolipolee-007 compared to empty liposome vehicle treated animals. $2.5 \times 10^6$ UACC 903 cells are injected subcutaneously into nude mice, generating tumors of the same size developing at parallel time points. Six days later, mice are treated intravenously with empty liposome vehicle or Nanolipolee-007 (30 mg/kg body weight) daily up to day 15. Tumors are harvested at 11, 13 and 15 days for comparison of rates of cellular proliferation, apoptosis and vessel density by immuno-histochemistry and Western blotting analysis. Cell proliferation is calculated using mouse anti-human Ki-67 staining from Pharmigen (San Diego, Calif.). Apoptosis rates are scored using "terminal deoxynucleotidyl transferase-mediated dUTP nick end labeling (TUNEL)" TMR Red Apoptosis kit from Roche (Mannheim, Germany). Vessel density indicative of apoptosis is estimated using a purified rat anti-mouse CD31 (PECAM-1) monoclonal antibody immunostaining (Pharmingen). Number of Ki-67, TUNEL and CD31 stained cells are quantified as the percentage of total cells in tumors using the IP Lab imaging software program. For all tumor analyses, a minimum of 6 different tumors with 4-6 fields per tumor is analyzed and results represented as the average±SEM.

Figure 32:
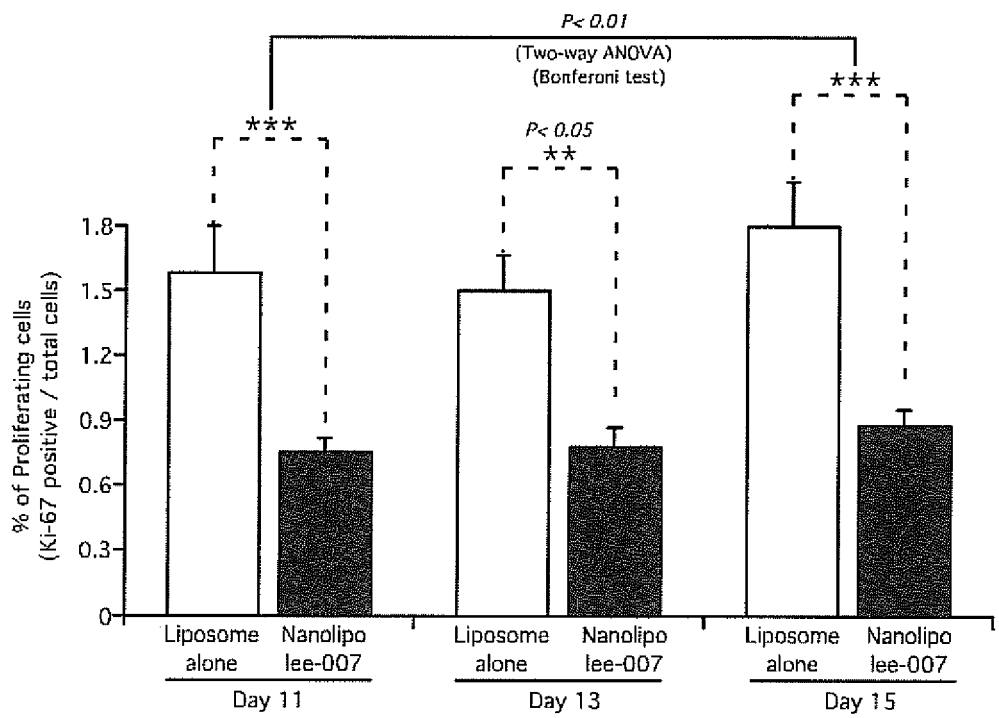
FIG. 32 is a graph showing effects of Nanolipolee-007 or vehicle (empty liposomes) on proliferating cells using Ki-67 immunostaining in size and time matched tumors.
Figure 33:
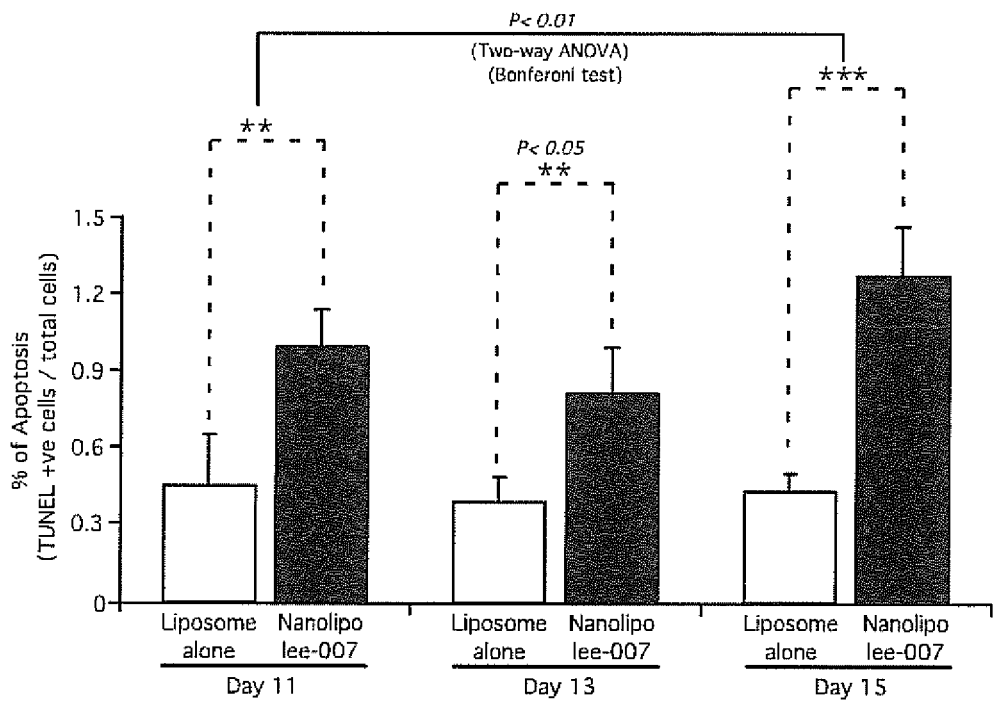
FIG. 33 is a graph showing effects of Nanolipolee-007 or vehicle (empty liposomes) on apoptosis using TUNEL staining in size and time matched tumors.
Figure 34:
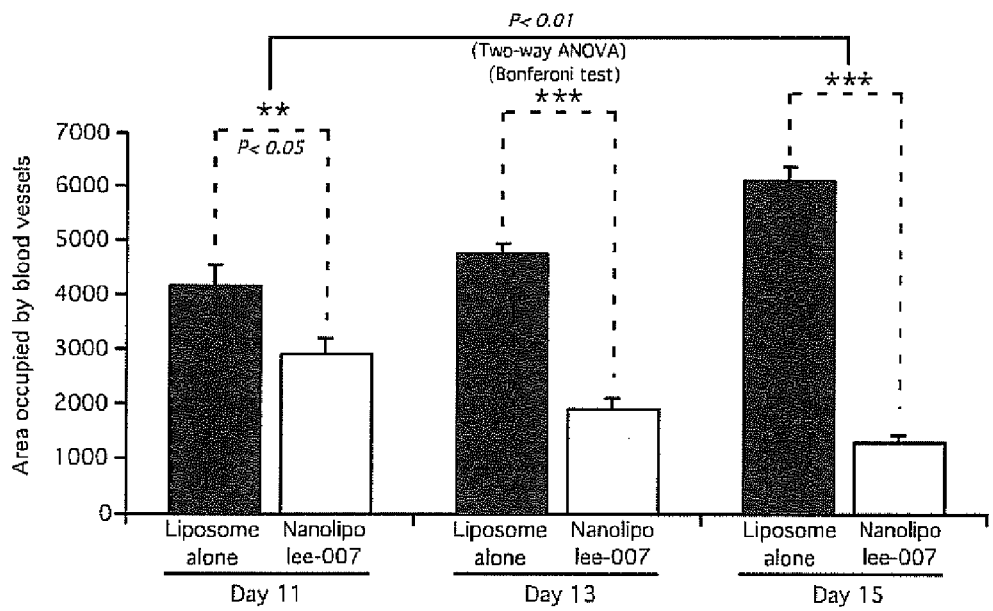
FIG. 34 is a graph showing effects of Nanolipolee-007 or vehicle (empty liposomes) on vascular development using CD31 immunostaining in size and time matched tumors.

At day 11, a statistically significant 60% reduction in proliferating and increasing apoptotic cells is observed after Nanolipolee-007 treatment but not vascular development rates compared with control treated animals, FIGS. 32, 33 and 34, $P<0.01$, two-way analysis of variance. Significant decreases in cellular proliferation and vascular development, along with a significant increase in apoptosis, are detected in all tumors compared with vehicle controls at days 13 and 15, FIGS. 32, 33 and 34, $P<0.01$, two-way analysis of variance.

Statistical Analysis.

Statistical analysis is performed using Prism 4.0 GraphPad Software. One-way or Two-way Analysis Of Variance (ANOVA) is used for group wise comparisons, followed by the Tukey's or Bonferroni's post hoc tests. For comparison between two groups, t test is used. Results represent at least two to three independent experiments and are shown as averages±S.E.M. Results with a P value less than 0.05 (95% CI) are considered significant.

Cell Viability, Proliferation, Apoptosis and Cell Cycle Analysis.

Effects of liposome formulations of leelamine are compared with non-liposomal leelamine and with liposomal abietic acid. Table 2 shows $IC_{50}$ (uM) for ghost liposomes, abietic acid liposomes and leelamine liposomes administered to normal cells and metastatic melanoma cell lines (24 hours treatment).

TABLE 2

| | Normal cells | | MM | |
|---|---|---|---|---|
| | FOM103 | FF2441 | 1205 Lu | UACC 903 |
| Ghost | >100 | >100 | >100 | >100 |
| Abietic acid liposome | >100 | >100 | >100 | >100 |
| Leelamine liposome | 12.90 | 13.83 | 2.76 | 1.97 |

Figure 35:
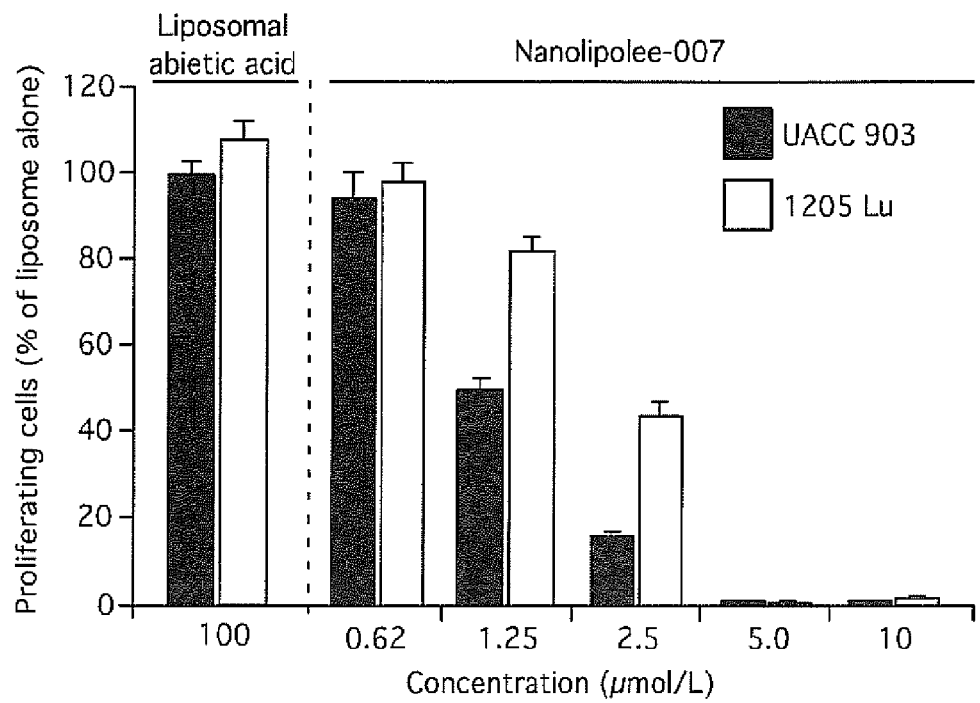
FIG. 35 is a graph showing effects of administration of Nanolipolee-007 or abietic acid-containing liposomes on proliferation of melanoma cells in vitro measured by BrdU incorporation.
Figure 36:
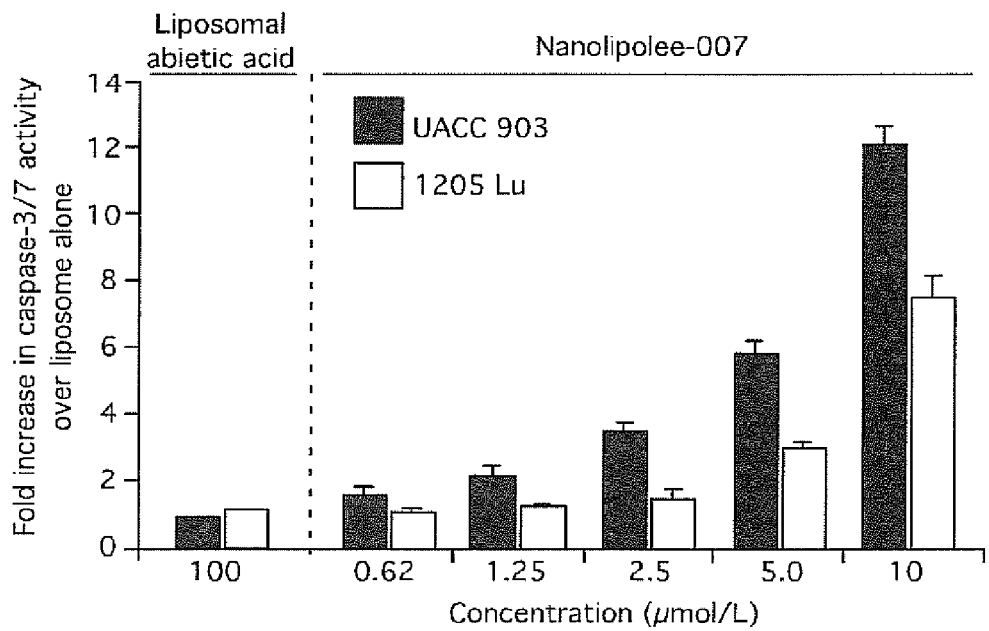
FIG. 36 is a graph showing effects of administration of Nanolipolee-007 or abietic acid-containing liposomes on apoptosis of melanoma cells in vitro measured by a caspase 3/7 assay.

Cellular proliferation and apoptosis rates are measured by seeding $5 \times 10^3$ UACC 903 and 1205 Lu melanoma cells in 96-well plates, followed by treated with 0.62 to 40 μmol/L of liposome alone, a liposomal preparation of abietic acid, or Nanolipolee-007 for 24 hours. Percentage proliferating and apoptotic cells are quantified by a colorimetric using cell proliferation ELISA BrdU kit (Roche Applied Sciences, Indianapolis, Ind.) and Apo-ONE Homogenous caspase-3/7 assay kit (Promega, Madison, Wis.), respectively, according to the manufacturer's instructions. Results are shown in FIGS. 35 and 36.

Figure 37:
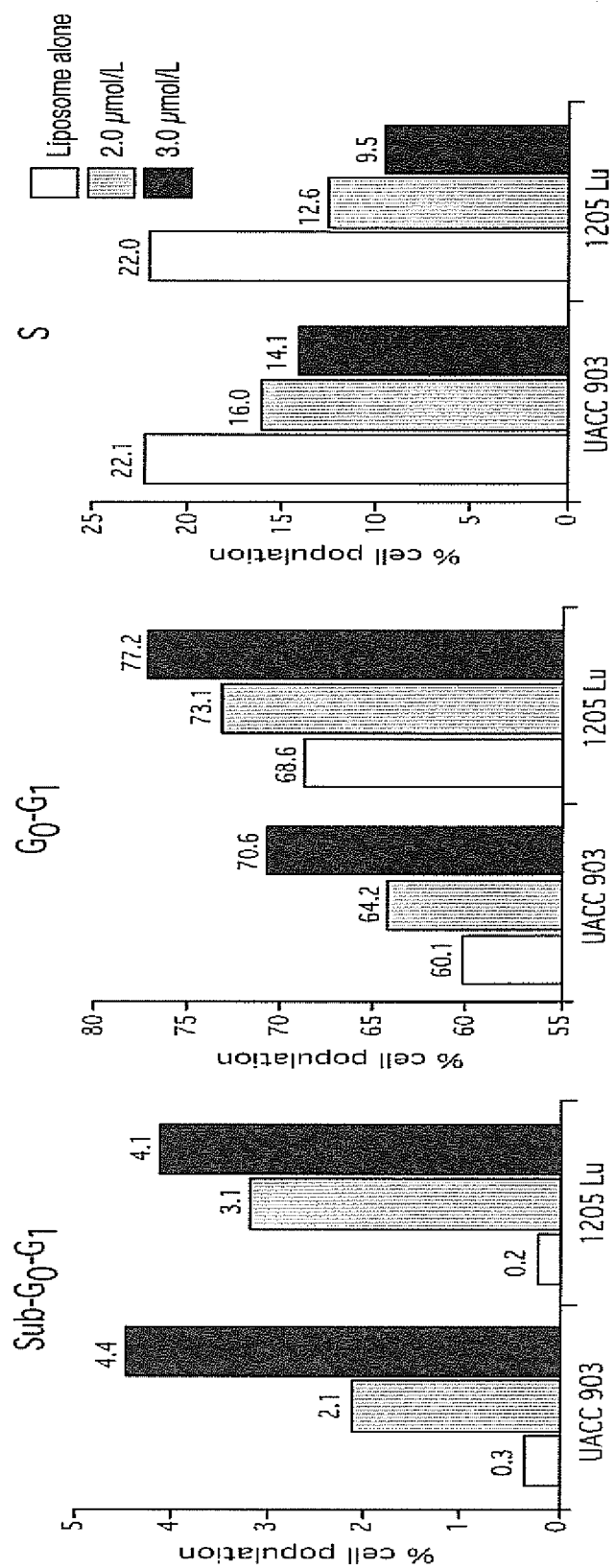
FIG. 37 is a set of graphs showing effects of administration of Nanolipolee-007 or vehicle (empty liposomes) on cell cycle of melanoma cells in vitro.

Analysis of cell cycle is performed by growing UACC 903 and 1205 Lu melanoma cells in 100-mm culture dishes followed by treatment with liposomes alone or Nanolipolee-007 (2-3 μmol/L) for 24 hours. Total floating and adherent cells are collected following trypsinization and stained using a 1 mL propidium iodide solution containing 100 μg/mL propidium iodide; (Sigma, St Louis, Mo.), 20 μg/mL Ribonuclease A (Roche diagnostics, Indianapolis, Ind.) and 3 μg/mL Triton X-100 dissolved in 0.1% (W/V) sodium citrate for 30 minutes at 4° C. Stained cells are analyzed using the FACScan analyzer (Becton Dickinson, Franklin lakes, NJ) and data processed utilizing ModFit LT software (Verity Software House, Topsham, Me.). Results are shown in FIG. 37.

Kinexus Antibody Microarray and Ingenuity Pathway Analysis to identify pathways targeted by Nanolipolee-007.

Pathways targeted by leelamine and Nanolipolee-007 in melanoma cells to decrease proliferation and trigger apoptosis are identified using a Kinexus Antibody Microarray and Ingenuity Pathway Analysis followed by Western blot confirmation. UACC903 human melanoma cells are treated with 3 µmol/L Nanolipolee-007 for 3-24 hours, lysates collected and processed by Kinexus using 812-antibody microarray analysis. Kinexus 812-antibody microarray results are analyzed using the Ingenuity Pathway Analysis (IPA) software. Significantly up-regulated or down-regulated pan-specific proteins with corresponding Swiss-Prot accession numbers and ratio changes are uploaded as an excel spreadsheet file to the Ingenuity Pathway Analysis server and pathways identified.

For Western blot analysis, $1 \times 10^6$ melanoma cells are plated in 100 mm culture dishes, 48 hours later, treated with empty liposomes or Nanolipolee-007 (3-6 µmol/L) for 3 to 24 hours. Protein lysates collected for Western blotting. The cell lysates are harvested in an RIPA lysis buffer containing protease and phosphatases inhibitors (Pierce Biotechnology, Rockford, Ill.). Blots are probed with antibodies according to each supplier's recommendations: antibodies to total Akt, phospho-Akt (Ser473), total PRAS40, phospho-PRAS40 (Thr246), total Bad, pBad (Ser 112) total Erk1/2, phospho-Erk1/2 (Thr202/Tyr 204), total CDK2, phospho-CDK2 (Thr160), phospho-Rb (Ser807/811), total Stat, phospho-Stat3 (Tyr705), caspase-3 and cleaved PARP from Cell Signaling Technology (Danvers, Mass.); total PRAS40 from Invitrogen (Carlsbad, Calif.); cyclin D1, α-enolase and secondary antibodies conjugated with horseradish peroxidase from Santa Cruz Biotechnology (Santa Cruz, Calif.). Immunoblots are developed using the enhanced chemiluminescence (ECL) detection system (Thermo Fisher Scientific, Rockford, Ill.). Intensity of protein bands is quantified using ImageJ software.

Figure 40:
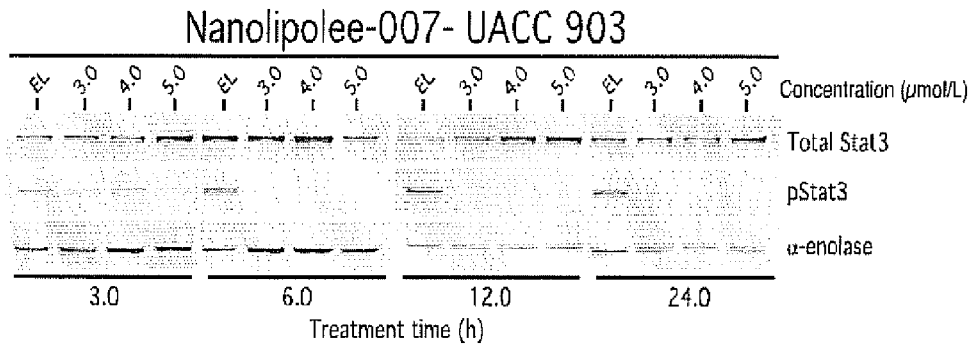
FIG. 40 is an image of a Western blot showing effects of Nanolipolee-007 treatment of UACC 903 melanoma cells on STAT signaling pathways regulating melanoma development.
Figure 41:
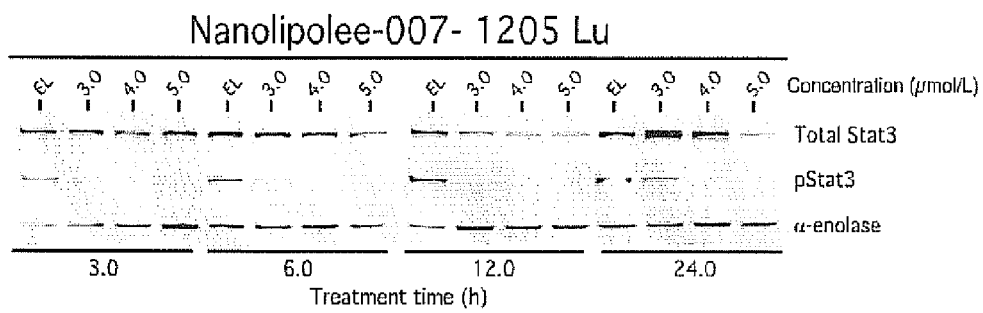
FIG. 41 is an image of a Western blot showing effects of Nanolipolee-007 treatment of 1205 Lu melanoma cells on STAT signaling pathways regulating melanoma development.
Figure 38:
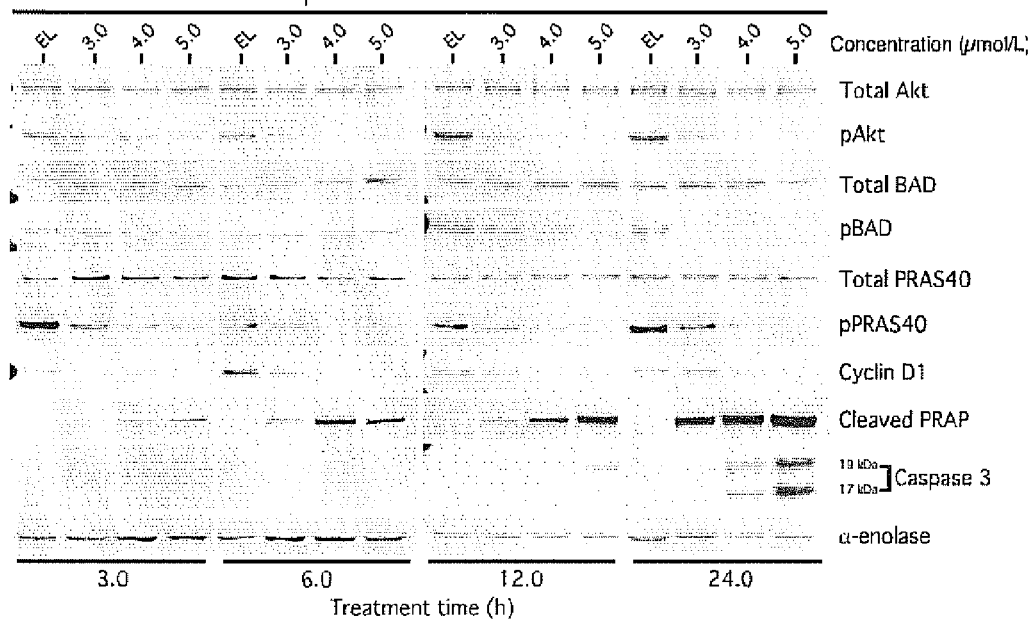
FIG. 38 is an image of a Western blot showing effects of Nanolipolee-007 treatment of UACC 903 melanoma cells on PI3K/Akt signaling pathways regulating melanoma development.
Figure 39:
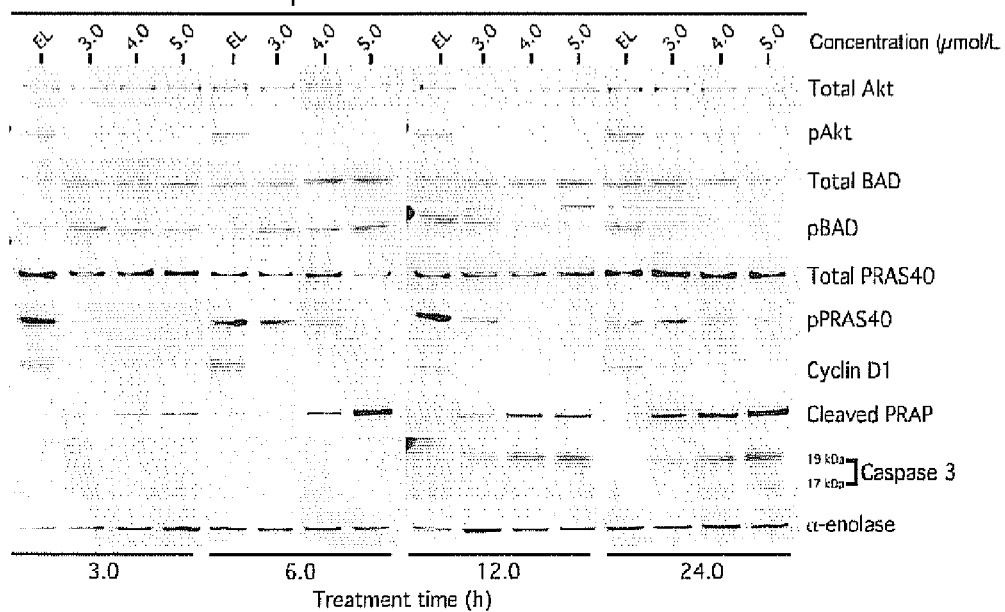
FIG. 39 is an image of a Western blot showing effects of Nanolipolee-007 treatment of 1205 Lu melanoma cells on PI3K/Akt signaling pathways regulating melanoma development.
Figure 42:
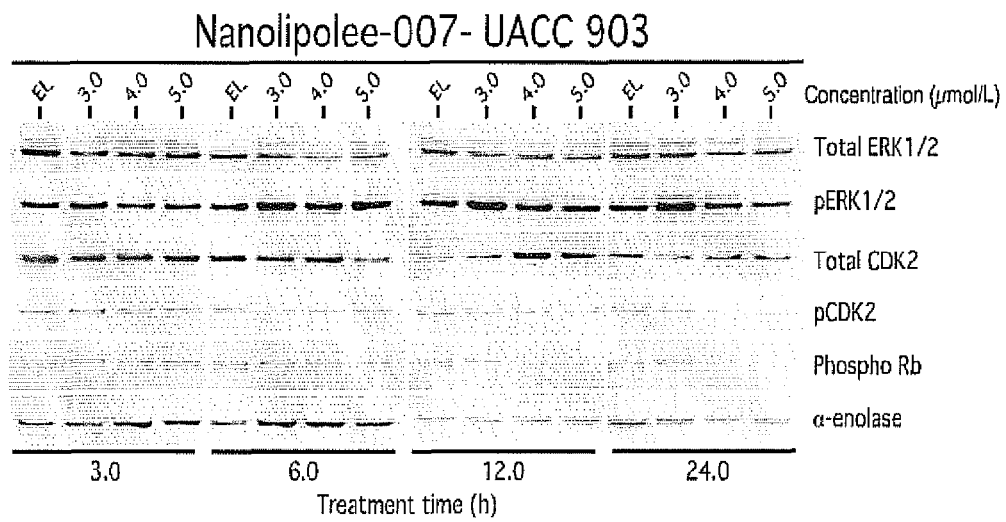
FIG. 42 is an image of a Western blot showing effects of Nanolipolee-007 treatment of UACC 903 melanoma cells on MAPK signaling pathways regulating melanoma development.
Figure 43:
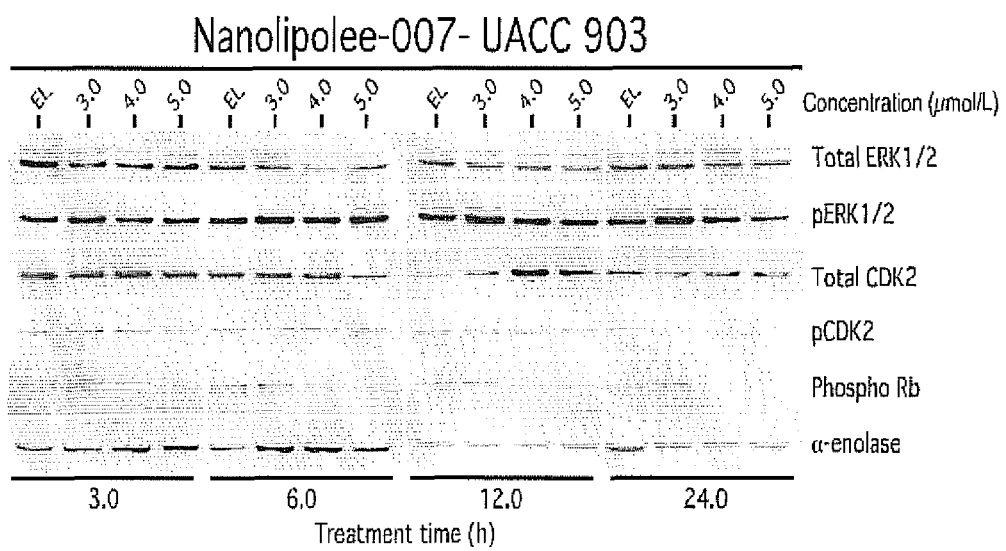
FIG. 43 is an image of a Western blot showing effects of Nanolipolee-007 treatment of 1205 Lu melanoma cells on MAPK signaling pathways regulating melanoma development.
Figure 44:
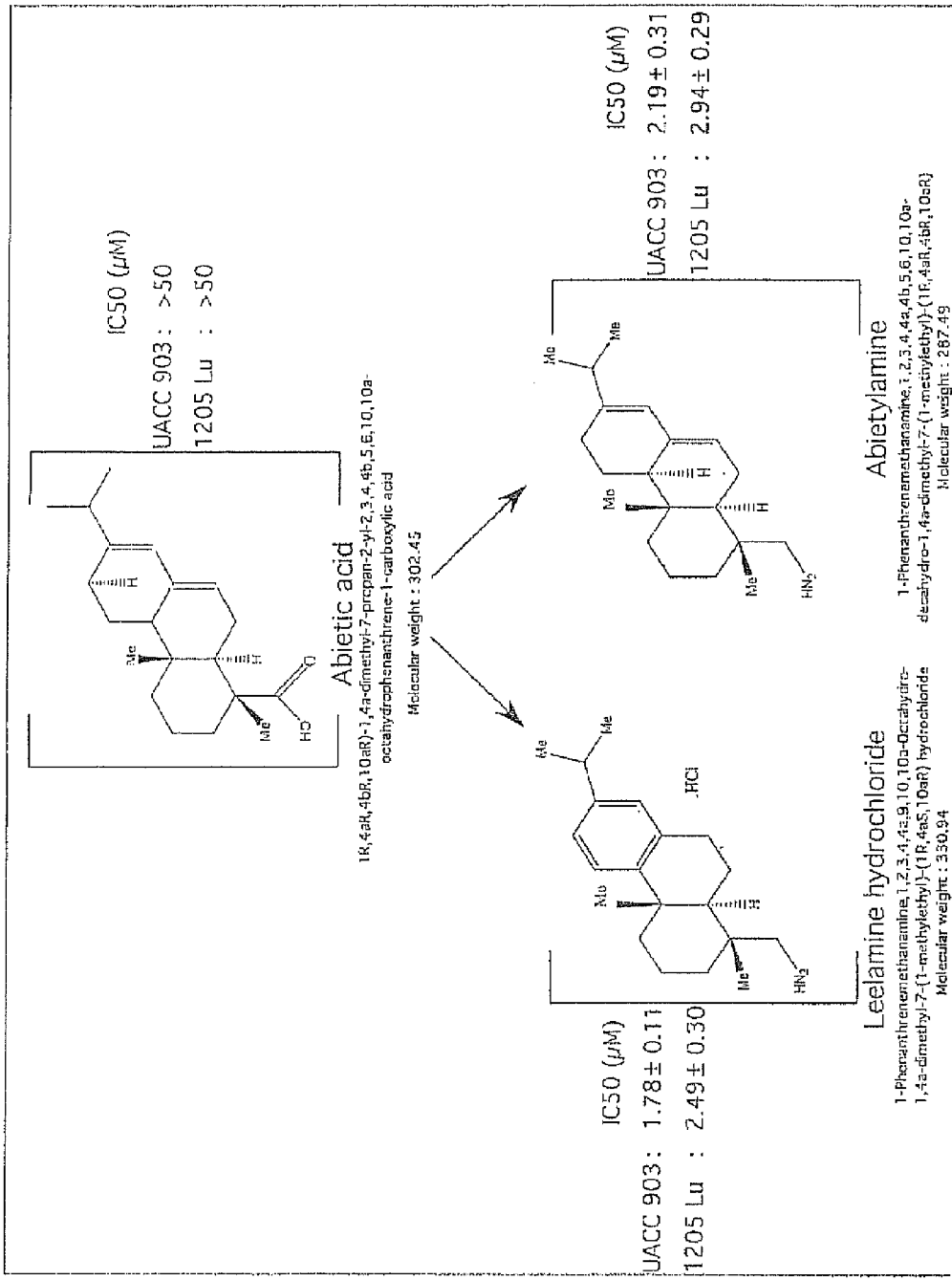
FIG. 44 is a chemical structure illustration of leelamine hydrochloride, abietic acid and abietylamine.

Leelamine and Nanolipolee-007 decrease activity of the STAT as well as PI3 and MAP kinases pathways, which are three major signaling pathways promoting melanoma development. Decreased signaling through each pathway following treatment with 3 to 6 µmol/L of Nanolipolee-007 for 3 to 24 hours is shown for PI3 kinase pathway (FIGS. 38 and 39, UACC 903 and 1205 Lu cells, respectively), STAT pathway (FIGS. 40 and 41, UACC 903 and 1205 Lu cells, respectively) and MAP kinase pathway (FIGS. 42 and 43, UACC 903 and 1205 Lu cells, respectively).

Example 5

FIGS. 44, 45, 46 and 47 show structures of abietic acid, leelamine, abietylamine, examples of abietic acid ester derivatives of abietic acid, examples of leelamine derivatives and examples of abietylamine derivatives. Further examples of compounds described herein are listed in Table 3.

TABLE 3

| Name | IUPAC Names |
| --- | --- |
| Abietic Acid/GPR-1 | (1R,4aR)-1,4a-dimethyl-7-(propan-2-yl)-1,2,3,4,4a,4b,5,6,10,10a-decahydrophenanthrene-1-carboxylic acid |

TABLE 3-continued

| Name | IUPAC Names |
| --- | --- |
| Abietyl alcohol/GPR-8 | [(1R,4aR)-1,4a-dimethyl-7-(propan-2-yl)-1,2,3,4,4a,4b,5,6,10,10a-decahydrophenanthren-1-yl]methanol |
| Abietylamine/GPR-3 | {[(1R,4aR)-1,4a-dimethyl-7-(propan-2-yl)-1,2,3,4,4a,4b,5,6,10,10a-decahydrophenanthren-1-yl]methyl}amine |
| Abieticamide/GPR-2 | (1R,4aR)-1,4a-dimethyl-7-(propan-2-yl)-1,2,3,4,4a,4b,5,6,10,10a-decahydrophenanthrene-1-carboxamide |
| N-methylabieticamide/GPR-6 | (1R,4aR)-N,1,4a-trimethyl-7-(propan-2-yl)-1,2,3,4,4a,4b,5,6,10,10a-decahydrophenanthrene-1-carboxamide |
| N-methylabietylamine/GPR-7 | {[(1R,4aR)-1,4a-dimethyl-7-(propan-2-yl)-1,2,3,4,4a,4b,5,6,10,10a-decahydrophenanthren-1-yl]methyl}(methyl)amine |
| N,N-diethylabieticamide/GPR-11 | (1R,4aR)-N,N-diethyl-1,4a-dimethyl-7-(propan-2-yl)-1,2,3,4,4a,4b,5,6,10,10a-decahydrophenanthrene-1-carboxamide |
| N,N-diethylabietylamine/GPR-12 | {[(1R,4aR)-1,4a-dimethyl-7-(propan-2-yl)-1,2,3,4,4a,4b,5,6,10,10a-decahydrophenanthren-1-yl]methyl}diethylamine |
| Leelamine | [(1R,4aS)-1,4a-dimethyl-7-(propan-2-yl)-1,2,3,4,4a,9,10,10a-octahydrophenanthren-1-yl]methanamine |
| N-acetylleelamine/GPR-4L | N-{[(1R,4aS)-1,4a-dimethyl-7-(propan-2-yl)-1,2,3,4,4a,9,10,10a-octahydrophenanthren-1-yl]methyl}acetamide |
| N-trifluoroacetylleelamine/GPR-1L | N-{[(1R,4aS)-1,4a-dimethyl-7-(propan-2-yl)-1,2,3,4,4a,9,10,10a-octahydrophenanthren-1-yl]methyl}-2,2,2-trifluoroacetamide |
| N-tribromoacetylleelamine/GPR-5L | N-{[(1R,4aS)-1,4a-dimethyl-7-(propan-2-yl)-1,2,3,4,4a,9,10,10a-octahydrophenanthren-1-yl]methyl}-2,2,2-tribromoacetamide |
| N-benzoylleelamine/GPR-7L | N-(((1R,4aS)-7-isopropyl-1,4a-dimethyl-1,2,3,4,4a,9,10,10a-octahydrophenanthren-1-yl)methyl)benzamide |
| N-benzylleelamine/GPR-8L | N-benzyl-1-((1R,4aS)-7-isopropyl-1,4a-dimethyl-1,2,3,4,4a,9,10,10a-octahydrophenanthren-1-yl)methanamine |

Example 6

Synthesis of Compounds

Figure 48:
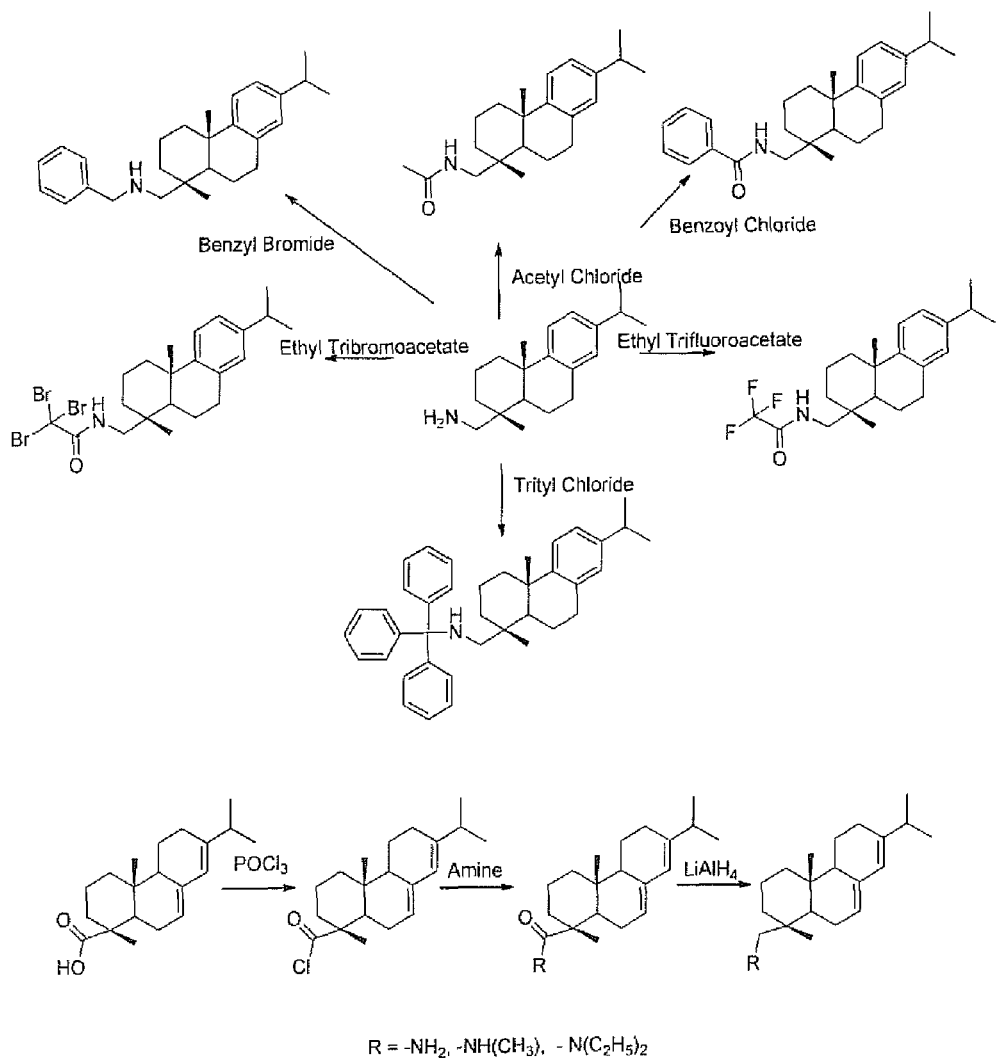
FIG. 48 is a scheme for synthesis of compounds described herein.

FIG. 48 schematically shows synthetic schemes for selected compounds. Analogous syntheses are used to produce related compounds included in compositions and methods described herein.

Example 7

Synthesis and Analysis of Compounds

NMR spectra are recorded using a Bruker Avance 500 MHz spectrometer at the Biomedical Research facility of State University Hershey College of Medicine, Hershey Pa. Chemical shifts (δ) are reported in parts per million downfield from the internal standard. The signals are quoted as s (singlet), d (doublet), t (triplet), m (multiplet), and dt (doublet of triplet). Mass spectroscopic results are determined at the Core Facility of Penn State University Hershey College of Medicine, Hershey Pa. Thin-layer chromatography (TLC) is developed on aluminum supported pre-coated silica gel plates (EMD, Germany). Column chromatography is conducted on neutral silica gel (60-200 mesh). Purity of the compounds is established by HPLC using HP-Agilent 1200 HPLC system on $C_{18}$ column and all compounds have a purity of >95% unless otherwise mentioned.

Figure 49:
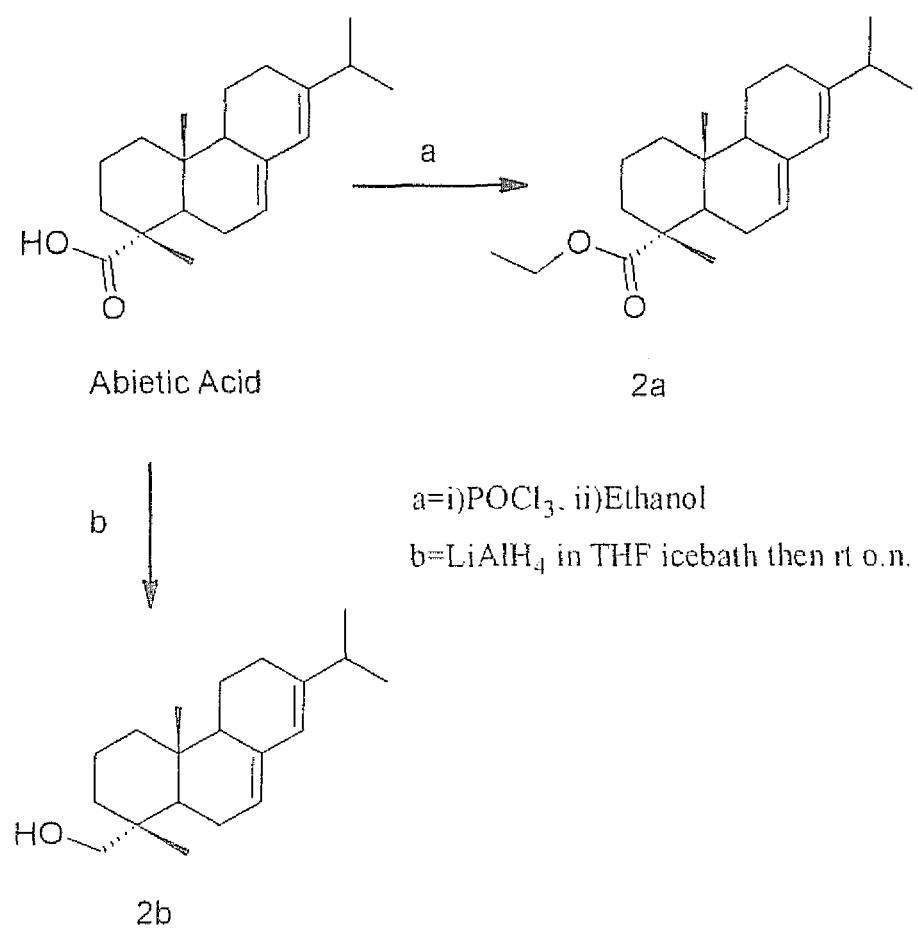
FIG. 49 is a scheme for synthesis of compounds described herein.

FIGS. 49, 50 and 51 show synthetic schemes for compounds designated 2a, 2b, 3a, 3b, 3c, 4a, 4b, 4c, 5a, 5b, 5c, 5d and 5e and described in detail below.

(1R,4aR)-1,4a-dimethyl-7-(propan-2-yl)-1,2,3,4,4a, 4b,5,6,7,10a-decahydrophenanthrene-1-carbonyl chloride A mixture of dihydroabietic acid (1.0 eq. 9.95 mmol), phosphorous (III) chloride (1.1 eq. 10.95 mmol) and DMF (0.1 ml) is refluxed overnight in THF (20 ml). The reaction mass is filtered under suction and concentrated under vacuum to give 2.98 g (93%) yellow oil. The compound is used immediately for the next step without any purification.

Compound 2a: {(1R,4aR)-1-(ethoxymethyl)-1,4a-dimethyl-7-(propan-2-yl)-1,2,3,4,4a,4b,5,6,7, 10adecahydrophenanthrene To a crude acid chloride (1.0 eq. 3.11 mmol) is added excess of ethanol and reaction is stirred for 2-4 hours. The reaction is then washed with saturated sodium bicarbonate solution, followed by water and extraction with ethyl acetate. The organic layer is separated, dried over anhydrous sodium sulphate and removed under reduced pressure to get crude product. The crude product is purified over neutral silica and eluted with 10-20% ethyl acetate in n-hexanes to get 0.49 g (48%) of pure ester. HPLC purity-85%; $^1$H NMR (CDCl$_3$, δ ppm) 5.78 (s, 1H), 5.37-5.38 (d, 1H), 4.04-4.75 (m, 2H), 2.81-2.93 (m, 1H), 2.20-2.33 (m, 1H), 2.04-2.12 (m, 2H), 1.70-1.85 (m, 4H), 1.45-1.65 (m, 6H), 1.20-1.30 (m, 12H), 0.97-1.03 (m, 3H).

Compound 2b: [(1R,4aR)-1,4a-dimethyl-7-(propan-2-yl)-1,2,3,4,4a,4b,5,6,7,10a-decahydrophenanthren-1-yl]methanol To a solution of dihydroabietic acid (1.0 eq. 3.30 mmol) in THF (10 ml) at 0° C. is added LiAlH$_4$ (4.15 eq. 13.69 mmol). The reaction is stirred overnight, treated with ethyl acetate at 0° C., followed by saturated ammonium chloride solution. The reaction is extracted with ethyl acetate, separated, dried over anhydrous sodium sulphate and organics removed under reduced pressure to get crude alcohol. The crude product is purified over neutral silica and eluted with n-hexanes to get 0.55 g (58%). HPLC purity→95%; Mass=286; $^1$H NMR (CDCl$_3$, δ ppm) 5.78 (s, 1H), 5.40-5.41 (t, 1H), 3.46-3.49 (m, 1H), 3.14-3.24 (m, 1H), 2.08-2.24 (m, 1H), 2.01-2.08 (m, 2H), 1.80-1.88 (m, 2H), 1.51-1.60 (m, 6H), 1.37-1.41 (m, 2H), 1.21-1.26 (m, 2H), 1.03-1.05 (m, 1H), 1.00-1.02 (m, 6H), 0.89 (s, 3H), 0.83 (s, 3H).

Compound 3a: {[(1R,4aR)-1,4a-dimethyl-7-(propan-2-yl)-1,2,3,4,4a,4b,5,6,10,10a-decahydrophenanthren-1-yl]methyl}amine Excess ammonia gas is passed into a stirred mixture of dihydroabietic acid chloride (1.0 eq. 9.28 mmol) in dichloromethane at 0° C. for 2-3 hours. The reaction is treated with 3N hydrochloric acid, followed by saturated sodium bicarbonate solution, finally with water, organics dried over anhydrous sodium sulphate and concentrated under vacuum to get a pale yellow product. The crude product is purified over neutral silica and elution with 20% ethyl acetate in n-hexanes to 35% ethyl acetate in n-hexanes to get 1.35 g (48%) of pure amide. HPLC purity→95%; Mass=301.67, $^1$H NMR (CDCl$_3$, δ ppm) 5.78 (s, 1H), 5.37-5.38 (t, 1H), 2.20-2.28 (m, 1H), 2.10-2.11 (m, 3H), 2.02 (s, 1H), 1.63-1.82 (m, 3H), 1.59-1.63 (m, 3H), 1.28-1.31 (m, 5H), 1.23-1.25 (m, 4H), 1.01-1.04 (m, 6H), 0.86 (s, 3H).

Compound 3b: (1R,4aR)—N,1,4a-trimethyl-7-(propan-2-yl)-1,2,3,4,4a,4b,5,6,10,10a-decahydrophenanthrene-1-carboxamide To a mixture of dihydroabietic acid chloride (1.0 eq. 6.23 mmol) in dichloromethane (30 ml) is added methylamine solution 2M in THF (1.1 eq. 6.85 mmol) at 0° C. and the reaction is stirred at RT overnight. The reaction mass is treated with dil. HCl, extracted with ethyl acetate, washed with brine, dried over anhydrous sodium sulphate and concentrated under vacuum to get colorless oil. The crude is purified over neutral silica and elution with 20% ethyl acetate in n-hexanes to 35% ethyl acetate in n-hexanes to get 1.15 g (58%) of pure amide. HPLC purity→95% LCMS=327.60 C$_{21}$H$_{33}$NO $^1$H NMR (CDCl$_3$, δ ppm) 5.78 (s, 1H), 5.37-5.38 (t, 1H), 2.20-2.28 (m, 1H), 2.26 (s, 3H), 2.10-2.11 (m, 3H), 2.02 (s, 1H), 1.63-1.82 (m, 3H), 1.59-1.63 (m, 3H), 1.28-1.31 (m, 5H), 1.23-1.25 (m, 3H), 1.01-1.04 (m, 6H), 0.86 (s, 3H).

Compound 3c: (1R,4aR)—N,N-diethyl-1,4a-dimethyl-7-(propan-2-yl)-1,2,3,4,4a,4b,5,6,10,10a-decahydrophenanthrene-1-carboxamide To a mixture of dihydroabietic acid chloride (1.0 eq., 6.23 mmol) in dichloromethane (30 ml) is added dimethylamine (1.1 eq. 6.85 mmol) at 0° C. and the reaction is stirred at RT overnight. The reaction mass is treated with dil. HCl, extracted with ethyl acetate, washed with brine, dried over anhydrous sodium sulphate and concentrated under vacuum to get colorless oil. The crude is purified over neutral silica and elution with 20% ethyl acetate in n-hexanes to 35% ethyl acetate in n-hexanes to get 1.0 g (50%) of pure amide. HPLC purity→95%; LCMS=357.90, $^1$H NMR (CDCl$_3$, δ ppm) 5.77 (s, 1H), 5.38-5.39 (t, 1H), 3.47-3.51 (m, 2H), 3.33-3.72 (m, 2H), 2.17-2.23 (m, 3H), 2.06-2.08 (m, 3H), 1.80-1.90 (m, 2H), 1.61-1.63 (m, 2H), 1.32 (s, 3H), 1.21-1.26 (m, 6H), 1.12-1.14 (m, 6H), 1.00-1.03 (m, 6H), 0.85-0.98 (s, 5H).

General Method for Synthesis of Dihydroabietylamine Derivatives 4a, 4b and 4c

To a mixture of corresponding amides (1.0 eq. 0.33 mmol) in dry tetrahydrofuran (20 ml) is added 2M LiAlH4 in tetrahydrofuran (4.0 eq. 1.33 mmol) at 0-10° C. over the period of 5 min. The reaction is stirred for 4 hours (gradually allowing the temperature to rise to RT). The reaction is treated with ethyl acetate, followed by saturated ammonium chloride solution, which is acidified with 3N hydrochloric acid. The reaction is then extracted 3×10 ml ethyl acetate, washed with water and then with brine. The organics dried over anhydrous sodium sulphate and removed under vacuum to get crude compound. The crude compound on treating with 2M hydrogen chloride in ether at 0° C. and then overnight at room temperature, solvent removed under vacuum and treated with dry ether to get corresponding hydrochlorides salts of amine.

Synthesis of Dehydroabietylamine Derivatives 5a, 5b, 5c, 5d and 5e

Compound 5a: N-{[(1R,4aS)-1,4a-dimethyl-7-(propan-2-yl)-1,2,3,4,4a,9,10,10a-octahydrophenanthren-1-yl]methyl}-2,2,2-trifluoroacetamide To a solution of dehydroabietylamine (1.0 eq. 6.23 mmol) in tetrahydrofuran (30 ml) is added triethylamine (2.0 eq.

12.46 mmol) at 0° C. followed by ethyl trifluoroacetate (1.1 eq. 6.85 mmol) and the reaction is refluxed for 3-4 hours. The reaction mass is treated with dil. HCl, washed with water, dried over anhydrous sodium sulphate and concentrated under vacuum to get a colorless to pale yellow oil. The crude is purified over neutral silica and elution with 10% ethyl acetate in n-hexanes to 20% ethyl acetate in n-hexanes to get 1.37 g (58%) of pure amide. LCMS=396.42, 358.40, 381.47 corresponding to $C_{22}H_{30}F_3NO$; $^1H$ NMR ($CDCl_3$, δ ppm) 7.19-7.21 (d, 1H), 7.03-7.05 (dd, 1H), 6.934-6.935 (d, 1H), 6.28 (bs, 1H), 3.30-3.32 (m, 2H), 2.94-2.99 (m, 1H), 2.82-2.89 (m, 2H), 2.33-2.36 (m, 1H), 1.78-1.87 (m, 4H), 1.42-1.52 (m, 3H), 1.29-1.30 (m, 1H), 1.25-1.28 (m, 6H), 1.01 (s, 3H), 0.87-0.90 (s, 3H).

Compound 5b: N-{[(1R,4aS)-1,4a-dimethyl-7-(propan-2-yl)-1,2,3,4,4a,9,10,10a-octahydrophenanthren-1-yl]methyl}acetamide To a solution of dehydroabietylamine (1.0 eq. 6.23 mmol) in tetrahydrofuran (30 ml) is added triethylamine (2.0 eq. 12.46 mmol) at 0° C. followed by acetyl chloride (1.1 eq. 6.85 mmol) and the reaction is stirred for 3-4 hours at room temperature. The reaction mass is treated with dil. HCl, washed with water, dried over anhydrous sodium sulphate and concentrated under vacuum to get a yellow oil, which solidified gradually. The crude is purified over neutral silica and elution with 10% ethyl acetate in n-hexanes to 20% ethyl acetate in n-hexanes to get 2.07 g (60%) of pure amide. HPLC purity→95% LCMS=327.60 corresponding to $C_{22}H_{33}NO$, 369.40 corresponding to potassium adduct $C_{22}H_{33}KNO$ and 655.61 corresponding to dimer; $^1H$ NMR ($CDCl_3$, δ ppm) 7.17-7.18 (d, 1H), 6.99-7.01 (dd, 1H), 6.90 (s, 1H), 5.51 (bs, 1H), 3.22-3.25 (m, 1H), 3.08-3.12 (m, 1H), 2.90-2.95 (m, 1H), 2.79-2.86 (m, 2H), 2.28-2.31 (dt, 1H), 1.98 (s, 3H), 1.65-1.91 (m, 5H), 1.36-1.43 (m, 3H), 1.26 (s, 3H), 1.22-1.25 (m, 6H), 0.94 (s, 3H).

Compound 5c: N-(((1R,4aS)-7-isopropyl-1,4a-dimethyl-1,2,3,4,4a,9,10,10a-octahydrophenanthren-1-yl)methyl)benzamide To a solution of dehydroabietylamine (1.0 eq. 6.23 mmol) in tetrahydrofuran (30 ml) is added triethylamine (2.0 eq. 12.46 mmol) at 0° C. followed by acetyl chloride (1.1 eq. 6.85 mmol) and the reaction is stirred for 3-4 hours at room temperature. The reaction mass is treated with dil. HCl, washed with water, dried over anhydrous sodium sulphate and concentrated under vacuum to get a yellow oil, which solidified gradually. The crude is purified over neutral silica and elution with 10% ethyl acetate in n-hexanes to 20% ethyl acetate in n-hexanes to get 2.07 g (60%) of pure amide. HPLC purity→95% LCMS=390.51 corresponding to $C_{27}H_{35}NO$; $^1H$ NMR ($CDCl_3$, δ ppm) 7.72-7.73 (d, 2H), 7.47-7.50 (t, 1H), 7.40-7.43 (t, 2H), 7.18-7.23 (d, 1H), 6.98-6.99 (dd, 1H), 6.89 (s, 1H), 6.22 (s, 1H), 2.29-2.32 (d, 1H), 1.96-2.01 (m, 1H), 1.68-1.82 (m, 4H), 1.49-1.56 (m, 4H), 1.33-1.49 (m, 2H), 1.21-1.26 (m, 10H), 1.02 (s, 3H).

Compound 5d: N-benzyl-1-((1R,4aS)-7-isopropyl-1,4a-dimethyl-1,2,3,4,4a,9,10,10a-octahydrophenanthren-1-yl)methanamine To a solution of dehydroabietylamine (1.0 eq. 6.23 mmol) in tetrahydrofuran (30 ml) is added triethylamine (2.0 eq. 12.46 mmol) at 0° C. followed by benzyl bromide (1.1 eq. 6.85 mmol) and the reaction is refluxed for 3-4 hours. The reaction mass is washed with water, dried over anhydrous sodium sulphate and concentrated under vacuum to get colorless to pale yellow oil, which when triturated with dry ether gave white precipitate. Ether is decanted; precipitate is washed with ether several times to get 55 mg (2%) of pure amine.

HPLC purity→95% LCMS=376.73 (M+1) corresponding to $C_{27}H_{37}N$; $^1H$ NMR ($CDCl_3$, δ ppm) 7.54-7.55 (d, 2H), 7.32-7.34 (d, 3H), 6.97-6.99 (d, 1H), 6.78-6.85 (dd, 1H), 6.71 (s, 1H), 4.07 (s, 2H), 2.73-2.78 (m, 1H), 2.63-2.67 (m, 2H), 2.43-2.46 (d, 1H), 1.67-1.70 (m, 1H), 1.58-1.61 (m, 3H), 1.48 (s, 3H), 1.30-1.36 (m, 3H), 1.17 (m, 4H), 1.06-1.10 (m, 6H), 0.97 (s, 3H).

Compound 5e: {[(1R,4aS)-1,4a-dimethyl-7-(propan-2-yl)-1,2,3,4,4a,9,10,10a-octahydrophenanthren-1-yl]methyl}(triphenylmethyl)amine To a solution of dehydroabietylamine (1.0 eq. 6.23 mmol) in tetrahydrofuran (30 ml) is added triethylamine (2.0 eq. 12.46 mmol) at 0° C. followed by triphenylmethyl chloride (1.1 eq. 6.85 mmol) and the reaction is stirred for 3-4 hours at room temperature. The reaction mass is washed with water, dried over anhydrous sodium sulphate and concentrated under vacuum to get colorless to pale yellow oil. The crude is purified over neutral silica and elution with 10% ethyl acetate in n-hexanes to 20% ethyl acetate in n-hexanes to get 2.1 g (63%) of pure amine. HPLC purity→95% LCMS=286.50 (M+1) corresponding to $C_{39}H_{45}N$ minus the trityl group; $^1H$ NMR ($CDCl_3$, δ ppm) 7.54-7.55 (d, 2H), 7.32-7.34 (d, 3H), 6.97-6.99 (d, 1H), 6.78-6.85 (dd, 1H), 6.71 (s, 1H), 4.07 (s, 2H), 2.73-2.78 (m, 1H), 2.63-2.67 (m, 2H), 2.43-2.46 (d, 1H), 1.67-1.70 (m, 1H), 1.58-1.61 (m, 3H), 1.48 (s, 3H), 1.30-1.36 (m, 3H), 1.17 (m, 4H), 1.06-1.10 (m, 6H), 0.97 (s, 3H).

Example 8

Figure 52:
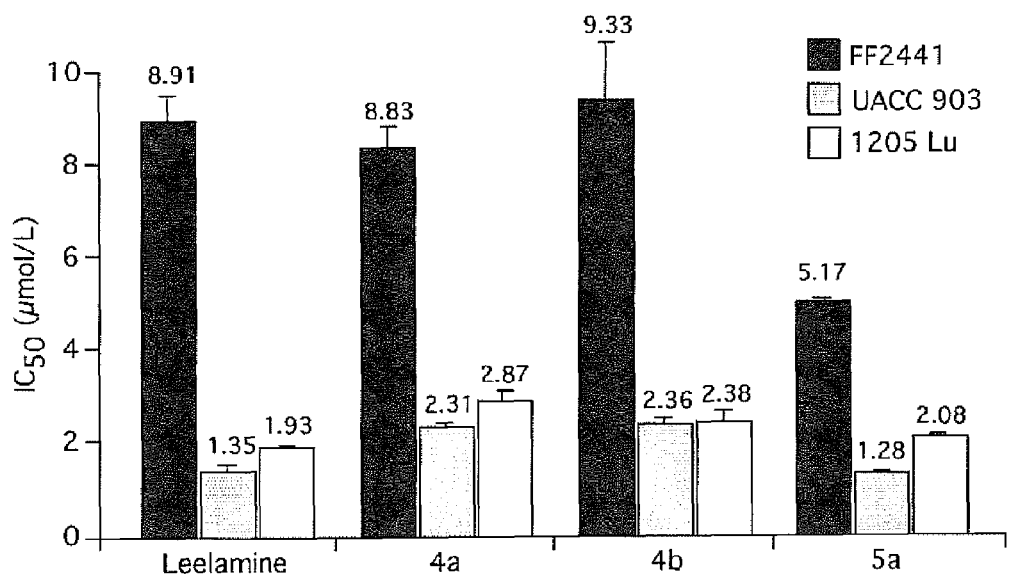
FIG. 52 is a graph showing effects of leelamine and compounds 4a, 4b and 5a on melanoma cells compared to normal fibroblast cells.

Dehydroabietylamine, its N-substituted derivatives and the corresponding dihydroabietylamine and its N-substituted derivatives are tested for their capability to inhibit cell growth of cancer cell lines, including melanoma (UACC 903, 1205Lu), breast (MCF-7), fibrosarcoma (HT-1080), colon (Caco-2), and prostate (PC-3) cancer cell lines. Viability and $IC_{50}$ of normal human fibroblasts and cell lines from melanoma and other malignancies following treatment with all the agents are measured using the MTS assay (Promega, Madison, Wis.). Human fibroblast FF2441 cells, metastatic melanoma cell lines 1205 Lu and UACC 903 as well as cancer cell lines representing sarcoma (HT-1080), prostate (PC-3, LNCaP), breast (MCF-7) and lung (A-549) are maintained in DMEM (Invitrogen, Carlsbad, Calif.) supplemented with 10% FBS (Hyclone, Logan, Utah) in a 5% $CO_2$ atmosphere, humidified 37° C. incubator. $5 \times 10^3$ cells per well in 100 μL of media are plated and grown in a 96-well plate for 48 to 72 h and treated with either DMSO vehicle control or 0.62 to 40 μmol/L for 24, 48 or 72 h. $IC_{50}$ values for each compound in μmol/L for respective cell lines are measured from three independent experiments using GraphPad Prism version 4.01 (GraphPad Software, La Jolla, Calif.). FIG. 52 is a graph showing $IC_{50}$ values for leelamine and compounds 4a, 4b and 5a in treated fibroblasts (FF2441) compared to melanoma cells. Selectivity ratio here is defined as ratio of activity against fibroblasts compared to activity against melanoma cells. Leelamine is relatively selective with a ratio of >6 and >4 for UACC903 and 1205Lu melanoma cells. The selectivity ratio of compound 4a is ~4 and ~3 for UACC903 and 1205Lu and for compound 4b is ~4 for both cell lines. The selectivity ratio of compound 5a is ~4 for UACC903 and >2 for 1205Lu cells.

Figure 53:
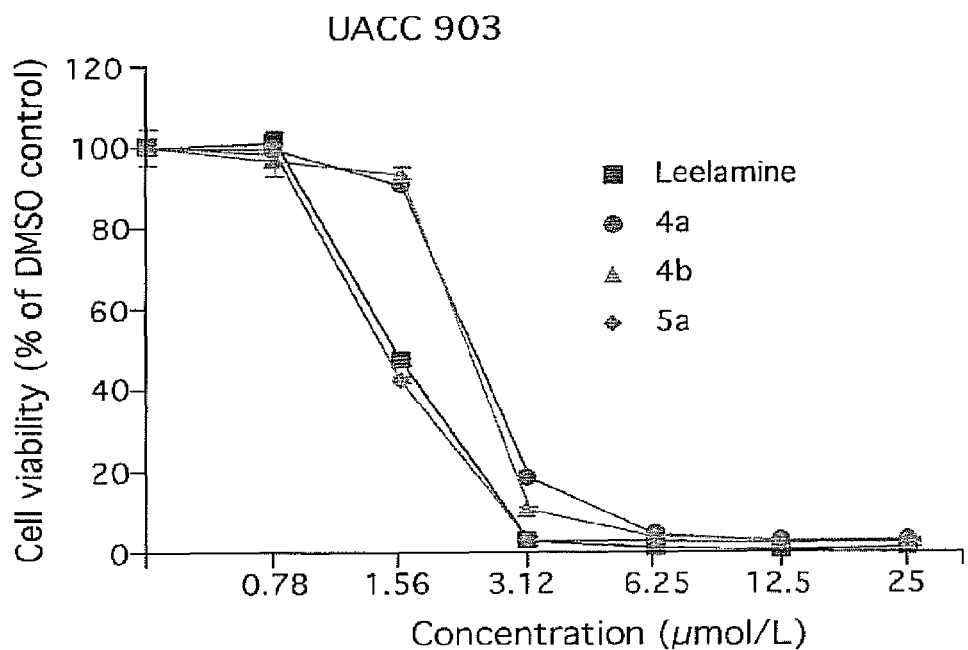
FIG. 53 is a graph showing effects of leelamine and compounds 4a, 4b and 5a on viability of melanoma cells.
Figure 54:
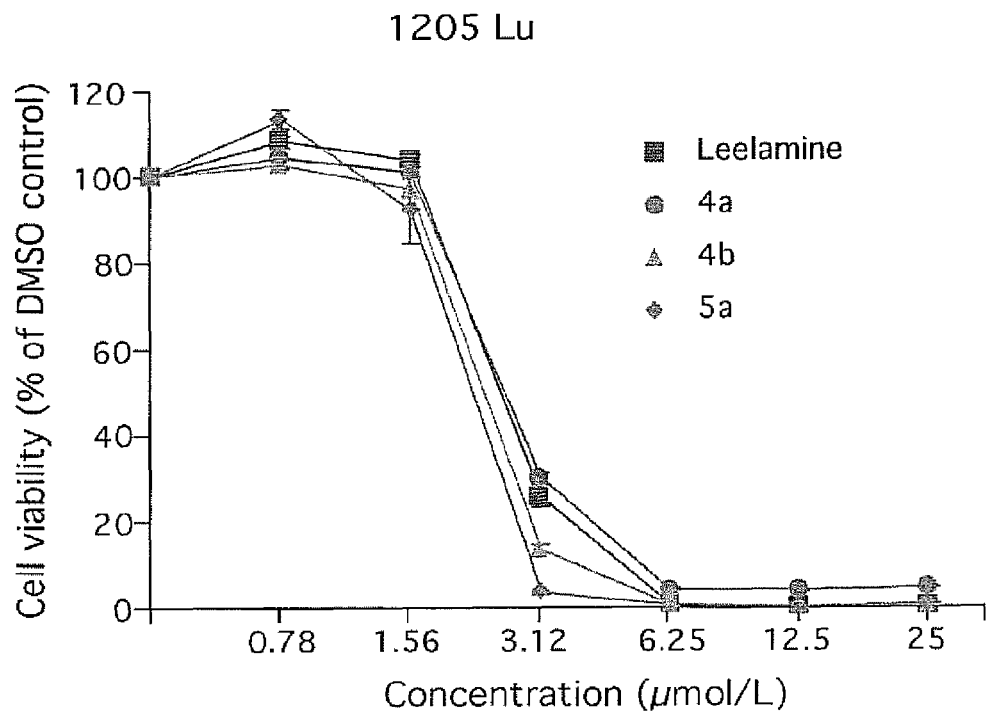
FIG. 54 is a graph showing effects of leelamine and compounds 4a, 4b and 5a on viability of melanoma cells.

Results of these assays for leelamine compared to compounds 4a, 4b and 5a in UACC 903 and 1205 Lu human melanoma cells are shown in FIGS. 53 and 54.

The $IC_{50}$ values for dehydroabietylamine, its N-substituted derivatives and the corresponding dihydroabietylamine and its N-substituted derivatives are depicted in Tables 4 and 5.

TABLE 4

$IC_{50}$ values for dehydroabietylamine and Abeitic acid derivatives against normal fibroblast and metastatic melanoma cell lines

| Compound Name | Normal fibroblast FF2441 | Metastatic Melanoma Cell line | |
|---|---|---|---|
| | | UACC903 | 1205Lu |
| Abietic acid | >100 | >100 | >100 |
| Leelamine | 8.91 ± 0.57 | 1.35 ± 0.05 | 1.93 ± 0.16 |
| 2a | >100 | >100 | >100 |
| 2b | >100 | 52.64 ± 1.34 | 60.37 ± 1.61 |
| 3a | >100 | 70.14 ± 1.80 | 81.09 ± 2.09 |
| 3b | >100 | >100 | >100 |
| 3c | >100 | >100 | >100 |
| 4a | 8.33 ± 0.43 | 2.13 ± 0.19 | 2.87 ± 0.07 |
| 4b | 9.33 ± 1.27 | 2.36 ± 0.25 | 2.38 ± 0.14 |
| 4c | >100 | 24.42 ± 1.33 | 24.33 ± 2.50 |
| 5a | 5.17 ± 0.02 | 1.28 ± 0.05 | 2.08 ± 0.05 |
| 5b | >100 | 89.40 ± 3.31 | >50 |
| 5c | NT | >100 | NT |
| 5d | NT | 6.05 ± 1.32 | NT |
| 5e | >100 | >100 | >100 |

TABLE 5

Comparison of $IC_{50}$ values of active compounds on cancer cell lines

| Compound | Cancer Cell Lines | | | | | | |
|---|---|---|---|---|---|---|---|
| | Melanoma (UACC903) | Breast (MCF-7) | Prostate (PC-3) | Prostate (LnCap) | Fibro Sarcoma (HT-1080) | Liver (A-459) | Fibroblast FF2441 |
| Abietic acid | >100 | >100 | >100 | >100 | >100 | >100 | >100 |
| Leelamine | 1.35 ± 0.5 | 6.42 ± 0.52 | 4.85 ± 1.09 | 10.90 ± 2.11 | 3.75 ± 0.54 | 9.27 ± 1.43 | 8.91 ± 0.57 |
| 4a | 2.36 ± 0.25 | 8.69 ± 1.81 | 9.73 ± 1.04 | 14.85 ± 1.99 | 6.29 ± 1.10 | 19.05 ± 3.87 | 8.33 ± 0.43 |
| 4b | 2.36 ± 0.25 | 9.04 ± 2.43 | 10.71 ± 0.87 | 22.35 ± 3.31 | 4.54 ± 0.87 | 15.30 ± 1.83 | 9.33 ± 1.27 |
| 5a | 1.28 ± 0.05 | 4.39 ± 0.71 | 4.66 ± 0.55 | 8.63 ± 0.97 | 3.73 ± 0.54 | 9.70 ± 1.34 | 5.17 ± 0.02 |

Figure 56:
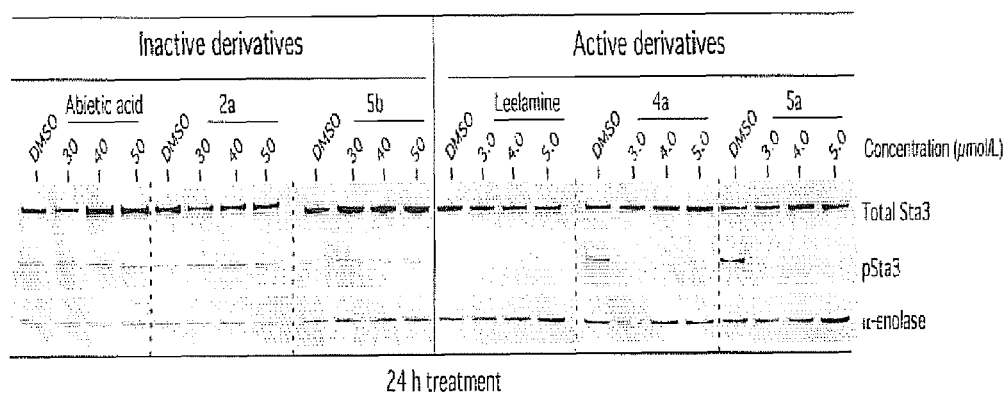
FIG. 56 is an image of a Western blot showing effects of abietic acid, leelamine, compound 2a, 4a, 5a or 5b treatment of melanoma cells on STAT signaling pathways regulating melanoma development.
Figure 55:
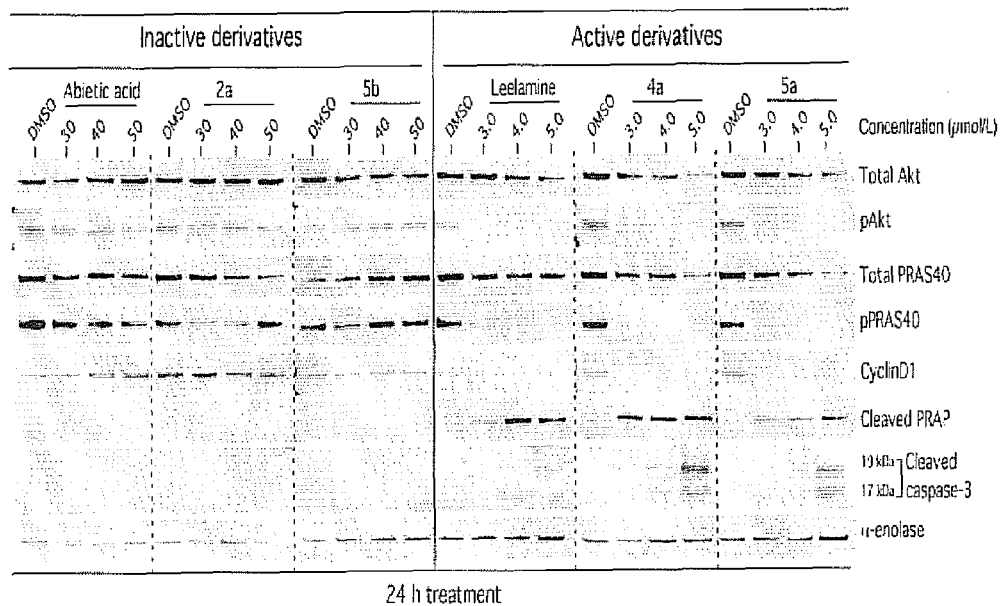
FIG. 55 is an image of a Western blot showing effects of abietic acid, leelamine, compound 2a, 4a, 5a or 5b treatment of melanoma cells on PI3K/Akt signaling pathways regulating melanoma development.
Figure 57:
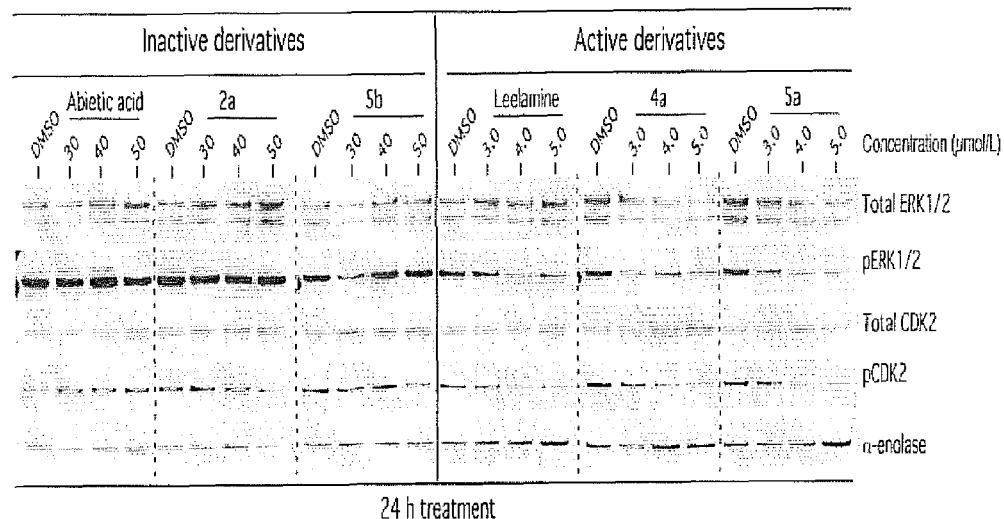
FIG. 57 is an image of a Western blot showing effects of abietic acid, leelamine, compound 2a, 4a, 5a or 5b treatment of melanoma cells on MAPK signaling pathways regulating melanoma development.

Abietic acid has no anti-cancer activity against any of the melanoma cell lines used and is unable to affect the PI3K pathway as indicated by unchanged pAKT, pPRAS40 and cyclin D1 levels; the MAPK pathway as indicated by unchanged expression of total and pERK1/2; or the STAT3 pathway as indicated by unaffected total and pSTAT3 levels; after 24 hour treatment with abietic acid at concentrations ranging from 30-50 µmol/L (FIGS. 55, 56 and 57). In contrast, dehydroabietylamine, also known as leelamine, is highly effective in abolishing activation of AKT pathway as shown by lower levels of pAKT, pPRAS40 and cyclin D1; and antagonizing the STAT3 pathway where it completely blocked pSTAT3 expression. Leelamine treatment increases the expression of cleaved PARP and caspase-3 and blocks activation of ERK1/2 as indicated by decrease in pERK1/2 and reduced the pCDK2 levels (FIGS. 55, 56 and 57) in a dose dependent manner.

Esterification of abietic acid to produce a more lipophilic compound 2a has no effect on the anti-cancer actions of abietic acid, while reduction to abietyl alcohol 2b produces a compound characterized by anti-cancer activity on both UACC 903 and 1205Lu cell lines with $IC_{50}$ of 53 and 60 µmol/L, respectively. The weak acidity of compound 2b compared to abietic acid likely confers the anti-cancer activity of 2b compared to the inactive abietic acid.

Abietic acid is modified to produce neutral amides of structures 3a, 3b and 3c. Compound 3a is characterized by anti-cancer action on both UACC 903 and 1205Lu cell lines with $IC_{50}$ of 70 and 81 µmol/L, respectively. Compounds 3b and 3c have $IC_{50}$>100 µmol/L. Modification of amides 3a, 3b and 3c to respective basic amines produces compounds 4a, 4b and 4c, characterized by anti-cancer activity. $IC_{50}$ for UACC903 cells is 2.13, 2.36 and 24.42 µmol/L for compounds 4a, 4b and 4c, respectively. $IC_{50}$ for 1205Lu cells is 2.87, 2.38 and 24.33 µmol/L for compounds 4a, 4b and 4c, respectively.

Modifications at the amino group of leelamine are made. Small substituents like trifluoroacetyl, compound 5a, produce compounds characterized by potent anti-cancer activity. Compound 5a has $IC_{50}$ 1.2 and 2.0 µmol/L for UACC903 and 1205Lu, respectively. Acetyl substitution produces compound 5b which has $IC_{50}$ 89 and >50 µmol/L for UACC903 and 1205Lu, respectively. The neutral behavior of amides in the case of compound 5b contrasts with the highly electronegative trifluoromethyl of compound 5a which alters the electron density on the nitrogen by an inductive effect. Modification of leelamine to include benzoyl, compound 5c, produces a compound characterized by $IC_{50}$>100 µmol/L. Modification of leelamine to include benzyl, compound 5d produces a compound characterized by $IC_{50}$ 6 µmol/L.

Modification of leelamine to include trityl, compound 5e, produces a compound characterized by $IC_{50}$>100 µmol/L, stearically hindering access of the amine —NH from interacting with protein active sites and abolishing the anti-cancer action. Thus, the amino group provides anti-cancer activity of leelamine, leelamine deriviatives, abietylamine and abietylamine derivatives. Small functional substitutions on the amine function, such as methyl (compound 4b), trifluoromethyl (compound 5a) 9 and benzyl (compound 5c) preserve the anti-cancer actions of these leelamine deriviatives and abietylamine derivatives whereas bulkier substitutions on the amine either weaken or destroy the anti-cancer activity on both melanoma cell lines. Analysis of compound pKa using Marvin 5.5.0.1 software indicates compounds described herein with pKa in the range of 6-11, inclusive, have potent anti-cancer activity, while pKa below 6 or greater than 11 produced inactive analogs. In summary, leelamine deriviatives and abietylamine derivatives shown in structures I and II having an amino group with at least one hydrogen atom, and having a pKa in the range of 6 to 11, inclusive, have similar anti-cancer activity compared to leelamine and abietylamine. Dihydroabietyl and dehydroabietyl ring systems have similar molecular arrangements and can be interchanged with no change in the activity on the melanoma cells.

Western Blot Analysis

Cell lysates are harvested by addition of RIPA lysis buffers containing 25 mM Tris·HCl pH 7.6, 150 mM NaCl, 1% NP-40, 1% sodium deoxycholate, 0.1% SDS, 10 mM EDTA, 1 mM sodium orthovanadate, 0.1 mM sodium molybdate, 1 mM phenylmethylsulfonyl fluoride, 20 µg/mL aprotinin, and 5 µg/mL leupeptin. The cell lysates are harvested and processed as described. Treatment conditions: $1-1.5 \times 10^6$ melanoma cells are plated in 100 mm culture dishes, 48 h later, treated with inactive derivatives of abietic acid, 2a and 5b (30-50 µmol/L) and active derivatives of leelamine, 4a and 5a (3-5 µmol/L) for 24 hours. Protein lysates collected for Western blotting. The blots are probed with antibodies according to each supplier's recommendations: antibodies to total Akt, phospho-Akt (Ser473), total PRAS40, phospho-PRAS40 (Thr246), total Erk1/2, phospho-Erk1/2 (Thr202/Tyr 204), total CDK2, phospho-CDK2 (Thr160), total Stat, phospho-Stat3 (Tyr705), caspase 3 and cleaved PARP from Cell Signaling Technology (Danvers, Mass.); total PRAS40 from Invitrogen (Carlsbad, Calif.); cyclin D1, α-enolase and secondary antibodies conjugated with horseradish peroxidase from Santa Cruz Biotechnology (Santa Cruz, Calif.). Immunoblots are developed using the enhanced chemiluminescence (ECL) detection system (Thermo Fisher Scientific, Rockford, Ill.). Intensity of protein bands is quantified using ImageJ software. Leelamine and compounds 4a and 5a decrease pAKT, pPRAS40 and cyclin D1 and induce cleaved PARP and caspase-3. Leelamine, compound 4a and compound 5a decrease pSTAT3 expression at all doses. Dose dependent reduction of pERK1/2 and pCDK2 is observed using compounds 4a, 5a and leelamine. Compounds 4a, 5a and leelamine inhibit these signaling pathways involved in melanoma.

Example 9

In this example, leelamine and related compounds of the present invention are administered to normal fibroblasts (FF2441 cell line) or metastatic melanoma cells (UACC903 and 1205 LU cell lines). Table 6 shows $IC_{50}$ for the indicated compounds.

TABLE 6

| Name of Compounds | Normal fibroblast FF2441 | Metastatic melanoma UACC 903 | Metastatic melanoma 1205 Lu |
|---|---|---|---|
| Abetic acid | >100 | >100 | >100 |
| Leelamine | 8.91 ± 0.57 | 1.35 ± 0.05 | 1.93 ± 0.16 |
| GPR-2 | >100 | 70.14 ± 1.80 | 81.09 ± 2.09 |
| GPR-3 (Abietylamine) | 8.33 ± 0.43 | 2.13 ± 0.19 | 2.87 ± 0.07 |
| GPR-6 | >100 | >100 | >100 |
| GPR-7 | 9.33 ± 1.27 | 2.36 ± 0.25 | 2.38 ± 0.14 |
| GPR-8 | >100 | 52.64 ± 1.34 | 60.37 ± 1.61 |
| GPR-12 | >100 | 24.42 ± 1.33 | 24.33 ± 2.50 |
| GPR-13 | >100 | >100 | >100 |
| GPR-1L | 5.17 ± 0.02 | 1.28 ± 0.05 | 2.08 ± 0.05 |
| GPR-2L | >100 | >100 | >100 |
| GPR-4L | >100 | 89.40 ± 3.31 | >100 |
| GPR-5L | 4.10 ± 0.24 | 1.01 ± 0.08 | 1.88 ± 0.21 |
| GPR-7L | NT | >100 | NT |
| GPR-8L | NT | 6.05 | NT |

Figure 58:
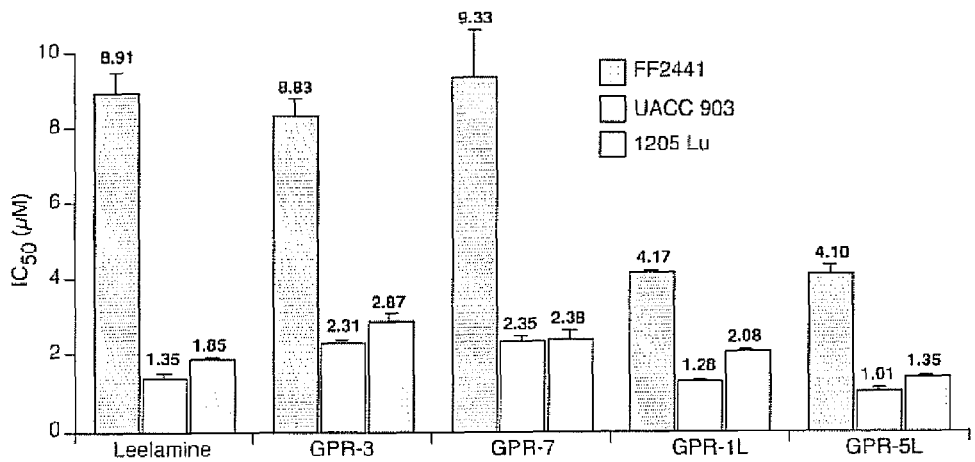
FIG. 58 is a graph showing effects of leelamine and compounds GPR-3, GPR-7, GPR-1L and GPR-5L on melanoma cells compared to normal fibroblast cells.

FIG. 58 is a graph showing $IC_{50}$ for the indicated compounds administered to FF2441 cells (left bars of each group of three bars for the indicated agent); UACC 903 cells (middle bars of each group of three bars for the indicated agent); and 1205 Lu cells (right bars of each group of three bars for the indicated agent).

Figure 59:
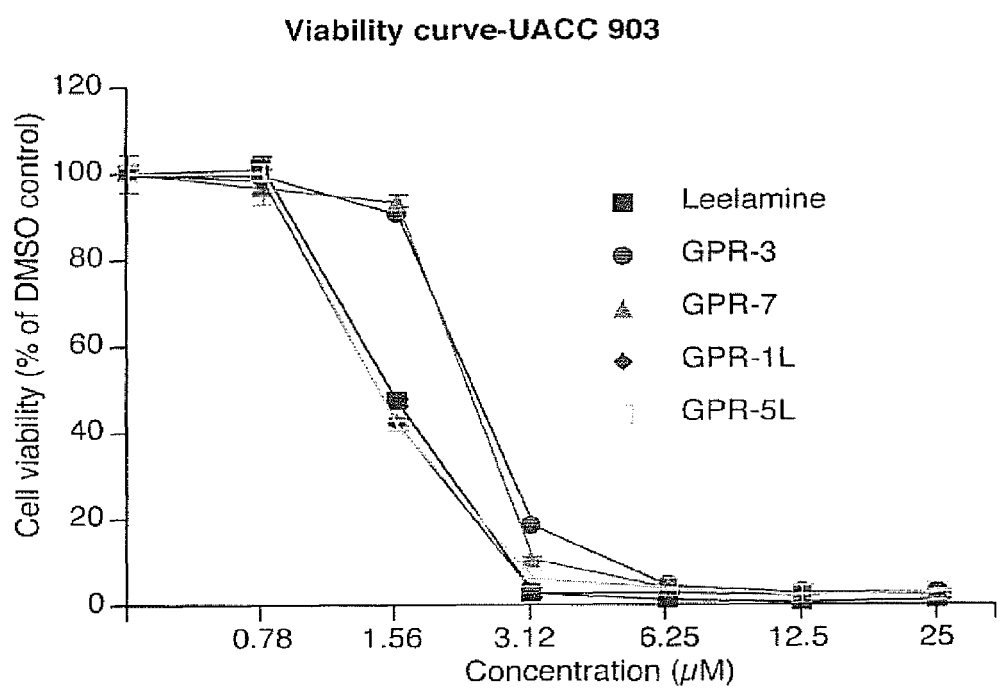
FIG. 59 is a graph showing effects of leelamine and compounds GPR-3, GPR-7, GPR-1L and GPR-5L on viability of melanoma cells.
Figure 60:
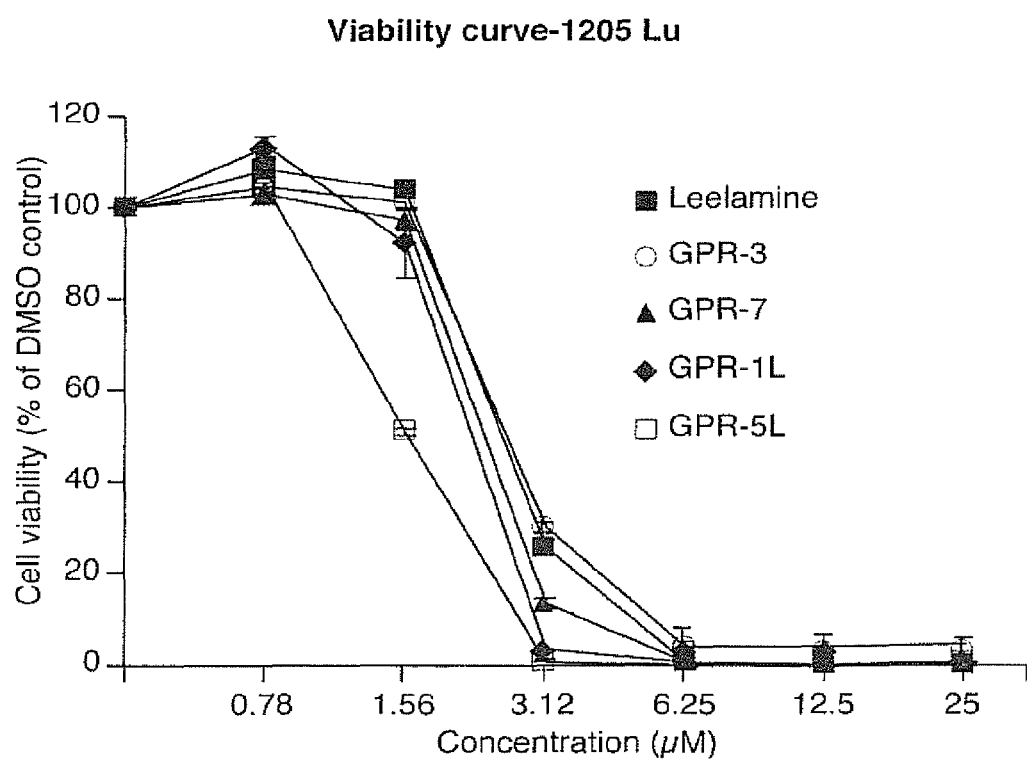
FIG. 60 is a graph showing effects of leelamine and compounds GPR-3, GPR-7, GPR-1L and GPR-5L on viability of melanoma cells.

FIGS. 59 and 60 are graphs showing the effects of the indicated compounds on viability of UACC 903 or 1205 Lu melanoma cells, respectively.

Table 7 shows a comparison of physiochemical properties and activities of the indicated compounds.

TABLE 7

| Name | pKa values at N | H Bond Acceptor/ Donors | Log D | $IC_{50}$ (UACC903) |
|---|---|---|---|---|
| Abietic Acid/GPR-1 | 4.59 | D = 0, A = 2 | 2.52 | >100 |
| Abietyl alcohol/GPR-8 | 18.65 | D = 1, A = 1 | 4.96 | 52.64 |
| Abietylamine/GPR-3 | 9.90 | D = 3, A = 0 (ammonium ion) | 2.42 | 2.13 |
| Abieticamide/GPR-2 | 16.46 | D = 1, A = 1 | 4.58 | 70.14 |
| N-methylabieticamide/GPR-6 | 16.05 | D = 1, A = 1 | 4.79 | >100 |
| N-methylabietylamine/GPR-7 | 10.59 | D = 1, A = 0 | 2.2 | 2.36 |
| N,N-diethylabieticamide/GPR-11 | — | D = 0, A = 1 | 5.73 | — |
| N,N-diethylabietylamine/GPR-12 | 10.7 | D = 1, A = 0 | 3.52 | 24.42 |
| Leelamine | 9.90 | D = 3, A = 0 (ammonium ion) | 2.81 | 1.35 |
| N-acetylleelamine/GPR-4L | 16.09 | D = 1, A = 1 | 5.10 | 89.40 |
| N-trifluoroacetylleelamine/GPR-1L | 6.92 | D = 1, A = 1 | 5.97 | 1.28 |
| N-trifluoroacetylleelamine/GPR-5L | 8.80 | D = 1, A = 1 | 7.33 | 1.01 |
| N-benzoylleelamine/GPR-7L | 15.00 | D = 1, A = 1 | 6.83 | >100 |
| N-benzoylleelamine/GPR-8L | 10.6 | D = 2, A = 0 | 4.65 | 6.05 |

Example 10

Dosing Regimen and Dosages

Human dosing regime and dosages can be determined using standard methods such as based on the Oncology Tools: Dose Calculator (http://www.accessdata.fda.gov/scripts/cder/onctools/animalquery.cfm)

The following conversion factors can be used to calculate dose: Mouse=3, Hamster=4.1, Rat=6, Guinea Pig=7.7, based on Cancer Chemother Repts 50(4):219 (1966). The conversion factor is multiplied by the animal dose in mg/kg to obtain the dose in mg/m² for the human dose equivalent. When both height and weight are known, human body surface area is calculated using Boyd's Formula of Body Surface Area (Boyd E. The growth of the surface area of the human body, University of Minnesota Press. 1935). Calculations with weight alone (no height) are less accurate. All values are estimates and values above 2.25 m$^2$ are not considered accurate. Reference: Reagan-Shaw et al. 2007. Dose translation from animal to human studies Revisited. The FASEB Journal, Vol. 22 March.

TABLE 8

Dosing regimen and dosages

| Species | Weight, kg | Est. Total Dose, mg | Dose in mg/kg | Dose in mg/m2 | Est. BSA, m2 |
|---|---|---|---|---|---|
| Human | 65.00 | 1950.00 | 30.00 | 1140.09 | 1.792 |
| Mouse | 0.02 | 0.60 | 30.00 | 90.48 | 0.007 |
| Hamster | 0.03 | 0.90 | 30.00 | 103.69 | 0.009 |
| Rat | 0.15 | 4.50 | 30.00 | 177.11 | 0.025 |
| Guinea Pig | 1.00 | 30.00 | 30.00 | 337.08 | 0.089 |
| Rabbit | 2.00 | 60.00 | 30.00 | 377.98 | 0.159 |
| Cat | 2.50 | 75.00 | 30.00 | 380.53 | 0.197 |
| Monkey | 3.00 | 90.00 | 30.00 | 366.67 | 0.245 |
| Dog | 8.00 | 240.00 | 30.00 | 535.71 | 0.448 |

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. An anti-cancer pharmaceutical composition, comprising: liposome encapsulated leelamine, wherein the liposomes comprise L-alpha-phosphatidylcholine and 1,2-dipalmitoyl-sn-glycero-3-phosphoethanolamine-N-[methoxy(polyethylene glycol)-2000 in an 80:20 mol % ratio and wherein the liposomes have a net neutral surface charge at physiological pH.

2. A method of treating a subject having cancer, comprising:
    administering a therapeutically effective amount of the anti-cancer pharmaceutical composition of claim 1 to the subject.

3. The method of claim 2, wherein the anti-cancer pharmaceutical composition is effective to preferentially inhibit the PI3K, MAPK and STAT pathways in a cancer cell compared to a non-cancer cell.

4. The method of claim 2, wherein the subject is human.

5. The method of claim 2, further comprising administration of an adjunct anti-cancer treatment.

* * * * *